US009624260B2

(12) United States Patent
Lihme

(10) Patent No.: US 9,624,260 B2
(45) Date of Patent: *Apr. 18, 2017

(54) PROCESS FOR ISOLATION OF PLASMA OR SERUM PROTEINS

(75) Inventor: Allan Otto Fog Lihme, Birkerød (DK)

(73) Assignee: Therapure Biopharma Inc., Mississauga, Ontario (CA)

( * ) Notice: Subject to any disclaimer, the term of this patent is extended or adjusted under 35 U.S.C. 154(b) by 1572 days.

This patent is subject to a terminal disclaimer.

(21) Appl. No.: 11/570,154

(22) PCT Filed: Jun. 7, 2005

(86) PCT No.: PCT/DK2005/000378
§ 371 (c)(1),
(2), (4) Date: Jul. 13, 2007

(87) PCT Pub. No.: WO2005/121163
PCT Pub. Date: Dec. 22, 2005

(65) Prior Publication Data
US 2007/0299251 A1  Dec. 27, 2007

(30) Foreign Application Priority Data

Jun. 7, 2004 (DK) .................. 2004 00891
Jul. 5, 2004 (DK) .................. 2004 01062

(51) Int. Cl.
| | | |
|---|---|---|
| C07K 1/18 | (2006.01) | |
| C07K 1/16 | (2006.01) | |
| C07K 14/47 | (2006.01) | |
| C07K 14/75 | (2006.01) | |
| C07K 14/755 | (2006.01) | |
| C07K 14/76 | (2006.01) | |
| C07K 14/81 | (2006.01) | |
| B01D 15/08 | (2006.01) | |
| B01D 15/20 | (2006.01) | |
| B01D 15/42 | (2006.01) | |
| C07K 14/79 | (2006.01) | |
| C07K 16/00 | (2006.01) | |

(52) U.S. Cl.
CPC .............. *C07K 1/16* (2013.01); *B01D 15/08* (2013.01); *B01D 15/206* (2013.01); *B01D 15/424* (2013.01); *C07K 14/47* (2013.01); *C07K 14/75* (2013.01); *C07K 14/755* (2013.01); *C07K 14/76* (2013.01); *C07K 14/79* (2013.01); *C07K 14/81* (2013.01); *C07K 16/00* (2013.01)

(58) Field of Classification Search
None
See application file for complete search history.

(56) References Cited

U.S. PATENT DOCUMENTS

| | | | | |
|---|---|---|---|---|
| 2,390,074 A | * | 12/1945 | Cohn ........................ | 530/364 |
| 2,469,193 A | | 5/1949 | Cohn et al. | |
| 4,156,681 A | | 5/1979 | Schneider et al. | |
| 4,416,783 A | | 11/1983 | Noguchi et al. | |
| 4,481,189 A | | 11/1984 | Prince | |
| 4,749,783 A | * | 6/1988 | Jordan et al. ............... | 530/393 |
| 5,055,485 A | * | 10/1991 | Geacintov et al. ........... | 514/449 |
| 5,258,503 A | * | 11/1993 | Yokohari et al. ............ | 530/415 |
| 6,036,861 A | | 3/2000 | Flickinger et al. | |
| 6,093,324 A | * | 7/2000 | Bertolini et al. ............ | 210/635 |
| 6,617,133 B1 | | 9/2003 | Noda et al. | |
| 7,442,779 B2 | * | 10/2008 | Lihme et al. ................. | 530/413 |
| 2002/0035241 A1 | | 3/2002 | Buchacher et al. | |
| 2002/0104801 A1 | | 8/2002 | Voute et al. | |

FOREIGN PATENT DOCUMENTS

| | | |
|---|---|---|
| EP | 0 722 771 B1 | 7/1996 |
| WO | WO 92/00799 | 1/1992 |
| WO | WO 92/16292 | 10/1992 |
| WO | WO 92/18237 | 10/1992 |
| WO | WO 97/17132 | 5/1997 |
| WO | WO 98/08603 | 3/1998 |
| WO | WO 99/51316 | 10/1999 |
| WO | WO 99/65586 | 12/1999 |
| WO | WO9961475 A1 | 12/1999 |
| WO | WO 00/25884 | 5/2000 |
| WO | WO 00/57982 | 10/2000 |
| WO | WO 01/85329 A2 | 11/2001 |
| WO | WO 02/05923 A1 | 1/2002 |
| WO | WO 02/053251 A1 | 7/2002 |
| WO | WO 02/096215 A1 | 12/2002 |
| WO | WO 2004/008138 A2 | 1/2004 |

(Continued)

OTHER PUBLICATIONS

Chisti et al. (Biotech. Adv., vol. 8, pp. 699-708, 1990).*
Dong et al. (J. Of Chromat., 1245, 0ages 143-149, 2012).*
Chisti et al. (Biotech Adv., vol. 8, 1990, pp. 699-708).*
A. Ingild, "4. Single Radial Immunodiffusion", Scand. J. Immunol. vol. 17, Suppl. 10, 41-56, 1983.
A. Karau et al., "The Influence of Particle Size Distribution and Operating Conditions on the Adsorption Performance in Fluidized Beds", Biotechnology and Bioengineering vol. 55, No. 1, Jul. 5, 1997, pp. 54-64.
Akinori Sumi et al., "Purification of Recombinant Human Serum Albumin Efficient purification using STREAMLINE", Bioseparation 8: 195-200, 1999.
G. M. S. Finette et al., "Optimization Considerations for the Purification of α1-Antitrypsin Using Silica-Based Ion-Exchange Adsorbents in Packed and Expanded Beds", Biotechnol. Prog., 1998, 14, 286-293.

(Continued)

*Primary Examiner* — Hope Robinson
(74) *Attorney, Agent, or Firm* — Bereskin & Parr LLP/S.E.N.C.R.L., s.r.l.; Micheline Gravelle

(57) ABSTRACT

The present invention provides a process for the isolation of one or more proteins) from a protein solution. The process comprising the steps of: a) providing a protein solution comprising one or more specific proteins) and having a preset pH and a preset ionic strength or conductivity, b) applying the protein solution to a packed bed or expanded bed column comprising an adsorbent, and c) obtaining one or more proteins) from the column; wherein the protein solution has been supplemented with an alcohol.

62 Claims, 5 Drawing Sheets

(56) References Cited

FOREIGN PATENT DOCUMENTS

WO    WO 2004/082397 A1    9/2004

OTHER PUBLICATIONS

E. J. Cohn et al., "Preparation and Properties of Serum and Plasma Proteins. IV. A System for the Separation into Fractions of the Protein and Lipoprotein Components of Biological Tissues and Fluids", Journal of American Chemical Society, vol. LXVIII, Jan.-Jul. 1946, pp. 459-475.
Malvern Instruments Ltd. (Worcestershire, UK) in the Operators guide (MAN 0320 Issue 1.0 Mar. 2004) to the Mastersizer 2000E. Communication pursuant to Article 94(3) EPC European Application No. 05 746 285.5-1223 dated Dec. 5, 2011.
T. Burnouf, "Chromatography in plasma fractionation: benefits and future trends", Journal of Chromatography B, 664 (1995) 3-15.
European Search Report issued on Nov. 4, 2016.
Lihme, A. et al., "A novel core fractionation process of human plasma by expanded bed adsorption chromatography", Analytical Biochemistry, Academic Press Inc. New York, vol. 399, No. 1, Apr. 1, 2010.
Schaller et al., "Blood Plasma Protein," *Human Blood Plasma Proteins: Structure And Function*, pp. 17-20 (2008).
Vogler et al., Contact Activation of Blood Plasma Coagulation: A Contribution from the Hematology at Biomaterial Interfaces Research Group The Pennsylvania State University, *Biomaterials*, vol. 30, No. 10, pp. 1857-1869 (2009).
Margolis, "Initiation of Blood Coagulation by Glass and Related Surfaces," *J. Physiol.*, vol. 137, pp. 95-109 (1957).
Chatterjee et al., "Contributions of Contact Activation Pathways of Coagulation Factor XII in Plasma," J. Biomed. Mater Res. A., vol. 90, No. 1, pp. 27-34 (2009).
Schaller et al., "Inhibitors," *Human Blood Plasma Proteins: Structure And Function*, pp. 283-298 (2008).
Schaller et al., "Enzymes," *Human Blood Plasma Proteins: Structure And Function*, pp. 231-257 (2008).
Schaller et al., "Blood Coagulation and Fibrinolysis," *Human Blood Plasma Proteins: Structure And Function*, pp. 91-109 (2008).
Li et al., "Purification of Human Immunoglobulin G: a New Approach to Plasma Fractionation," *Vox Sanguinis*, vol. 83, pp. 332-338 (2002).
Marion Fischer, "Dissertation: Initiation of Blood Coagulation—Evaluating the Relevance of Specific Surface Functionalities using Self Assembled Monolayers," 111 pages, Apr. 30, 2010.

\* cited by examiner

PROCESS FOR ISOLATION OF PLASMA OR SERUM PROTEINS

FIELD OF THE INVENTION

The present invention relates to the large-scale fractionation and isolation of protein(s), such as human plasma or serum protein(s), from a protein solution. In particular the present invention relates to large-scale manufacture of therapeutic plasma or serum protein(s) from sources such as blood, plasma, serum or other blood derived sources using an adsorbent coupled with a ligand for the capture of the protein(s), from the protein solution.

TECHNICAL BACKGROUND AND PRIOR ART

Human and animal blood comprises many proteins and enzymes, which possess therapeutic and potentially lifesaving properties. Some of these proteins may be found in the red blood cells whereas others are found in solution in plasma or serum. Since the middle of the $20^{th}$ century such proteins have been the target for large-scale and specific isolation with the aim of purifying and standardising the proteins for use as human therapeutic agents. Examples of prominent blood proteins that are currently available as isolated therapeutic products are: albumin, immunoglobulin G, Factor VIII and alpha-1-proteinase inhibitor. Some of these proteins are produced in the scale of several thousand kg per year (albumin and IgG) while others are produced only in the gram to kilogram per year scale. However, on a worldwide basis many million litres of blood per year are processed for the purpose of isolating these proteins.

Blood, blood plasma and blood serum are extremely complicated protein containing solutions that comprises many other types of compounds other than the protein(s) or enzyme(s) of interest, all carefully balanced and regulated to work in the blood-stream in a very broad range of biochemically complicated functions such as the oxygen transport, the immuno defence and the coagulation system preventing excessive bleeding from wounds. Especially when blood is drawn from an animal and exposed to the atmosphere and the surface of different types of containers it becomes highly unstable. Although chemical agents, such as heparin and sodium citrate, can be added to increase the stability and to a certain degree prevent coagulation of the blood plasma obtained by separating the blood cells, the plasma will still be a very fragile, highly concentrated and viscous protein solution also comprising significant amounts of lipids. Despite the addition of stabilisers any handling or alteration of the plasma composition involves the risk of accidental destabilisation, which may cause activation of the coagulation cascade, precipitation of e.g. lipid components as well as denaturation of the target protein(s) and thereby makes the blood very difficult to work with. Thus, any method employed to isolate proteins from blood or blood derived solutions must take the inherent instability of the solution and the proteins themselves into consideration. This has proven to be a very significant challenge for the large-scale production of therapeutic products from blood.

Further, from a technological point of view the complexity and instability of the blood makes the separation and isolation of blood proteins much more complicated and economically demanding than the isolation of proteins from other types of protein solution such as mammalian cell culture supernatants and fermentation broth from genetically modified microorganisms as typically used in the biotech industry. Also, the biotech industry will typically only isolate one specific product from a cell culture supernatant, while for economical and ethical reasons the therapeutic blood fractionation industry generally must isolate as many products as possible from the limited amount of blood available.

The cost of blood, serum and plasma has increased very significantly during the last decades the main reason being due to increased cost of the safety measures needed to prevent viral diseases to spread from blood donors to recipients of the blood products. For more than 10-20 years the very high cost of the blood plasma as well as increased costs of implementing viral elimination steps and other safety measures during processing has put the blood fractionation industry under a significant pressure to increase the per-litre-yield of individual products such as immunoglobulin G (IgG) and alpha-1-proteinase inhibitor.

Furthermore, there is generally a strong need for expanding the number of products that can be produced from the same amount of plasma i.e. to produce an increased number of different proteins from the plasma, while still being able to produce the existing products at acceptable yields. The blood fractionation industry has experienced that these long felt needs are difficult to satisfy with known technology and although attempts have been made for a long time to employ modern adsorption techniques as an alternative to the established precipitation methods there are still significant problems in terms of economical feasibility and processing robustness of hitherto described adsorption methods.

One of the conventionally used methods for the fractionation of blood plasma or blood serum protein(s) has been described in U.S. Pat. No. 2,390,074 (Cohn et al.) which discloses a method for the fractionation of plasma or serum proteins in large-scale which utilise ethanol precipitation and regulates temperature, pH, ionic strength and time to control precipitation of certain proteins from human plasma. The fractionation method involves the stepwise addition of ethanol to the plasma raw material in order to obtain several precipitates (fractions) and corresponding supernatants comprising different enriched protein solutions.

One drawback of the ethanol precipitation method disclosed by Cohn et al. is that some proteins tend to denature during the process resulting in decreased yield of the protein to be isolated and contamination with aggregates that needs to be removed before an acceptable therapeutic product can be obtained. Furthermore, during this fractionation method precipitated proteins have to be resolubilised for further processing. Such resolubilised protein solutions may comprise significant levels of insoluble (denatured) protein and lipid material that makes it difficult and time consuming to work-up the target product, which also contributes significantly to the loss of valuable product. Additionally it is characteristic of this process that a specific protein may distribute into several of the fractions obtained during the stepwise addition of ethanol, which again results in low yields and time-consuming work-up of re-combined protein fractions.

In the fractionation of e.g. alpha-1-proteinase inhibitor or immunoglobulins, such as IgG, using the fractionation method described by Cohn et al. the yield alpha-1-proteinase inhibitor is as low as 10-20% and the yield of IgG is as low as 40-50%. However, since these products are much needed and as there is an undersupply of the product to satisfy the needs of patients, new methods for isolating such products are highly needed where the loss of product is reduced.

During the last decade many attempts have been made to develop a fractionation process which can provide an increased yield using a range of other techniques, including chromatography. However, drawbacks associated with known adsorption techniques such as low flow rates and low binding capacities resulting in low productivity as well as lack of robustness and difficulties in applying safe cleaning procedures have made it difficult to balance the yield and economy involved in the fractionation of the blood plasma and serum proteins. The core of the existing industrial manufacturing processes is therefore still based on the work of Cohn et al.

Presently used isolation and purification processes have shown to be inadequate and trace impurities resulting from inefficient purification processes may be able to stimulate an immune response in patients. Furthermore, purification processes that fail to separate active and inactive part of the product, as the presently used processes, can lead to a product with unpredictable efficacy and a specific activity, which varies between separate lots.

Even attempts to develop advanced adsorption techniques such as expanded bed adsorption, which were first introduced in the beginning of the 1990ties, have failed to improve the employment of adsorption techniques. Finette G. M. S. et al, Biotechnol. Prog., 1998, 14, pp 286-293, thus describes the application of an adsorbent having a mean particle diameter of 180 micron and a density of 1.79 g/ml for packed bed and expanded bed adsorption of α-1-proteinase inhibitor from Cohn fraction II+III. The authors conclude that a volumetric flow rate of 0.2 ml/min (corresponding to a linear flow rate of 0.1 cm/min or 60 cm/hour) will result in a yield of alpha-1-proteinase inhibitor of 50%. The authors further state that higher flow rates will decrease the yield as well as disturb the plug flow in the column. Such low flow rates are not economically attractive and are therefore prohibiting the use of e.g. expanded bed adsorption for the industrial fractionation of blood proteins.

Other attempts to apply expanded bed adsorption for isolation of human plasma proteins confirms the low flow rates applied with prior techniques. U.S. Pat. No. 6,617,133 thus describes the use of a Streamline SP adsorbent (Amersham Biosciences), which, according to the supplier, have a mean volume particle diameter of 200 micron and a density of 1.20 g/ml for the isolation of human serum albumin using a raw material application flow rate of 100 cm/hour. Such a low flow rate is limiting the productivity of the adsorption system and thus requires very large columns and results in high materials cost per unit human albumin produced.

Accordingly, a process for the fractionation of serum or plasma proteins which is fast, robust (i.e. being reliable during daily operation with low down time), specific and safe, and which at the same time provides an improved yield and purity of the products of interest during processing and thereby facilitates an improved and acceptable balance between yield and economy, compared to the conventionally used processes, e.g. the process described by Cohn et al, and which solves the above mentioned problems is therefore desired. Such a process is provided herein.

SUMMARY OF THE INVENTION

Accordingly, the present invention relates to a process for the isolation and/or fractionation of protein solutions. The process of the present invention is fast, robust, specific and safe, and provides an improved yield and purity of the product of interest during processing and thereby facilitates an improved and acceptable balance between yield of product and economy involved, compared to the conventionally used methods. The process according to the invention is particularly suitable for large-scale production.

Thus, it is an aspect of the present invention to provide a process for the large-scale isolation of one or more protein(s) from a protein solution wherein the protein solution is obtained from a source selected from the group consisting of blood, such as serum and/or plasma, and other blood derived sources. The process comprises the steps of:
a) optionally adjusting the pH of the protein solution to a preset pH;
b) optionally adjusting the ionic strength or conductivity of the protein solution to a preset ionic strength or a preset conductivity;
c) applying said protein solution to an adsorption column comprising an adsorbent, said adsorbent comprises a particle with at least one high density non-porous core, surrounded by a porous material, the adsorbent comprises a particle density of at least 1.5 g/ml and a mean volume particle diameter of at most 150 μm;
d) optionally washing the column;
e) obtaining the one or more protein(s) from the adsorbent.

In another aspect of the present invention a process for the large-scale isolation of one or more blood protein(s), such as one or more serum protein(s) or one or more plasma protein(s), from a protein solution is provided. The process comprises the steps of:
a) optionally adjusting the pH of the protein solution to a preset pH;
b) optionally adjusting the ionic strength or conductivity of the protein solution to a preset ionic strength or a preset conductivity;
c) applying said protein solution to an adsorption column comprising an adsorbent, said adsorbent comprises a particle with at least one high density non-porous core, surrounded by a porous material, the adsorbent comprises a particle density of at least 1.5 g/ml and a mean volume particle diameter of at most 150 μm;
d) optionally washing the column;
e) obtaining the one or more protein(s) from the adsorbent.

In a further aspect of the present invention a process for the large-scale isolation of one or more protein(s) from a protein solution is provided. The process comprises the steps of:
a) optionally adjusting the pH of the protein solution to a preset pH;
b) optionally adjusting the ionic strength or conductivity of the protein solution to a preset ionic strength or a preset conductivity;
c) applying said protein solution to an adsorption, said adsorbent comprises a particle with at least one high density non-porous core, surrounded by a porous material, the adsorbent comprises a particle density of at least 1.5 g/ml and a mean volume particle diameter of at most 150 μm;
d) optionally washing the adsorbent;
e) obtaining the one or more protein(s) from the adsorbent.
wherein the protein solution has been supplemented with an alcohol.

In yet an aspect of the present invention a process for the large-scale isolation of one or more protein(s) from a protein solution is provided. The process comprises the steps of:
a) optionally adjusting the pH of the protein solution to a preset pH;
b) optionally adjusting the ionic strength or conductivity of the protein solution to a preset ionic strength or a preset conductivity;

c) applying said protein solution to an adsorption, wherein the adsorbent comprises a functionalised matrix polymer carrying a plurality of covalently attached functional groups comprising an aromatic or heteroaromatic ring-system and one or more acidic groups, d) optionally washing the adsorbent;

e) obtaining the one or more protein(s) from the adsorbent.

wherein the protein solution has been supplemented with an alcohol.

In another aspect of the present invention a process for the large-scale isolation of one or more protein(s) from a protein solution is provided. The process comprises the steps of:

a) providing a protein solution comprising one or more protein(s) and said protein solution having a preset pH and a preset ionic strength or conductivity, b) subjecting the protein solution to at least one virus elimination treatment prior to contacting the protein solution with an adsorbent, c) contacting said protein solution with an adsorbent, wherein the adsorbent comprises a functionalised matrix polymer carrying a plurality of covalently attached functional groups comprising an aromatic or heteroaromatic ring-system and one or more acidic groups, d) optional washing the adsorbent, and e) obtaining said one or more protein(s) from said adsorbent.

In another aspect of the present invention a process for the large-scale isolation of one or more protein(s) from a protein solution is provided. The process comprises the steps of:

a) providing a protein solution comprising one or more protein(s) and said protein solution having a preset pH and a preset ionic strength or conductivity, b) subjecting the protein solution to at least one virus elimination treatment prior to contacting the protein solution with an adsorbent, c) contacting said protein solution with an adsorbent, wherein said adsorbent comprises a particle with at least one high density non-porous core, surrounded by a porous material, d) optional washing the adsorbent, and e) obtaining said one or more protein(s) from said adsorbent.

In yet an aspect of the present invention a process for the large-scale isolation or separation of α-1 proteinase inhibitor is provided. The process comprises the steps of:

a) providing a protein solution comprising said α-1 proteinase inhibitor and having a preset pH and optionally a preset ionic strength or conductivity;

b) contacting said protein solution with an adsorbent, wherein the adsorbent comprises a functionalized matrix polymer carrying a plurality of covalently attached functional groups comprising an aromatic or heteroaromatic ring-system and one or more acidic groups; and c) obtaining said α-1 proteinase inhibitor from said adsorbent.

In an aspect of the present invention a process for the large-scale isolation or separation of α-1 proteinase inhibitor is provided. The process comprises the steps of:

a) providing a protein solution comprising said α-1 proteinase inhibitor and having a preset pH and optionally a preset ionic strength or conductivity;

b) contacting said protein solution with an adsorbent, said adsorbent comprises a particle with at least one high density non-porous core, surrounded by a porous material; and c) obtaining said α-1 proteinase inhibitor from said adsorbent.

In another aspect of the present invention a process for the large-scale isolation or separation of human albumin is provided. The process comprises the steps of:

a) providing a protein solution comprising said human albumin and having a preset pH and optionally a preset ionic strength or conductivity;

b) contacting said protein solution with an adsorbent, wherein the adsorbent comprises a functionalized matrix polymer carrying a plurality of covalently attached functional groups comprising an aromatic or heteroaromatic ring-system and one or more acidic groups; and c) obtaining said human albumin from said adsorbent.

In a further aspect of the present invention A process for the large-scale isolation or separation of fibrinogen is provided. The process comprises the steps of:

a) providing a protein solution comprising said fibrinogen and having a preset pH and optionally a preset ionic strength or conductivity;

b) contacting said protein solution with an adsorbent, wherein the adsorbent comprises a functionalized matrix polymer carrying a plurality of covalently attached functional groups comprising an aromatic or heteroaromatic ring-system and one or more acidic groups; and c) obtaining said fibrinogen from said adsorbent.

In yet an aspect of the present invention a process for the large-scale isolation or separation of fibrinogen is provided. The process comprises the steps of:

a) providing a protein solution comprising said fibrinogen and having a preset pH and optionally a preset ionic strength or conductivity;

b) contacting said protein solution with an adsorbent, said adsorbent comprises a particle with at least one high density non-porous core, surrounded by a porous material; and c) obtaining said fibrinogen from said adsorbent.

In another aspect of the present invention a process for the large-scale isolation or separation of transferrin is provided. The process comprises the steps of:

a) providing a protein solution comprising said transferrin and having a preset pH and optionally a preset ionic strength or conductivity;

b) contacting said protein solution with an adsorbent, wherein the adsorbent comprises a functionalized matrix polymer carrying a plurality of covalently attached functional groups comprising an aromatic or heteroaromatic ring-system and one or more acidic groups; and c) obtaining said transferrin from said adsorbent.

In a further aspect of the present invention a process for the large-scale isolation or separation of transferrin is provided. The process comprises the steps of:

a) providing a protein solution comprising said transferrin and having a preset pH and optionally a preset ionic strength or conductivity;

b) contacting said protein solution with an adsorbent, said adsorbent comprises a particle with at least one high density non-porous core, surrounded by a porous material; and c) obtaining said transferrin from said adsorbent.

In yet an aspect of the present invention a process for the large-scale isolation or separation of α-1-acid-glycoprotein is provided. The process comprises the steps of:
a) providing a protein solution comprising said α-1-acid-glycoprotein and having a preset pH and optionally a preset ionic strength or conductivity;
b) contacting said protein solution with an adsorbent, wherein the adsorbent comprises a functionalized matrix polymer carrying a plurality of covalently attached functional groups comprising an aromatic or heteroaromatic ring-system and one or more acidic groups; and
c) obtaining said α-1-acid-glycoprotein from said adsorbent.

In a further aspect of the present invention a process for the large-scale isolation or separation of α-1-acid-glycoprotein is provided. The process comprises the steps of:
a) providing a protein solution comprising said α-1-acid-glycoprotein and having a preset pH and optionally a preset ionic strength or conductivity;
b) contacting said protein solution with an adsorbent, said adsorbent comprises a particle with at least one high density non-porous core, surrounded by a porous material; and
c) obtaining said α-1-acid-glycoprotein from said adsorbent.

In another aspect of the present invention a process for the large-scale isolation or separation of one or more coagulation or anti-coagulation factor(s) such as Factor II, Factor V, Factor VII, Factor VIII, von Willebrand factor, Factor VIII—von Willebrand factor complex, Factor IX, Factor X, Factor XI, C1 inhibitor, protein C and/or Protein S is provided. The process comprises the steps of:
a) providing a protein solution comprising said one or more coagulation factor(s) and having a preset pH and optionally a preset ionic strength or conductivity;
b) contacting said protein solution with an adsorbent, wherein the adsorbent comprises a functionalized matrix polymer carrying a plurality of covalently attached functional groups comprising an aromatic or heteroaromatic ring-system and one or more acidic groups; and
c) obtaining said one or more coagulation factor(s) from said adsorbent.

In an aspect of the present invention a process for the large-scale isolation or separation of one or more coagulation or anti-coagulation factor(s) such as Factor II, Factor V, Factor VII, Factor VIII, von Willebrand factor, Factor VIII—von Willebrand factor complex, Factor IX, Factor X, Factor XI, C1 inhibitor, protein C and/or Protein S is provided. The process comprises the steps of:
a) providing a protein solution comprising said one or more coagulation factor(s) and having a preset pH and optionally a preset ionic strength or conductivity;
b) contacting said protein solution with an adsorbent, said adsorbent comprises a particle with at least one high density non-porous core, surrounded by a porous material; and
c) obtaining said one or more coagulation factor(s) from said adsorbent.

In another aspect of the present invention a process for the simultaneous large-scale isolation of at least 3, e.g. 4, such as 5, e.g. 6 of the protein(s) selected from α-1 proteinase inhibitor, IgG, human albumin, transferrin, α-1-acid-glycoprotein and fibrinogen is provided. The process comprises the steps of:
a) providing a protein solution comprising at least three of said α-1 proteinase inhibitor, IgG, human albumin, transferrin, α-1-acid-glycoprotein and fibrinogen and said protein solution having a preset pH and optionally a preset ionic strength or conductivity;
b) contacting said protein solution with an adsorbent; and
c) obtaining from said adsorbent at least 3, e.g. 4, such as 5, e.g. 6 of the proteins selected from the group consisting of α-1 proteinase inhibitor, IgG, human albumin, transferrin, α-1-acid-glycoprotein and fibrinogen separated from each other in individual protein fractions.

DETAILED DISCLOSURE OF THE INVENTION

During the last decade the development within expanded bed adsorption has gained more and more attention due to the great applicability for large-scale purification. Proteins can be purified from a crude protein solution without the need for separate clarification, concentration and other types of initial purification to remove particulate matter. The adsorbents, used for expanded bed adsorption, capture the target molecules using the same principles as affinity, ion exchange or hydrophobic interaction chromatography.

The basic concept and prior art in the field of expanded bed adsorption have been described in e.g. EP 0 722 771, WO 01/85329, WO 92/18237, WO 2000/25884, WO 02/05923, WO 99/65586 and WO 00/57982 which discloses different types of expanded bed adsorption apparatus and equipment as well as different types of adsorption particles which have been found by the present inventors to be suitably adapted or further developed for the isolation of serum or plasma proteins as described in the present invention. All these documents are incorporated herein by reference.

In an embodiment of the present invention the process according to the present invention may be performed at a large-scale. In the present context the term "large-scale" relates to the processing of a raw material volume of at least 1 liters per adsorption cycle, such as at least 5 liters per adsorption cycle, such as at least 10 liters per adsorption cycle, such as at least 25 liters per adsorption cycle, such as at least 100 liters per adsorption cycle, such as at least 1000 liters per adsorption cycle and thus distinguish the invention from any analytical and small scale experiments that do not relate to the severe requirements for robustness and reproducibility as in an industrial large-scale production environment.

The Protein Solution

In accordance with the present invention the protein(s) of interest may be separated and isolated from a protein solution. In the present context the term "protein solution" relates to any kind of solution in liquid form comprising the protein(s) of interest and from which the protein(s) may be separated and isolated. In an embodiment of the present invention the protein solution may be obtained from a source selected from blood, serum, plasma or other blood derived sources. The blood, serum, plasma or other blood derived sources may be obtained from humans or animals such as cows, camel, pig, sheep, goat, rabbit, mouse, rat, horse, zebra, chicken, fish, or ostrich. In an embodiment of the present invention the animal selected may be capable of producing or may have been modified to produce the protein(s) of interest. In an alternative embodiment of the present invention the protein solution may be obtained from a mammalian cell culture or a microbial fermentation broth, where the mammalian cell or the microorganism is capable of or has been modified to produce the protein(s) of interest, or a plant extract, where the plant is capable of producing or has been modified to produce the protein(s) of interest.

In an embodiment of the present invention the protein solution used may be supplemented with an alcohol.

In the present context the term "supplemented with an alcohol" relates to the addition of an alcohol to the protein solution in order to achieve separation of at least two components present in the protein solution whereby one component will become present in a supernatant and the other component will become present in a fraction. In particular such separation of the protein solution involves gradually increasing the amount of alcohol added to the protein solution and thereby separating the at least one serum or plasma protein from the protein solution. In the course of the separation process the protein(s) of interest may be present in either the supernatant or in the fraction. In an embodiment of the present invention the protein solution is supplemented with an alcohol to comprise at least 0.1 vol. % of an alcohol, e.g. at least 0.5 vol. %, such as at least 0.75 vol. %, e.g. at least 1.0 vol. %, such as at least 1.5 vol. %, e.g. at least 2.0 vol. %, such as at least 3.0 vol. %, e.g. at least 5.0 vol. %, such as at least 7.5 vol. %, e.g. at least 10.0 vol. %, such as at least 20 vol. %, e.g. at least 25.0 vol. %, such as at least 40 vol. %, e.g. at least 50.0 vol. %, such as at least 60 vol. %, e.g. at least 75.0 vol. %.

In yet an embodiment of the present invention the protein solution has a total alcohol content of at least 0.1 vol. % of an alcohol, e.g. at least 0.5 vol. %, such as at least 0.75 vol. %, e.g. at least 1.0 vol. %, such as at least 1.5 vol. %, e.g. at least 2.0 vol. %, such as at least 3.0 vol. %, e.g. at least 5.0 vol. %, such as at least 7.5 vol. %, e.g. at least 10.0 vol. %, such as at least 20 vol. %, e.g. at least 25.0 vol. %, such as at least 40 vol. %, e.g. at least 50.0 vol. %, such as at least 60 vol. %, e.g. at least 75.0 vol. %, such as at least 77 vol. %.

In the present context the term "supernatant" relates to a liquid phase, which is lying above a liquid fraction, a sediment fraction or a precipitated fraction obtained by the addition of an alcohol to the protein solution, in accordance with the present invention.

In the present context the term "fraction" relates to a portion of the protein solution, which may be separated from the supernatant by a fractionation process, such as filtration, microfiltration, centrifugation, distillation or chromatography and the fraction may be either a combination of compounds or a pure compound. In an embodiment of the present invention the fraction may be in the form of a liquid (a liquid fraction), a sediment (a sediment fraction) or a precipitate (a precipitated fraction).

In an embodiment of the present invention the protein solution may be supplemented with an alcohol selected from the group consisting of methanol, ethanol, n-propanol, i-propanol, n-butanol, i-butanol, s-butanol, t-butanol, methylene glycol, ethylene glycol, propylene glycol, diethylene glycol, methylene-ethylene glycol, and dimethylene glycol.

In a preferred embodiment of the present invention the protein solution comprises of plasma or serum, in particular from a human. In yet an embodiment of the present invention, the protein solution comprises serum or plasma fraction(s) and/or plasma or serum supernatant(s), in particular from a human.

Furthermore, in an embodiment of the present invention fractions obtained from a resolubilised precipitate, may be obtained by gradual addition of alcohol to the protein solution. In particular a plasma or serum fraction may be provided from a resolubilised precipitate obtained by the addition of alcohol to plasma or serum.

In accordance with the present invention a protein solution may be obtained from the protein solution and may comprise the combination of one or more supernatant(s) and/or one or more resolubilised fractions. In particular a human or animal plasma or serum protein solution may by obtained by recombination of one or more supernatants and/or one or more resolubilised precipitates obtained by the addition of alcohol to human or animal plasma or serum.

In an embodiment of the present invention the temperature of the protein solution may be in the range of −5 to 50° C., more preferably in the range of −5 to 40° C., still more preferably in the range of −5 to 30° C., still more preferably in the range of −5 to 20° C., still more preferably in the range from 0 to 10° C. or in the range of 0 to 50° C., more preferably in the range of 10 to 50° C., still more preferably in the range of 20 to 50° C., still more preferably in the range of 30 to 50° C., still more preferably in the range from 40 to 50° C.

The Fractionation/Separation Method

As mentioned above the conventional way of fractionating protein solutions involves the method described by Cohn et al. which involves stepwise addition of alcohol to the protein solution whereby the protein(s) of interest are gradually separated from the protein solution. This process have been described in more detail in: Cohn et al, "*Separation into Fractions of Protein and Lipoprotein Components*" J. Am. Chem. Soc., 68, 459-475, 1946; E. J. Cohn et al., Preparation and Properties of Serum and Plasma Proteins, IV, A System for the Separation into Fractions of the Protein and Lipoprotein Components of Biological Tissues and Fluids, The Journal of the American Chemical Society, vol. LXVIII (January-July 1946), pp. 459-475; U.S. Pat. No. 2,390,074 and U.S. Pat. No. 2,469,193 which are all incorporated by reference.

In the present context the terms "fractionation" and "separation" are used interchangeably and relates to the process of preparing the protein solution before contacting it with the adsorbent for the isolation of the protein(s) of interest.

In an embodiment of the present invention a stepwise fractionation of protein solutions by the addition of alcohol to obtain protein(s) may be illustrated by one or more or the following operations:

(i) The protein solution, such as plasma may initially be frozen and then subjected to a slow, controlled de-freezing procedure, whereby a cryoprecipitate is formed comprising Factor VIII (complexed with the von Willebrand factor, vWF) and fibrinogen and a supernatant comprising the bulk of the proteins remains in plasma (called cryo-poor plasma).

(ii) The cryoprecipitate fraction obtained in (i) may be resolubilised to form a protein solution and the protein(s) may be isolated by contacting it with an adsorbent. In particular protein(s) such as Factor VIII, vWF and fibrinogen may be isolated from the protein solution obtained from the resolubilised fraction.

(iii) The supernatant from (i), cryo-poor plasma, may be supplemented with alcohol and fraction I (a precipitate) and supernatant I are formed.

(iv) Supernatant I may be supplemented with more alcohol and precipitated fraction II+III and supernatant II+III are formed. Fraction II+III may be separated and resolubilised to form a protein solution and protein(s) of interest may be isolated by contacting is with an adsorbent. In particular protein(s) such as immunoglobulins (such as IgG) may be isolated from the protein solution obtained from fractions II+III. Supernatant II+III will mainly comprise albuman and alpha-1-proteinase inhibitor.

(v) The supernatant II+III may be further supplemented with alcohol and forming supernatant IV-1 and precipitated fraction IV-1. Fraction IV-1 may be separated and resolubilised and form a protein solution and protein(s) may be isolated by contacting is with an adsorbent. In particular plasma protein(s) such as alpha-1-proteinase inhibitor, anti-thrombin III and Factor IX complex may be isolated from the protein solution obtained from fraction IV-1.

(vi) The Supernatant IV-1 may be supplemented with more alcohol to form precipitated fraction IV-4 and supernatant IV-4. Fraction IV-4 may be separated and resolubilised to form a protein solution and the protein(s) of interest may be isolated by contacting is with an adsorbent. In particular Butyrylcholinesterase may be isolated from the protein solution obtained from fraction IV-4.

(vii) Supernatant VI-4 may be further supplemented with alcohol to provide precipitated fraction V which may be separated and resolubilised to form a protein solution and protein(s) of interest may be isolated by contacting is with an adsorbent. In particular albumin may be isolated from the protein solution obtained from fraction V.

In an embodiment of the present invention the protein solution, may be selected from the group consisting of cryo-poor plasma, supernatant I, supernatant II+III, supernatant IV-1, supernatant IV-4, resolubilised cryo-precipitate, resolubilised fraction I, resolubilised fraction II+III, resolubilised fraction IV-1, resolubilised fraction IV-4, resolubilised fraction V and any combination thereof.

In a particular embodiment of the present invention the protein solution may be selected from the group consisting of supernatant I, supernatant II+III, resolubilised fraction IV-1, and any combination thereof.

In yet a particular embodiment of the present invention the protein solution may be selected from the group consisting of supernatant I, supernatant II+III, supernatant I+II+III, and resolubilised fraction IV-1 and any combination thereof.

In a further particular embodiment of the present invention the protein solution may be selected from the group of supernatant I and resolubilised fraction II+III.

The precipitated fractions may be resolubilised in a broad range of aqueous solutions including pure water. In many preferred embodiments the resolubilisation medium will be an aqueous buffer having a pH and ionic strength suitable for the following downstream processing step e.g. an adsorption step according to the invention.

In an embodiment of the present invention precipitated fractions may be obtained from a supernatant by filtration, centrifugation, decantation, ultrafiltration and/or sedimentation.

In an embodiment of the present invention the protein solution may be obtained by the Cohn fractionation method as described by Cohn et al, "*Separation into Fractions of Protein and Lipoprotein Components*" J. Am. Chem. Soc., 68, 459-475, 1946; E. J. Cohn et al., Preparation and Properties of Serum and Plasma Proteins, IV, A System for the Separation into Fractions of the Protein and Lipoprotein Components of Biological Tissues and Fluids, The Journal of the American Chemical Society, vol. LXVIII (January-July 1946), pp. 459-475; U.S. Pat. No. 2,390,074 and U.S. Pat. No. 2,469.193.

In an embodiment of the present invention the protein solution comprises at least one plasma or serum protein obtained from the fractionation of plasma or serum by addition of ethanol, e.g. the original Cohn fractionation process or variants hereof such as the Cohn-Oncley process.

The Protein

In a preferred embodiment of the present invention the protein(s) to be isolated is a blood protein, such as a plasma protein or a serum protein. In the present context the term "plasma or serum protein(s)" relates to protein(s) which is/are produced or required by the human or animal body. Normally these plasma or serum proteins are contained in the blood of humans or animals and particularly some of these proteins are originally found in the red blood cells whereas others are found in solution in the plasma or serum.

Plasma is a component of blood. It is the liquid in which blood cells are suspended. Blood plasma contains proteins, lipids, nutrients, metabolic end products, hormones, and inorganic electrolytes. Blood plasma is typically stabilised by the addition of anti-coagulants such as sodium citrate, heparin and EDTA.

Serum is the same as blood plasma except that clotting factors (such as fibrinogen and Factor VIII) have been removed.

In an embodiment of the present invention the plasma or serum protein is a human or animal plasma or serum protein.

In an embodiment of the present invention the one or more plasma or serum protein(s) to be isolated is/are selected from the group consisting of albumin, IgG, IgA, IgM, IgD, IgE, alpha-1-proteinase inhibitor (same as $\alpha$-1-antitrypsin), blood pro-coagulation protein, blood anti-coagulation protein, thrombolytic agent, anti-angiogenic protein, $\alpha$-2-antiplasmin, C-1 esterase inhibitor, apolipoprotein, HDL, LDL, Fibronectin, beta-2-glycoprotein I, fibrinogen, plasminogen, plasmin, plasminogen activator, plasminogen inhibitor, plasma protease inhibitor, anti-thrombin III, streptokinase, inter-alpha-trypsin inhibitor, $\alpha$-2-macroglobulin, amyloid protein, ferritin, pre-albumin, GC-globulin, haemopexin, C3-complement, transferrin, urokinase, $\alpha$-1-acid-glycoprotein, and the coagulation or anti-coagulation factor(s) such as Factor II, Factor V, Factor VII, Factor VIII, von Willebrand factor, Factor VIII—von Willebrand factor complex, Factor IX, Factor X, Factor XI, C1 inhibitor, protein C and/or Protein S.

The Column

The adsorbent capable of capturing the one or more protein(s) may be held within a column or it may not be held within a column. In the present context the term "column" relates to any kind of container which can be supplied with at least one inlet and at least one outlet for the application of the protein solution to the column and subsequent to elute the protein. The inlet and the outlet may for certain columns be the same (e.g. for batch adsorption tanks). The column may be in the form of an Expanded bed adsorption (EBA) column, packed bed column, a fluidized bed adsorption column, a suspended bed adsorption column, membrane reactor, or a batch adsorption tank. The adsorbent column may be used in either a batch system or in a continuous system. Typically packed bed columns and expanded bed adsorption columns operate under plug flow conditions (i.e. no liquid back-mixing and turbulence in the adsorbent bed), while suspended bed columns and batch adsorption tanks operate with a high degree of mixing at least in the major part of the column volume.

The fact that the EBA technology generally can work efficiently with non-clarified protein solution makes it attractive for the isolation of proteins. Compared to processes based on packed bed adsorption techniques EBA may offer a robust process comprising fewer steps and thus result in increased yields and an improved process economy. Due to the expansion of the adsorbent bed during execution of an EBA process, EBA columns may further be scaled up to industrial scale without any significant considerations regarding increased back pressures or breakdown of the process due to clogging of the system which often is a problem when using packed bed columns.

In accordance with the present invention the protein solution is applied to a packed bed column or an expanded bed column comprising an adsorbent.

In the present context the term "packed bed" relates to embodiments wherein the adsorbent particles are employed in columns operating with the particles in a sedimented or packed state wherein all particles are fixed on top of each other. Often packed bed columns are equipped with top and bottom adaptors defining and fixing the whole adsorbent bed to avoid any movement of the particle during operation.

In the present context the term "expanded bed" relates to embodiments wherein the adsorbent particles are employed in columns allowing the adsorbent to expand with an upward liquid flow through the column. The column will be designed to avoid excessive liquid mixing and turbulence in the column while the individual adsorbent particles are kept in a non-fixed, dynamic state moving only in a narrow local zone in the column. While preferred expanded beds have a small mixing zone in the bottom part of the column where incoming liquid is distributed throughout the cross-section of the column, expanded beds generally operate under plug flow conditions in similarity with packed beds.

In an embodiment of the present invention the adsorbent is held in an Expanded bed adsorption column and preferably used for the large-scale isolation of one or more protein(s) from a protein solution.

In the case where the adsorbent is not held within a column it may be a solid phase, such as for membrane based adsorption, e.g. a membrane filter, fibers or sheets, whereto the ligand is coupled.

Whenever the adsorbent is in the form of permeable or semi-permeable membranes, fibres or sheets the contacting between the adsorbent and the protein solution may generally be performed by pumping/forcing the protein solution across the surface and/or through a porous structure of the membrane or sheet to ensure that the one or more plasma or serum protein may be coming in close contact with the covalently attached functional groups on the surface and/or in the adsorbents.

The Adsorbent

It is a further object of this invention to provide a process for isolation of protein(s) from a protein solution based on adsorption to any type of solid phase material of any shape and format including packed bed adsorption, batch adsorption, suspended bed adsorption, Expanded bed adsorption (EBA), fluidised bed adsorption and membrane based adsorption. Furthermore, the adsorption may be characterised by the use of selective adsorbent characteristics and/or ligand chemistry enabling the specific binding and subsequent elution of substantially only one biomolecular substance, or alternatively enabling a group specific binding of a few biomolecular substances followed by selective and consecutive elution of one or more substances from the adsorbent.

The adsorbent comprises a ligand suitable for binding to the one or more protein(s) of interest. In an embodiment of the present invention the adsorbent may optionally be washed and/or equilibrated with one or more washing buffer and/or equilibration buffers.

For a broad range of preferred embodiments of the present invention it is of critical importance that the adsorbent is a particle having combined characteristics in terms of size and density. It has thus been found that for highly concentrated protein solutions such as plasma or serum it is highly desirable to employ particles having a volume mean particle diameter of less than 150 µm in order to obtain a fast and efficient protein-binding (which is important for the productivity and thus the economy of a production plant). However it has further been found that it is the combination of the small diameter of the adsorbent particles (below 150 µm) with a certain minimum density (more than 1.5 g/ml)) of the adsorbent particles that enables significant improvements in production plant productivity. Hereby a unique combination of fast and efficient protein binding with high liquid flow rates through the columns employed for the adsorption process may be achieved. Particularly for non-packed columns such as e.g. expanded bed columns and suspended bed columns the high liquid flow rates obtainable with the adsorbents according to the invention may be significant. For packed bed columns it may be a distinct advantage that the small adsorbent particles have a high density providing fast sedimentation during the packing and re-packing procedure, which otherwise is a slow and demanding process step. Generally it is found that a smaller mean volume diameter of the particles may desire a higher density of the particles.

Examples of commercial adsorbent particles that may be employed for some of the embodiments of the present invention are:

FastLine UFC NNSDW, UpFront Chromatography A/S, Denmark having a volume mean particles diameter of 70 µm and a density of 2.9 g/ml.

STREAMLINE SP, Amersham Biosciences, Sweden, having a volume mean particle diameter of 200 µm and a density of 1.2 g/ml.

STREAMLINE Direct CST-1, Amersham Biosciences, Sweden having a volume mean particle diameter of 135 µm and a density of 1.8 g/ml.

Q and CM HyperZ Ion exchange sorbents, Biosepra SA, France, having a volume mean particle diameter of 75 µm and a density of 3.2 g/ml.

Specifically in expanded bed adsorption the flow rate, the size of the particles and the density of the particles may all have influence on the expansion of the expanded bed and it is important to control the degree of expansion in such a way to keep the particles inside the column when working with Expanded bed adsorption. For industrial applicability it may be of interest to have a high flow-rate and a low expansion. The degree of expansion may be determined as H/H0, where H0 is the height of the bed in packed bed mode (without flow through the column) and H is the height of the bed in expanded mode (with a given flow through the column). In an embodiment of the present invention the degree of expansion H/H0 is in the range of 1.1-6, such as 1.1-5, e.g. 1.1-4, such as 1.2-5, e.g. 1.5-4 such as 2-4, such as, such as 2-3, such as 3-4. In another embodiment of the present invention the degree of expansion H/H0 is at most 1.2, e.g. at the most 1.3, such as at most 1.5, e.g. at most 1.8 such as at most 2, such as at most 2.5, e.g. at lmost 3, such as at most 3.5, e.g. at 4, such as at most 4.5. In yet an embodiment of the present invention the flow-rate is 5 cm/min and the degree of expansion H/H0 is at most 1.2, e.g. at the most 1.3, such as at most 1.5, e.g. at most 1.8 such as at most 2, such as at most 2.5, e.g. at lmost 3, such as at most 3.5, e.g. at 4, such as at most 4.5. In a further embodiment of the present invention the flow-rate is 7 cm/min and the degree of expansion H/H0 is at most 1.2, e.g. at the most 1.3, such as at most 1.5, e.g. at most 1.8 such as at most 2, such as at most 2.5, e.g. at most 3, such as at most 3.5, e.g. at 4, such as at most 4.5. In still an embodiment of the present invention the flow-rate is 10 cm/min and the degree of expansion H/H0 is at most 1.2, e.g. at the most 1.3, such as at most 1.5, e.g. at most 1.8 such as at most 2, such as at most 2.5, e.g. at lmost 3, such as at most 3.5, e.g. at 4, such as at most 4.5. In yet an embodiment of the present invention the flow-rate is 15 cm/min and the degree of expansion H/H0 is at most 1.2, e.g. at the most 1.3, such as at most 1.5, e.g. at most 1.8 such as at most 2, such as at most 2.5, e.g. at lmost 3, such as at most 3.5, e.g. at 4, such as at most 4.5. In still an embodiment of the present invention the flow-rate is 20 cm/min and the degree of expansion H/H0 is at most 1.2, e.g. at the most 1.3, such as at most 1.5, e.g. at most 1.8 such as at most 2, such as at most 2.5, e.g. at lmost 3, such as at most 3.5, e.g. at 4, such as at most 4.5.

In an embodiment of the present invention the linear flow rate of the packed bed column or the expanded bed column may be at least 2 cm/min, more preferably at least 3 cm/min, still more preferably at least 4 cm/min, still more preferably at least 5 cm/min, still more preferably at least 6 cm/min, still more preferably at least 7 cm/min, still more preferably at least 8 cm/min, still more preferably at least 10 cm/min, still more preferably at least 12 cm/min, still more preferably at least 15 cm/min, still more preferably at least 20 cm/min, still more preferably at least 25 cm/min, still more preferably at least 30 cm/min, still more preferably at least 40 cm/min, still more preferably at least 50 cm/min. In yet an embodiment of the present invention the linear flow rate is in the range of 1-75 cm/min, such as 2-75 cm/min, e.g. 5-75 cm/min, such as 7-75 cm/min, e.g. 10-75 cm/min, such as 15-75 cm/min, e.g. 20-75 cm/min, such as 30-75 cm/min, e.g. 40-75 cm/min, such as 50-75 cm/min, e.g. 1-50 cm/min, such as 2-50 cm/min, e.g. 2-30 cm/min, such as 3-30 cm/min, such as 3-20 cm/min, such as 3-15 cm/min, such as 4-30 cm/min, such as 4-25 cm/min, such as 4-20 cm/min, such as 4-15 cm/min, such as 5-25 cm/min, e.g. 5-15 cm/min, such as 5-10 cm/min, e.g. 5-7.5 cm/min, such as 7.5 cm/min. These increased flow rates, compared to conventional used flow rates (in particular for packed bed columns), may be possible to a great extent due to the small particle diameter in combination with the high density of the adsorbent.

In a particular embodiments of the present invention the application of protein solution to the adsorbent column may be performed with a linear flow rate of at least 200 cm/hour, such as at least 300 cm/hour, more preferably at least 400 cm/hour, such as at least 500 or 600 cm/hour, such as at least 900 cm/hour.

In an embodiment of the present invention the column may comprise a high-density adsorbent. In the present context the term "high-density adsorbent" relates to part of the group of adsorbents and involves the entire bed of adsorbent particles present in the adsorbent column. The term "adsorbent particle" are used interchangeably with the term "particle" and relates to the individual single particles which makes up the adsorbent in the column. The preferred shape of a single adsorbent particle is substantially spherical. The overall shape of the particles is, however, normally not extremely critical, thus, the particles can have other types of rounded shapes, e.g. ellipsoid, droplet and bean forms. However, for certain applications (e.g. when the particles are used in a fluidised bed setup), it may be preferred that at least 95% of the particles are substantially spherical. In the present context the terms "particle diameter" and "particle size" are used interchangeable and relates to the diameter of a circle which may be made around the particle and therefore, may be regarded as the diameter of the particle on the widest part of the particle.

The density of an adsorbent particle is meant to describe the density of the adsorbent particle in its fully solvated (e.g. hydrated) state as opposed to the density of a dried adsorbent. In the present invention the density of the particle may be measured by performing the following procedure: 1) Draining a sample of the adsorbent particles by gentle suction on a vacuum glass filter to remove the interstitial water occupying the space between the individual beads. 2) Weighing the drained particle sample to determine the total mass of the particles. 3) Adding the entire amount of drained particle sample to a known amount of water in a measuring cylinder and reading out the increase in total volume obtained by the addition of the drained particles. 4) Calculating the density by dividing the total mass of the drained particles with the volume increase determined under Item 3.

In an embodiment of the present invention the density of the adsorbent particle may be in the range of 1.5 g/ml to 20 g/ml, more preferably in the range from 1.9-20, more preferably in the range from 2.0 g/ml to 20 g/ml, more preferably in the range from 2.1 g/ml to 20 g/ml, more preferably in the range from 2.3 g/ml to 20 g/ml, even more preferably in the range of 2.5 g/ml to 20 g/ml, even more preferably in the range of 2.8 g/ml to 20 g/ml, e.g. in the range of 2.9 g/ml to 20 g/ml, still more preferably in the range of 3.0 g/ml to 20 g/ml, still more preferably in the range of 3.5 g/ml to 20 g/ml, still more preferably in the range of 4 g/ml to 20 g/ml, still more preferably in the range of 5 g/ml to 20 g/ml, still more preferably in the range of 10 g/ml to 20 g/ml, still more preferably in the range of 15 g/ml to 20 g/ml, still more preferably in the range of 4 g/ml to 15 g/ml, still more preferably in the range of 4 g/ml to 10 g/ml, still more preferably in the range of 1.5 g/ml to 15 g/ml.

The density of the EBA adsorbent particle may be significant for the applicable flow rates in relation to the maximal degree of expansion of the adsorbent bed possible inside a typical EBA column (e.g. H/H0 max 3-5) and may be at least 1.3 g/mL, more preferably at least 1.5 g/mL, still more preferably at least 1.8 g/mL, still more preferably at least 1.9 g/mL, even more preferably at least 2.0 g/mL, still more preferably at least 2.1 g/mL, most preferably at least 2.3 g/mL, even more preferably at least 2.5 g/ml, even more preferably at least 2.8 g/ml, even more preferably at least 2.9 g/ml, still more preferably at least 3.0 g/ml, still more preferably at least 3.5 g/ml in order to enable a high productivity of the process.

In yet an embodiment of the present invention 85% by volume of the individual particles of the adsorbent have a diameter within the range of 5 to 200 micron (µm), more preferably within the range of 10 to 150 micron, still more preferably within the range of 15 to 120 micron, still more preferably within the range of 20 to 100 micron, still more preferably within the range of 20 to 80 micron, still more preferably within the range of 80 to 150 micron, and even still more preferably within the range of 40 to 120 micron. In yet an embodiment of the present invention the mean particle diameter of the adsorbent may be 150 micron or less, preferably 120 micron or less, even more preferably 100 micron or less, still more preferably 80 micron or less, still more preferably 70 micron or less, still more preferably 60 micron or less, still more preferably 50 micron or less, still more preferably 40 micron or less.

Several parameters having an influence on the flow rate can be implemented in an EBA process. The fluidisation properties of the adsorbent particles (which may be described by the aid of Stokes Law) determine which flow rates that may be applied in order to expand the adsorbent and still keep the adsorbent inside the column. The main factors influencing this are the diameter and the density of the adsorbent particles in combination with the viscosity of the liquid flowing through the column. However, the binding and mass transfer kinetics relevant to a specific application are equally important to ensure optimal efficiency and productivity of the EBA process. For example, it may be possible to run an EBA column containing a certain EBA adsorbent at very high flow rates in terms of the physical fluidisation and expansion properties, while the applied high flow rate results in a poor and inefficient adsorption (i.e. a low dynamic capacity) due to the fact that the target molecules to be bound cannot diffuse in and out of the adsorbent particles to match this flow rate (i.e. the mass transfer kinetics is the limiting factor).

Consequently, in a combination of particularly preferred embodiments of the invention, where the applied linear flow rate during application of the protein solution is above 300 cm/hour, the mean volume particle diameter is 150 μm or less. Typically, in embodiments where the fractionation process is performed at an applied linear flow rate of above 500 cm/min, the mean volume particle diameter is below 120 μm, preferably below 90 μm. Typically, in embodiments where the fractionation process is performed at an applied linear flow rate of above 600 cm/hour, the mean volume particle diameter is preferably below 85 μm, more preferably below 75 μm.

Fundamentally the expression of particle size distribution in this context is volume based on the general understanding in the technical field and as described by Malvern Instruments Ltd (Worcestershire, UK) in their Operators guide (MAN 0320 Issue 1.0 March 2004) to the Mastersizer 2000E, which describes the measurement of particle size distribution by the aid of light scattering.

This means that, when the result indicates, for example, that 11% of a distribution is in the size category 65-78 μm, this means that the total volume of all particles with diameters in that range (within the size category 65-78) represents 11% of the total volume of all the particles in the distribution. The mean volume diameter (or volume mean diameter) referred to in the present context relates to the volume mean diameter labelled "D(4,3)" by Malvern for the Mastersizer 2000E. Whenever a particle size range is referred to such as "the particles have a particle diameter in the range of X-Y μm" it is meant to be understood as at least 90% of the total volume of particles have a diameter in the range of X-Y μm, such as at least 95%, e.g. at least 98%, such as at least 99%.

In still an embodiment of the present invention the adsorbent density, particle diameter and the mean volume particle diameter as described above may be combined in any way possible to provide the most suitable adsorbent for the isolation of the one or more protein(s) of interest. In an embodiment of the present invention the density of the adsorbent may be in the range of 1.5 to 10.0, 85% by volume of the individual particles of the adsorbent may have a diameter within the range of 10 to 150 micron, and the mean volume particle diameter may be in the range of 15 to 100 micron. In another embodiment of the present invention the density of the adsorbent may be in the range of 2.0 to 5.0, 85% by volume of the individual particles of the adsorbent may have a diameter within the range of 20 to 140 micron, and the mean volume particle diameter may be in the range of 55 to 85 micron. In yet an embodiment of the present invention the density of the adsorbent may be in the range of 2.5 to 3.5, 85% by volume of the individual particles of the adsorbent may have a diameter within the range of 40 to 120 micron, and the mean volume particle diameter may be in the range of 60 to 80 micron.

In a combination of preferred embodiments, where the mean volume particle diameter may be 120 μm or less, the particle density is at least 1.6 g/mL, more preferably at least 1.9 g/mL. When the mean volume particle diameter is less than 90 μm the density must be at least 1.8 g/mL or more preferable at least 2.0 g/mL. When the mean volume particle diameter is less than 75 μm the density must be at least 2.0 g/mL, more preferable at least 2.3 g/mL and most preferable at least 2.5 g/mL.

In en embodiment of the present invention the adsorbent particle comprises a particle having a mean volume particle diameter of at the most 150 μm and a particle density of at least 1.5 g/ml; such as a particle density of at least 1.6 g/ml; e.g. a particle density of at least 1.9 g/ml; such as a particle density of at least 2.0 g/ml; e.g. a particle density of at least 2.3 g/ml; such as a particle density of at least 2.5 g/ml; e.g. a particle density of at least 2.8; e.g. a particle density of at least 3.0 g/ml; such as a particle density of at least 3.5 g/ml; e.g. a particle density of at least 4.0 g/ml; such as a particle density of at least 4.5 g/ml. Preferably, the adsorbent particle comprises a particle having a mean volume particle diameter of at the most 120 μm and a particle density of at least 1.5 g/ml; such as a particle density of at least 1.6 g/ml; e.g. a particle density of at least 1.9 g/ml; such as a particle density of at least 2.0 g/ml; e.g. a particle density of at least 2.3 g/ml; such as a particle density of at least 2.5 g/ml; e.g. a particle density of at least 2.8; e.g. a particle density of at least 3.0 g/ml; such as a particle density of at least 3.5 g/ml; e.g. a particle density of at least 4.0 g/ml; such as a particle density of at least 4.5 g/ml. More preferably, the adsorbent particle comprises a particle having a mean volume particle diameter of at the most 100 μm and a particle density of at least 1.5 g/ml; such as a particle density of at least 1.6 g/ml; e.g. a particle density of at least 1.9 g/ml; such as a particle density of at least 2.0 g/ml; e.g. a particle density of at least 2.3 g/ml; such as a particle density of at least 2.5 g/ml; e.g. a particle density of at least 2.8; e.g. a particle density of at least 3.0 g/ml; such as a particle density of at least 3.5 g/ml; e.g. a particle density of at least 4.0 g/ml; such as a particle density of at least 4.5 g/ml. Even more preferably, the adsorbent particle comprises a particle having a mean volume particle diameter of at the most 90 μm and a particle density of at least 1.5 g/ml; such as a particle density of at least 1.6 g/ml; e.g. a particle density of at least 1.9 g/ml; such as a particle density of at least 2.0 g/ml; e.g. a particle density of at least 2.3 g/ml; such as a particle density of at least 2.5 g/ml; e.g. a particle density of at least 2.8; e.g. a particle density of at least 3.0 g/ml; such as a particle density of at least 3.5 g/ml; e.g. a particle density of at least 4.0 g/ml; such as a particle density of at least 4.5 g/ml. Even more preferably, the adsorbent particle comprises a particle having a mean volume particle diameter of at the most 75 μm and a particle density of at least 1.5 g/ml; such as a particle density of at least 1.6 g/ml; e.g. a particle density of at least 1.9 g/ml; such as a particle density of at least 2.0 g/ml; e.g. a particle density of at least 2.3 g/ml; such as a particle density of at least 2.5 g/ml; e.g. a particle density of at least 2.8; e.g. a particle density of at least 3.0 g/ml; such as a particle density of at least 3.5 g/ml; e.g. a particle density of at least 4.0 g/ml; such as a particle density of at least 4.5 g/ml. Even more preferably, the adsorbent particle comprises a particle having a mean volume particle diameter of at the most 50 μm and a particle density of at least 1.5 g/ml; such as a particle density of at least 1.6 g/ml; e.g. a particle density of at least 1.9 g/ml; such as a particle density of at least 2.0 g/ml; e.g. a particle density of at least 2.3 g/ml; such as a particle density of at least 2.5 g/ml; e.g. a particle density of at least 2.8; e.g. a particle density of at least 3.0 g/ml; such as a particle density of at least 3.5 g/ml; e.g. a particle density of at least 4.0 g/ml; such as a particle density of at least 4.5 g/ml. Even more preferably, the adsorbent particle comprises a particle having a mean volume particle diameter of at the most 40 μm and a particle density of at least 1.5 g/ml; such as a particle density of at least 1.6 g/ml; e.g. a particle density of at least 1.9 g/ml; such as a particle density of at least 2.0 g/ml; e.g. a particle density of at least 2.3 g/ml; such as a particle density of at least 2.5 g/ml; e.g. a particle density of at least 2.8; e.g. a particle density of at least 3.0 g/ml; such as a particle density of at least 3.5 g/ml; e.g. a particle density of at least 4.0 g/ml; such as a particle density of at least 4.5 g/ml.

The adsorbent particle used according to the invention must be at least partly permeable to the biomolecular substance to be isolated in order to ensure a significant binding capacity in contrast to impermeable particles that can only bind the target molecule on its surface resulting in relatively low binding capacity. The adsorbent particle may be of an array of different structures, compositions and shapes.

The high density of the adsorbent particle is, to a great extent, achieved by inclusion in a porous polymer phase, of a certain proportion of a dense non-porous core material. The non-porous core preferably has a density of at least 4.0 g/mL, such as at least 5.0 g/mL, e.g. at least 8.0 g/mL, such as at least 10 g/mL, e.g. at least 15 g/mL. Typically, the non-porous core material has a density in the range of about 4.0-25 g/ml, such as about 4.0-20 g/ml, e.g. about 4.0-15 g/mL, such as 12-19 g/ml, e.g. 14-18 g/ml, such as about 6.0-15.0 g/mL, e.g. about 6.0-10 g/ml.

Other types of high density adsorbent particles are based on particles made out of a porous high density material, such as zirconium oxide, in which pores ligands for adsorption may be immobilised either directly to the high density material or to porous polymer networks filled into the pores of the high density material, see e.g. U.S. Pat. No. 6,036,861 and WO 99/51316. Although being an attractive way of providing a high density and small adsorbent particle such types of adsorbents will generally have some draw backs due to diffusion restriction in the porous structure and a high volume content of the high density phase resulting in low accessible protein binding volumes It is of central importance to a broad range of preferred embodiments of the invention that the adsorbent particle employed according to the invention has a high accessible protein binding volume. In the present context the term "particle accessible protein binding volume" relates to the relative pore volume of any specific particle type and is expressed as volume percent relative to the volume of the entire bead (i.e. the volume occupied by pores/the total volume of the bead×100%). Thus if too much of the particle volume is occupied by the high density material only low column productivities can be achieved.

In an embodiment of the present invention the particle accessible protein binding volume of the adsorbent may be at least 20%, more preferably at least 30%, still more preferably at least 40%, still more preferably at least 50%, still more preferably at least 55%, still more preferably at least 60%, still more preferably at least 65%, still more preferably at least 70%, still more preferably at least 75%, still more preferably at least 80%, still more preferably at least 85% and still more preferably at least 90%.

In an embodiment of the present invention the adsorbent may have a dynamic binding capacity at 10% break-through for said at least one specific protein of at least 5 g per litre sedimented adsorbent, more preferably at least 10 g per litre, even more preferably at least 15 g per litre, still more preferably at least 20 g per litre, still more preferably at least 25 g per litre, still more preferably at least 30 g per litre, still more preferably at least 35 g per litre, still more preferably at least 40 g per litre, still more preferably at least 50 g/litre, still more preferably at least 60 g/litre.

When the protein solution is added to the adsorbent column the ratio between the adsorbent particle present in the column and the protein solution may be optimized in order to retain a high capacity of the adsorbent and to obtain a high purity of the protein or proteins to be isolated. In a preferred embodiment of the present invention the adsorbent present in the column relative to the protein solution to be loaded on to the column are provided at a ratio of at least 1:100, such as at least 1:50, e.g. at least 1:30, such as at least 1:15, e.g. 1:10, such as 1:5, such as 1:1, such as 1:0,5 measured on a volume/volume basis.

Thus, the adsorbent particles may be constituted by a number of chemically derivatised porous materials having the necessary density, diameter and/or binding capacity to operate at the given flow rates per se. The particles are either of the conglomerate type, as described in WO 92/00799, having at least two non-porous cores surrounded by a porous material, or of the pellicular type having a single non-porous core surrounded by a porous material.

In the present context the term "conglomerate type" relates to a particle of a particulate material, which comprises beads of core material of different types and sizes, held together by the polymeric base matrix, e.g. an core particle consisting of two or more high density particles held together by a surrounding polymeric base matrix (e.g. agarose).

In the present context the term "pellicular type" relates to a composite of particles, wherein each particle consists of only one high density core material coated with a layer of the porous polymeric base matrix, e.g. a high density stainless steel bead coated with agarose.

Accordingly the term "at least one high density non-porous core" relates to either a pellicular core, comprising a single high density non-porous particle or it relates to a conglomerate core comprising more that one high density non-porous particle.

The adsorbent particle, as stated, may comprise a high density non-porous core with a porous material surrounding the core, and said porous material optionally comprising a ligand at its outer surface.

In the present context the term "core" relates to the non-porous core particle or core particles which are present inside the adsorbent particle. The core particle or core particles may be incidental distributed within the porous material and is not limited to be located in the centre of the adsorbent particle.

The non-porous core constitutes typically of at most 70% of the total volume of the adsorbent particle, such as at most 60%, preferably at most 50%, preferably at most 40%, preferably at most 30%, preferably at most 20%, preferably at most 15%, preferably at most 10% preferably at most 5%.

Examples of suitable non-porous core materials are inorganic compounds, metals, heavy metals, elementary non-metals, metal oxides, non metal oxides, metal salts and metal alloys, etc. as long as the density criteria above are fulfilled. Examples of such core materials are metal silicates metal borosilicates; ceramics including titanium diboride, titanium carbide, zirconium diboride, zirconium carbide, tungsten carbide, silicon carbide, aluminum nitride, silicon nitride, titanium nitride, yttrium oxide, silicon metal powder, and molybdenum disilide; metal oxides and sulfides, including magnesium, aluminum, titanium, vanadium, chromium, zirconium, hafnium, manganese, iron, cobalt, nickel, copper and silver oxide; non-metal oxides; metal salts, including barium sulfate; metallic elements, including tungsten, zirconium, titanium, hafnium, vanadium, chromium, manganese, iron, cobalt, nickel, indium, copper, silver, gold, palladium, platinum, ruthenium, osmium, rhodium and iridium, and alloys of metallic elements, such as alloys formed between said metallic elements, e.g. stainless steel; crystalline and amorphous forms of carbon, including graphite, carbon black and charcoal. Preferred non-porous core materials are tungsten carbide, tungsten, steel and titanium beads such as stainless steel beads.

The porous material is a polymeric base matrix used as a means for covering and keeping multiple (or a single) core materials together and within the adsorbent particle and as a means for binding the adsorbing ligand.

The polymeric base matrix may be sought among certain types of natural or synthetic organic polymers, typically selected from i) natural and synthetic polysaccharides and other carbohydrate based polymers, including agar, alginate, carrageenan, guar gum, gum arabic, gum ghatti, gum tragacanth, karaya gum, locust bean gum, xanthan gum, agaroses, celluloses, pectins, mucins, dextrans, starches, heparins, chitosans, hydroxy starches, hydroxypropyl starches, carboxymethyl starches, hydroxyethyl celluloses, hydroxypropyl celluloses, and carboxymethyl celluloses; ii) synthetic organic polymers and monomers resulting in polymers, including acrylic polymers, polyamides, polyimides, polyesters, polyethers, polymeric vinyl compounds, polyalkenes, and substituted derivatives thereof, as well as copolymers comprising more than one such polymer functionally, and substituted derivatives thereof; and iii) mixture thereof.

A preferred group of polymeric base matrices are polysaccharides such as agarose.

The investigators of the present invention have found that in order to ensure an efficient adsorption at high flow rates it is necessary to minimise the mean volume particle diameter of the adsorbent particle. Thus, in a preferred embodiment of the present invention the adsorbent particle has a mean volume particle diameter of at the most 150 µm, typically a mean volume particle diameter in the range of about 40 µm to 150 µm. The adsorbent particle typically has a mean volume particle diameter of at most 120 µm, particularly at most 100 µm, more preferably at most 90 µm, 80 µm or 75 µm, more preferably at 70 µm and most preferably at most 60 µm.

From a productivity point of view it is important that the adsorbent is able to bind a high amount of the biomolecular substance per volume unit of the adsorbent. Thus we have found that it is preferable to apply adsorbents having a polymeric phase (i.e. the permeable polymeric network where a ligand is positioned and whereto the actual adsorption is taking place) which constitutes at least 50% of the adsorbent particle volume, preferably at least 70%, more preferably at least 80% and most preferably at least 90% of the volume of the adsorbent particles.

The Ligand

The isolation process of the one or more protein(s) may be provided and facilitated by attaching a suitable ligand to the adsorbent. In an embodiment of the present invention the adsorbent comprises a functionalised matrix polymer carrying a plurality of ligands comprising covalently attached functional groups. In a preferred embodiment of the present invention the ligand comprises an aromatic or heteroaromatic ring-system and one or more acidic groups.

In the present context the term "functionalised matrix polymer" relates to the anchoring site for the ligand promoting the desired protein adsorption characteristics. Depending on the adsorbent particle structure the matrix polymer may form the backbone or skeleton defining the physical shape of the adsorbent particle or it may be a polymer that is occupying the pores of another material that serve as the particle backbone or skeleton. In preferred embodiments the functionalised matrix polymer is a synthetic or natural organic polymer, such as a polysaccharide (e.g. poly-acrylic polymers, agarose or cellulose), or it may be an inorganic polymer, such as silica. In special cases the matrix polymer itself may constitute the protein adsorption site in which case it in not necessary to immobilise further ligands onto the polymer.

In an embodiment of the present invention the adsorbent comprises a functionalised matrix polymer carrying a plurality of covalently attached functional groups, said groups having the general formula:

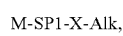

M-SP1-X-Alk, wherein M designates the adsorbent polymer; SP1 designates an optional spacer optionally substituted with -A-SP2-ACID, -A, or -ACID; X designates —O—, —S—, —NH—, or —NAlk-; Alk may be absent, -A-SP2-ACID, -A, -ACID or $C_{1-4}$ alkyl, where $C_{1-4}$ alkyl may be optionally substituted with -A-SP2-ACID, -A, or -ACID; A designates an optionally substituted aromatic or heteroaromatic moiety; SP2 designates an optional spacer; and ACID designates one or more acidic groups; wherein at least one of SP1 or Alk is substituted with -A-SP2-ACID or -A, and at least one of SP1 or Alk comprise -ACID and wherein at least one of SP1 or Alk is present. If Alk is absent, X will also be absent.

In an embodiment of the present invention the adsorbent may be coupled with a ligand carrying a positive charge at pH value at pH 10 or lower, such as pH 9 or lower, e.g. pH 8 or lower, such as pH 7 or lower, e.g. pH 6 or lower, such as pH 5 or lower, e.g. pH 4 or lower.

Further is has been found that the functional groups should not be too large in size and complexity in order to obtain a high binding capacity and a high chemical stability of the adsorbent. Thus it has been found that a larger size in terms of molecular weight and number of ring-systems present in the functional group in many instances only increase the cost of the adsorbent without giving the benefit of a higher binding capacity in terms of the amount of protein that can be bound per litre adsorbent. Also the molar concentration of the covalently attached functional group achievable on the adsorbent may be lower if a large molecular size of the functional group is employed (presumably due to steric hindrance).

Thus, in an embodiment of the invention the covalently attached functional groups comprise a maximum of three mono- or bicyclic aromatic or heteroaromatic ring-systems for each functional group attached to the matrix polymer, more preferably a maximum of two mono- or bicyclic aromatic or heteroaromatic ring-systems and even more preferably a maximum of one mono- or bicyclic aromatic or heteroaromatic ring-systems for each functional group attached to the matrix polymer. Likewise, in an embodiment of the invention the covalently attached functional groups comprise a maximum of three acidic groups, preferably a maximum of 2 acidic groups and most preferably a maximum of one acidic group attached to each aromatic or heteroaromatic ring-system present in the covalently attached functional groups.

In a preferred embodiment of the invention the one or more acidic groups are chosen from the group of carboxylic acids, sulfonic acids, phosphonic acids, boronic acids and combinations hereof.

In an embodiment of the present invention the ligand may be derived from a diethylaminoethyl group, a polyalkylene imine, an alkyl-amine, an alkyl-diamine or a polyallylamine. Preferably, alkyl-amine or alkyl-diamine having a chain-length of 3-14 atoms and 1-5 functional amine groups may be suitable. Atoms to form part of the chain may involve C (carbon), N (nitrogen), O (oxygen) and/or S (sulfur).

In yet an embodiment of the present invention the adsorbent may comprise a ligand, having both aromatic groups and amino groups such as an aromatic amine or an aromatic diamine. Preferably, the aromatic diamine is 1,4-xylene-diamine or isomers of 1,4-xylene-diamine.

In yet an embodiment of the present invention the adsorbent may be coupled with a ligand having an acid group, an aromatic or heteroaromatic moiety, a bicyclic substituted heteroaromatic group or any combination hereof, such as a ligand having an acid group and an aromatic or heteroaromatic moiety, a ligand having an acid group and a bicyclic substituted heteroaromatic group or an aromatic or heteroaromatic moiety and a bicyclic substituted heteroaromatic group.

In another embodiment of the present invention the ligand comprises a bicyclic substituted heteroaromatic group which may be derived from compounds selected from the group consisting of benzimidazoles, benzothiazoles, and benzoxazoles.

In an embodiment of the present invention the ligand may be an aromatic or heteroaromatic acid selected from the group consisting of carboxylic acids, sulfonic acids, phosphonic acids, and boronic acids. Preferably, the ligand may be selected from the group consisting of 2-mercaptobenzoic acid, 2-mercaptonicotinic acid, 2-aminobenzoic acid, 3-aminobenzoic acid, and 4-aminobenzoic acid, 4-hydroxy-phenyl-mercapto-acetic acid, 4-hydroxyphenyl-mercapto-propionic acid, 4-hydroxyphenyl-mercapto-butanoic acid, 2,3-dihydroxy-benzoic acid, 2,4 dihydroxy-benzoic acid, 2,5 di-hydroxy-benzoic acid, 2,6 dihydroxy-benzoic acid, 3,4-dihydroxy-benzoic acid, 3,5-dihydroxy-benzoic acid, mercaptobenzimidazole sulfonic acid, orthanilic acid, metanilic acid, sulphanilic acid, 4-methylaniline-2-sulphonic acid, 4-methoxyaniline-2-sulphonic acid, aniline-2,5-disulphonic acid, N-methylmetanilic acid, 7-amino-1-naphthol-3-sulphonic acid, 1-naphthol-4-sulphonic acid, 2-naphthol-6-sulphonic acid and 2-hydroxy-3-naphthoic acid, and 2-mercaptobenzimidazole-sulphonic acid.

In an embodiment of the present invention the ligand may be an N-benzoyl amino acid or an N-benzoyl amino acid comprising thiol or mercapto groups.

In yet an embodiment of the present invention the ligand may be coupled to the adsorbent through a thio-ether linkage, an amine linkage, or an oxygen-ether linkage.

The optimal concentration of the covalently attached functional groups (the ligands) on the polymeric adsorbent backbone (also frequently referred to as the density of functional groups or the ligand concentration) will depend on the detailed structure of the functional group and the type of adsorbent material used to prepare the adsorbent.

In order to ensure an optimal adsorption strength and productivity of the adsorbent it has been found that the ligand concentration on the adsorbent may be significant. Thus, in a suitable embodiment, the adsorbent carries ligands for adsorption of the biomolecular substances in a concentration of at least 20 mM, such as at least 30 mM or at least 40 mM, preferably at least 50 mM and most preferably at least 60 mM.

However, generally it would be preferred that the adsorbent has a concentration of covalently attached functional groups in the range of 5-500 millimole per liter adsorbent in its sedimented (packed) bed state, more preferably in the range of 10-250 millimole per liter, still more preferably in the range of 10-125 millimole per liter, still more preferably in the range of 15-100 millimole per liter, still more preferably in the range of 20-80 millimole per liter still more preferably in the range of 25-75 millimole per liter still more preferably in the range of 30-60 millimole per liter.

In an embodiment of the present invention the covalently attached functional groups may be attached to the adsorbent by any type of covalent bond known per se to be applicable for this purpose, either by a direct chemical reaction between the ligand and the adsorbent or by a preceding activation of the adsorbent or of the ligand with a suitable reagent known per se making it possible to link the polymeric matrix backbone and the functional group. Examples of such suitable activating reagents are epichlorohydrin, epibromohydrin, allyl glycidylether; bis-epoxides such as butanediol-diglycidylether; halogen-substituted aliphatic compounds such as di-chloro-propanol, carbonyldiimidazole; aldehydes such as glutaric dialdehyde; quinones; periodates such as sodium-meta-periodate; carbodiimides; sulfonyl chlorides such as tosyl chlorides and tresyl chlorides; N-hydroxy succinimides; 2-fluoro-1-methylpyridinium toluene-4-sulfonates; oxazolones; maleimides; pyridyl disulfides; and hydrazides. Among these, the activating reagents leaving a spacer group SP1 different from a single bond, e.g. epichlorohydrin, epibromohydrin, allyl-glycidylether; bis-epoxides; halogen-substituted aliphatic compounds; aldehydes; quinones; cyanogen bromide; chloro-triazines; oxazolones; maleimides; pyridyl disulfides; and hydrazides, are preferred.

Especially interesting activating reagents are epoxy-compounds such as epichlorohydrin, allyl-glycidylether and butanedioldiglycidylether and polyglycidylethers such as glycerol polyglycidylether. In certain cases wherein the stability of the covalent binding of the functional group can be shown to be stable to treatment with sodium hydroxide e.g. 0.1 M to 2 M sodium hydroxide the activating reagent may be based on triazine derived reagents e.g chloro-triazines such as cyanuric chloride.

The above mentioned possibilities makes it relevant to define the presence of an optional spacer SP1 lining the polymeric adsorbent backbone (also referred to as the matrix polymer) and the functional group. In the present context the spacer SP1 may be considered as being part of the activating reagent, which forms the link between the matrix polymer and the functional group. Thus, the spacer SP1 corresponds to the activating reagents and the coupling reactions involved. In some cases, e.g. when using carbodiimides, the activating reagent forms an activated form of the matrix polymer or of the functional group reagent. After coupling no parts of the activating reagent is left between the functional group and the matrix polymer, and, thus, SP1 is simply a single bond.

In other cases the spacer SP1 may be an integral part of the functional group effecting the binding characteristics, i.e. the functional group, and this will be especially significant if the spacer SP1 comprises functionally active sites or substituents such as thiols, amines, acidic groups, sulfone groups, nitro groups, hydroxy groups, nitrile groups or other groups able to interact through hydrogen bonding, electrostatic bonding or repulsion, charge transfer or the like.

In still other cases the spacer SP1 may comprise an aromatic or heteroaromatic ring, which plays a significant role for the binding characteristics of the adsorbent. This would for example be the case if quinones or chlorotriazines where used as activation agents for the adsorbent or the functional group.

In a further case, the spacer SP1 may be a single bond or a biradical derived from an activating reagent selected from epichlorohydrin, allyl-glycidylether, allylbromide, bis-epoxides such as butanedioldiglycidylether, halogen-substituted aliphatic compounds such as 1,3-dichloropropan-2-ol, aldehydes such as glutaric dialdehyde, quinones, cyanogen bromide, chloro-triazines such as cyanuric chloride, 2-fluoro-1-methylpyridinium toluene-4-sulfonates, maleimides, oxazolones, and hydrazides.

In an embodiment of the present invention the spacer SP1 may be a short chain aliphatic biradical, e.g. having the formula: —$CH_2$—CH(OH)—$CH_2$— (derived from epichlorohydrin), —$(CH_2)_3$—O—$CH_2$—CH(OH)—$CH_2$— (derived from allyl-glycidylether) or —$CH_2$—CH(OH)—$CH_2$—O—$(CH_2)_4$—O—$CH_2$—CH(OH)—$CH_2$— (derived from butane-dioldiglycidylether; or a single bond.

In an embodiment of the present invention the adsorbents typically comprises a ligand comprising aromatic or heteroaromatic groups (radicals) selected from the groups comprising i) ligands comprising the following types as functional groups: benzoic acids such as 2-aminobenzoic acids, 3-aminobenzoic acids, 4-aminobenzoic acids, 2-mercaptobenzoic acids, 4-amino-2-chlorobenzoic acid, 2-amino-5-chlorobenzoic acid, 2-amino-4-chlorobenzoic acid, 4-aminosalicylic acids, 5-aminosalicylic acids, 3,4-diaminobenzoic acids, 3,5-diaminobenzoic acid, 5-aminoisophthalic acid, 4-aminophthalic acid; cinnamic acids such as hydroxycinnamic acids; nicotinic acids such as 2-mercaptonicotinic acids; naphthoic acids such as 2-hydroxy-1-naphthoic acid; quinolines such as 2-mercaptoquinoline; tetrazolacetic acids such as 5-mercapto-1-tetrazolacetic acid; thiadiazols such as 2-mercapto-5-methyl-1,3,4-thiadiazol; benzimidazols such as 2-amino-benzimidazol, 2-mercaptobenzimidazol, and 2-mercapto-5-nitrobenzimidazol; benzothiazols such as 2-aminobenzothiazol, 2-amino-6-nitrobenzothiazol, 2-mercaptobenzothiazol and 2-mercapto-6-ethoxybenzothiazol; benzoxazols such as 2-mercaptobenzoxazol; thiophenols such as thiophenol and 2-aminothiophenol; 2-(4-aminophenylthio)acetic acid; aromatic or heteroaromatic sulfonic acids and phosphonic acids, such as 1-amino-2-naphthol-4-sulfonic acid and phenols such as 2-amino-4-nitro-phenol. It should be noted that the case where M is agarose, SP1 is derived from vinyl sulfone, and L is 4-aminobenzoic acid may be specifically disclaimed in relation to the solid phase matrices according to the invention, cf. WO 92/16292, most preferably amino-benzoic acids like 2-amino-benzoic acid, 2-mercapto-benzoic acid, 3-aminobenzoic acid, 4-aminobenzoic acid, 4-amino-2-chlorobenzoic acid, 2-amino-5-chlorobenzoic acid, 2-amino-4-chlorobenzoic acid, 4-aminosalicylic acids, 5-aminosalicylic acids, 3,4-diaminobenzoic acids, 3,5-diaminobenzoic acid, 5-5-aminoisophthalic acid, 4-aminophthalic acid. Generally, the coupling using divinyl sulphone may not be suitable because the divinyl sulphone coupling is unstabil when contacted with an alkaline and as alkalines are presently the most suitable and used cleaning agents, adsorbents coupled with divinyl sulphone are not being considered industrial relevant; ii) ligands comprising 2-hydroxy-cinnamic acids, 3-hydroxy-cinnamic acid and 4-hydroxy-cinnamic acid iii) ligands comprising a carboxylic acid and an amino group as substituents such as 2-amino-nicotinic acid, 2-mercapto-nicotinic acid, 6-amino-nicotinic acid and 2-amino-4-hydroxypyrimidine-carboxylic acid iv) ligand comprising radicals derived from a benzene ring fused with a heteroaromatic ring system, e.g. a ligand selected from benzimidazoles such as 2-mercapto-benzimidazol and 2-mercapto-5-nitro-benzimidazol; benzothiazols such as 2-amino-6-nitrobenzothiazol, 2-mercaptobenzothiazol and 2-mercapto-6-ethoxybenzothiazol; benzoxazols such as 2-mercaptobenzoxazol; and v) ligands chosen from the group of thiophenols such as thiophenol and 2-aminothiophenol.

Within the embodiment wherein the ligand is selected from group i)-v) mentioned above, the adsorbents typically have a dynamic binding capacity of at least 10 g of biomolecular substance per litre, more preferably at least 20 g per litre, still more preferable at least 30 g per litre when tested according to the process conditions used in the relevant application. The binding capacity of the adsorbent may be determined in terms of its binding capacity to bovine serum albumin (BSA). The binding capacity is typically such that at least 10 g/L of BSA binds according to test Method A.

Method A

Method A is a method used for determination of the bovine albumin binding capacity of selected adsorbents consisting of the following process:

Bovine serum albumin solution pH 4.0 (BSA pH 4.0): Purified bovine serum albumin (A 7906, Sigma, USA) is dissolved to a final concentration of 2 mg/ml in 20 mM sodium citrate pH 4.0. Adsorbents are washed with 50 volumes of 20 mM sodium citrate pH 4.0 and drained on a suction filter.

A sample of 1.0 ml suction drained adsorbent is placed in a 50 ml test tube followed by the addition of 30 ml of BSA, pH 4.0.

The test tube is then closed with a stopper and the suspension incubated on a roller mixer for 2 hours at room temperature (20-25° C.). The test tube is then centrifuged for 5 min. at 2000 RPM in order to sediment the adsorbent completely. The supernatant is then isolated from the adsorbent by pipetting into a separate test tube, avoiding the carry-over of any adsorbent particles and filtered through a small non-adsorbing 0.2 μm filtre (Millipore, USA). Following this a determination of the concentration of non-bound BSA in the supernatant is performed by measuring the optical density (OD) at 280 nm on a spectrophotometer.

The amount of BSA bound to the adsorbent is then calculated according to the following formula:

$$\text{mg BSA bound per ml suction drained adsorbent} = (1 - (\text{OD of test supernatant/OD of BSA starting solution})) \times 60 \text{ mg BSA/ml adsorbent}.$$

The Process Parameters

As mentioned above the protein solution comprising one or more protein(s) of interest may be adjusted to having a preset pH and a preset ionic strength or conductivity.

In the present context the term "preset" relates to the adjustment of the pH, ionic strength or conductivity, respectively, to a specific and predetermined value for the purpose of selecting the ability of the adsorbent for binding the one or more protein(s) of interest and thereby increasing the efficiency of the adsorbent for protein(s) isolation.

In an embodiment of the present invention the preset pH is in the range of pH 3.0 to pH 10.0, preferably in the range of pH 4 to pH 9, more preferably in the range of pH 4 to pH 8, even more preferably in the range of pH 4 to pH 7, still more preferably in the range of pH 4 to pH 6, still more preferably in the range of pH 4.5 to pH 5.5 or in the range of pH 4 to pH 10, preferably in the range of pH 5 to pH 9, more preferably in the range of pH 6 to pH 9, even more preferably in the range of pH 6 to pH 8.

In yet an embodiment of the present invention the preset ionic strength is in the range of 0.0001 to 12.0, preferably in the range of 0.0001 to 5, more preferably in the range of 0.0001 to 1, even more preferably in the range of 0.0001 to 0.1, still more preferably in the range of 0.0001 to 0.075, still more preferably in the range of 0.01 to 0.05 or in the range of 0.1 to 12.0, preferably in the range of 0.5 to 12, more preferably in the range of 1 to 12, even more preferably in the range of 1.5 to 12, still more preferably in the range of 2 to 12, still more preferably in the range of 4 to 12.

In another embodiment of the present invention the preset conductivity is in the range of 0.01 to 1000 mS/cm, preferably in the range of 0.01 to 200 mS/cm, more preferably in the range of 0.05 to 100 mS/cm, more preferably in the range of 0.1 to 50 mS/cm, more preferably in the range of 0.5 to 20 mS/cm, more preferably in the range of 1.0 to 10 mS/cm, still more preferably in the range of 1.0 to 5 mS/cm or in the range of 10 to 1000 mS/cm, preferably in the range of 100 to 1000 mS/cm, more preferably in the range of 200 to 1000 mS/cm, more preferably in the range of 300 to 1000 mS/cm, more preferably in the range of 400 to 1000 mS/cm, more preferably in the range of 500 to 1000 mS/cm, still more preferably in the range of 600 to 1000 mS/cm, more preferably in the range of 2.0 to 15 mS/cm, more preferably in the range of 2.0 to 12 mS/cm, still more preferably in the range of 2.0 to 10 mS/cm.

The ionic strength and conductivity of the protein solutions according to the present invention are related entities in that both entities are functions of the concentration of ions in the solution. There is, however, no direct theoretical correspondence between them.

When considering an ion-containing solution, it is relatively easy for the person skilled in the art to calculate the amount of e.g. an inorganic salt necessary to achieve a certain ionic strength. Conversely, when the person skilled in the art is faced with the problem of determining the ionic strength without knowing the amount of added salt, it is difficult to make an accurate assessment since ionic strength is a theoretical entity calculated from both the concentration of ions and the charge of the ions. In this situation it is considerably easier for the person skilled in the art to measure the conductivity. For these reasons, the terms "ionic strength" and "conductivity" are used in the present context to characterise the same conditions. When referring to preferred ranges for these two entities, though, it is not meant to say that there is any correspondence between the indicated lower or upper limits of the ionic strength and conductivity, respectively.

For obtaining the one or more protein(s) from the adsorbent the one or more protein(s) may be eluted with one or more buffer(s). Optionally, adsorbent may be washed with a washing buffer before being subjected to the elution buffer. In an embodiment of the present invention the adsorbent is washed with a washing buffer to wash out non-bound material before eluting one or more protein(s) from the adsorbent.

Virus Elimination

For increasing the safety measures needed to prevent viral diseases to spread from blood donors to recipients of the blood products it may be necessary to introduce one or more virus elimination steps.

In an embodiment of the present invention the protein solution may be subjected to at least one virus elimination treatment. Preferably, at least one virus elimination treatment may be performed prior to contacting the protein solution with the adsorbent.

The virus elimination treatment may involve the addition of a detergent and/or an organic solvent, such as, TWEEN® polysorbates, TRITON® octylphenol ethoxylates, tri-n-butylphosphate, to the protein solution.

In an embodiment of the present invention several virus elimination steps may be performed and preferably one virus elimination treatment may be performed prior to contacting the protein solution with the adsorbent.

In an embodiment of the present invention several virus elimination steps may be performed and preferably one virus elimination treatment is performed prior to contacting the protein solution with the adsorbent and, during the adsorption step, any substances, such as detergents and/or organic solvents added to the protein solution remain unbound to the adsorbent and is washed out of the column prior to elution of the protein to be isolated.

In yet an embodiment of the present invention a process for eliminating viruses in biological fluids may be preformed by a treatment with organic solvents and/or detergents; especially treatment with tri(n-butyl)phosphate (TNBP) and non-ionic detergents such as TWEEN® 80 polysorbates, TRITON® X-100 octylphenol ethoxylates. This method may result in excellent recovery of labile proteins, e.g., coagulation factor VIII and IX, while achieving a high level of virus kill, e.g., the killing of $>10^6$ to $>10^8$ ID, of enveloped viruses; however, little elimination of non-enveloped viruses. U.S. Pat. No. 4,481 189 disclose viral elimination by a treatment with non-anionic detergent, alcohols, ethers, or mixtures thereof. U.S. Pat. No. 4,481,189 are hereby incorporated by reference.

Other methods of virus elimination commonly applied, and applicable in the present invention, to biological fluids to be used in a transfusion treatment may also involve a treatment with heat at temperatures at 60° C. or more, or treatment with UVC together alone or together with B-propiolactone (B-PL).

Further Embodiments

In an embodiment of the present invention the method further involves the step of subjecting the adsorbent to an elution buffer (a first elution buffer) to elute at least one of said one or more protein(s).

The use of an adsorbent coupled with a functional group (ligand) according to the present invention, for the isolation of one or more protein(s) from a protein solution such as from plasma or serum or other blood derived sources may comprises the steps of: (i) Providing a protein solution comprising one or more plasma or serum protein having a preset pH and a preset ionic strength, (ii) contacting said solution with an adsorbent, optionally washed with one or more equilibration buffers, whereby one or more plasma or serum protein may be reversibly bound to the adsorbent or remains unbound, (iii) washing the adsorbent with a washing buffer to obtain a protein fraction comprising non-bound material, (iv) washing the adsorbent with at least one elution buffer to obtain at least one eluate comprising protein(s) that was reversibly bound by the adsorbent, (v) subjecting the protein(s) obtained in the washing buffer or the protein(s)

obtained in the elution buffer to further down stream processing which may include at least one viral elimination step. Furthermore, the ligand coupled to the adsorbent may comprise a functionalized matrix polymer carrying a plurality of covalently attached functional groups comprising an aromatic or heteroaromatic ring-system and one or more acidic groups being negatively charged above pH 4.0.

For the purpose of removing unbound material, including unbound protein(s), the adsorbent may be subjected to a washing buffer. In an embodiment of the present invention the one or more protein(s) to be isolated from the protein solution may be washed out of the adsorbent with the washing buffer. This washing may be performed before subjecting the adsorbent to an elution buffer as described above. In an embodiment of the present invention alpha-1-proteinase inhibitor may be washed out as a non-bound protein with the washing buffer. The process conditions, the adsorbent and the ligand could easily be changed by the person skilled in the art in such a way that one or more other human serum or plasma protein(s) (other than alpha-1-proteinase inhibitor) may be washed out with the washing buffer and alpha-1-proteinase inhibitor may be bound.

In an embodiment washing and/or elution may be performed with a washing buffer and/or an elution buffer having a higher pH and/or a higher ionic strength than the preset pH and preset ionic strength of the protein solution.

In still another embodiment the washing buffer and/or the elution buffer may comprise one or more compounds having a hydrophobic as well as a negatively charged group within the same molecule e.g. negatively charged detergent such as octyl sulfate, bromphenol blue, octane sulfonate, sodium laurylsarcosinate, hexane sulfonate, sodium dodecyl sulfate, sodium caprylate.

For the purpose of obtaining one or more additional protein(s) from the adsorbent the process according to the present invention further comprises the step of eluting with one or more additional elution buffer(s) to elute remaining protein(s).

In the present context the term "additional elution buffer(s)" relates to the buffer(s) subsequently used for the elution of one or more protein(s), which remains bound to the adsorbent after the elution with the first elution buffer.

In the present context the term "remaining protein(s)" relates to the one or more protein(s) which remains bound to the adsorbent after being subjected to a first elution buffer and which protein(s) may subsequently be eluted by the addition of an additional elution buffer.

In an embodiment of the present invention the adsorbent may be washed with an additional washing buffer between each elution step.

In the present context the term "protein fraction" relates to the collections obtained from the adsorbent wherein the one or more protein(s) to be isolated may be located. This protein fraction may be subjected to further downstream processing for further isolation of the one or more protein(s) present. The further downstream processing may involve operations like filtration, centrifugation, sedimentation, microfiltration, precipitation and chromatography. In an embodiment of the present invention chromatography involves ion exchange chromatography, gel filtration, affinity chromatography, hydrophobic interaction chromatography and reversed phase chromatography, where the protein(s) may be bound to a second adsorbent in subsequent down stream processing.

In an embodiment of the present invention the further downstream processing may comprise the adsorption of the protein in the protein fraction(s), such as alpha-1-proteinase inhibitor, to a positively charged ion exchanger In an embodiment of the present invention the further downstream processing may comprise the adsorption of the protein in the protein fraction(s), such as alpha-1-proteinase inhibitor, to an alkyl-amine such as an alkyl-diamine such as diamino-hexane, diamino-heptane, diamino-octane, diamino-nonane, diamino-decane and isomers or derivatives hereof.

In an embodiment of the present invention alpha-1-proteinase inhibitor is unbound in the first adsorption step and the further downstream processing comprise the adsorption of the alpha-1-proteinase to an alkyl-amine such as an alkyl-diamine such as diamino-hexane, diamino-heptane, diamino-octane, diamino-nonane, diamino-decane or isomers or derivatives hereof In an embodiment of the present invention the further downstream processing may comprise the adsorption of the protein in the protein fraction, such as alpha-1-proteinase inhibitor, to an adsorbent in the presence of a lyotropic salt such as, but not limited to ammonium sulfate, potassium sulfate, sodium sulfate, ammonium phosphate, potassium phosphate, and sodium citrate. In a preferred embodiment the concentration of lyotropic salt in the solution comprising alpha-1-proteinase inhibitor is at least 0.1 M, at least 0.25 M, such as at least 0.5 M, at least 0.75 M, at least 1 M, at least 1.25 M, at least 1.5 M, at least 1.75 M or at least 2 M.

In yet an embodiment of the present invention the further downstream processing comprise the adsorption of the protein in the protein fraction, such as alpha-1-proteinase inhibitor, to an adsorbent in the presence or absence of a lyotropic salt wherein the adsorbent comprise a hydrophobic ligand such as an uncharged ligand comprising long, optionally substituted, alkyl chains (e.g. butyl-, hexyl-, octyl-, decyl-, dodecyl-derived groups) and/or aromatic and heteroaromatic structures (e.g. phenyl-, naphthyl-, benzimidazole derived groups). Also preferred are ligands such as those described in U.S. Pat. No. 6,610,630 wherein there is disclosed chromatography adsorbents utilizing mercapto-heterocyclic ligands, hereby incorporated by reference. Further preferred ligands are mixed mode ligands comprising a positive charge at, and below, about pH 4 such as positive charged ligands comprising long, optionally substituted, alkyl chains (e.g. butyl-, hexyl-, octyl-, decyl-, dodecyl-derived groups) and/or aromatic and heteroaromatic structures (e.g. phenyl-, naphthyl-, benzimidazole derived groups). Non-limiting examples of such ligands are butylamine, hexylamine-, octylamine-, benzylamine and phenyl-butylamine-.

In an embodiment of the present invention a process for the large-scale isolation of one or more protein(s) according to the present invention is provided. The process comprises the steps of:
  a) providing a protein solution comprising said one or more protein(s) and said protein solution having a preset pH and optionally a preset ionic strength or conductivity;
  b) contacting said protein solution with an adsorbent, wherein the adsorbent comprises a functionalized matrix polymer carrying a plurality of covalently attached functional groups comprising an aromatic or heteroaromatic ring-system and one or more acidic groups; and
  c) obtaining said one or more protein(s) from said adsorbent.

In a further embodiment of the present invention a process for the large-scale isolation of one or more protein(s) according to the present invention is provided. The process comprises the steps of:
a) providing a protein solution comprising said one or more protein(s) and said protein solution having a preset pH and optionally a preset ionic strength or conductivity;
b) contacting said protein solution with an adsorbent, wherein the adsorbent comprises a particle with at least one high density non-porous core, surrounded by a porous material and/or said particle having a particle density of at least 1.5 g/ml and a mean volume particle size of at the most 150 µm; and
c) obtaining said one or more protein(s) from said adsorbent.

In an embodiment of the present invention 2 or more proteins from the protein solution are isolated by the means of a cascade of 2 or more adsorbents, such as 3 adsorbents, e.g. 4 adsorbents, such as 5 adsorbents, e.g. 6 adsorbents, such as 7 adsorbents, e.g. 8 adsorbents, such as 9 adsorbents, e.g. 10 adsorbents.

In a cascade of 3 adsorbents the following process may occur:
a) the first adsorbent is capable of capturing one or more blood protein(s), serum protein(s) or plasma protein(s);
b) the second adsorbent is capable of capturing one or more blood protein(s), serum protein(s) or plasma protein(s) different for the one or more blood protein(s), serum protein(s) or plasma protein(s) capable of being captured to the first adsorbent; and
c) the third adsorbent is capable of capturing one or more blood protein(s), serum protein(s) or plasma protein(s) different for the one or more blood protein(s), serum protein(s) or plasma protein(s) capable of being captured to the first adsorbent or second adsorbent;

In an embodiment of the present invention one or more coagulation factor(s) or anti-coagulation factor(s) such as Factor II, Factor V, Factor VII, Factor VIII, von Willebrand factor, Factor VIII—von Willebrand factor complex, Factor IX, Factor X, Factor XI, C1 inhibitor, protein C and Protein S, is/are bound to a first adsorbent. In an embodiment of the present invention at least 2 of the coagulation or anti-coagulation factors binds to the adsorbent, such as at least 3 of the coagulation or anti-coagulation factors, e.g. at least 4 of the coagulation or anti-coagulation factors, such as at least 5 of the coagulation or anti-coagulation factors, e.g. at least 6 of the coagulation or anti-coagulation factors, such as at least 7 of the coagulation or anti-coagulation factors, e.g. 8 of the coagulation or anti-coagulation factors.

In another embodiment of the present invention at least one of the proteins selected from albumin, IgG, tranferrin, fibrinogen is/are bound to a second adsorbent. In an embodiment of the present invention at least 2 of the proteins binds to the adsorbent, such as at least 3 of proteins, e.g. 4 of the proteins.

In yet an embodiment of the present invention, at least one of the proteins α-1-proteinase inhibitor or α-1-acid-glycoprotein binds to a third adsorbent. In an embodiment of the present invention 2 of the proteins binds to the adsorbent.

In a further embodiment of the present invention the proteins selected from the group consisting of IgG, albumin, fibrinogen, α-1-proteinase inhibitor, α-1-acid-glycoprotein, and one or more coagulation or anti-coagulation factor(s) such as Factor II, Factor V, Factor VII, Factor VIII, von Willebrand factor, Factor VIII—von Willebrand factor complex, Factor IX, Factor X, Factor XI, C1 inhibitor, protein C and/or Protein S, is/are isolated in at least 2 individual protein fractions, such as 3 individual protein fractions, e.g. 4 individual protein fractions, such as 5 individual protein fractions, e.g. 6 individual protein fractions. Furthermore, it is preferred that the degree of cross-contamination of the individual protein in the protein fraction is at the most 20%, such as at the most 15%, e.g. at the most 10%, such as at the most 5%, e.g. at the most 3%, such as at the most 1%, e.g. at the most 0.5%, such as at the most 0.1%, e.g. at the most 0.01%. Preferably, the individual protein fraction are obtained within a single adsorption circle.

In accordance with the present invention the one or more protein(s) to be isolated may be isolated by one of the following:
(i) One or more protein(s) to be isolated may be washed through the adsorbent without specifically binding to the adsorbent collected in the washing buffer.
(ii) One or more protein(s) to be isolated may bind specifically to the adsorbent and subsequently be eluted using one or more elution buffer(s) and collected in the one or more elution buffer(s).
(iii) One or more of the protein(s) to be isolated may be washed through adsorbent and another one or more protein to be isolated may be specifically bound to the adsorbent and collected in the washing buffer, and one or more of the protein(s) of interest may subsequently be eluted with one or more elution buffer(s) and collected in the one or more elution buffer(s).

In an embodiment of the present invention fibrinogen may be bound to the adsorbent and simultaneously one or more of the coagulation or anti-coagulation factor(s) such as Factor II, Factor V, Factor VII, Factor VIII, von Willebrand factor, Factor VIII—von Willebrand factor complex, Factor IX, Factor X, Factor XI, C1 inhibitor, protein C and/or Protein S may be obtained as non-bound material from the adsorbent. Preferably, at least 50% of the fibrinogen may bind to the adsorbent, such as at least 60%, e.g. at least 70%, such as at least 80%, e.g. at least 90%, such as at least 95%, e.g. at least 98%.

In another embodiment of the present invention albumin and IgG may be bound to the adsorbent and simultaneously α-1-proteinase inhibitor may be obtained as non-bound material from the adsorbent. Subsequently, albumin and IgG may be obtained from the adsorbent by stepwise elution. Preferably, at least 50% of the albumin may bind to the adsorbent, such as at least 60%, e.g. at least 70%, such as at least 80%, e.g. at least 90%, such as at least 95%, e.g. at least 98%. Preferably, at least 50% of the IgG may bind to the adsorbent, such as at least 60%, e.g. at least 70%, such as at least 80%, e.g. at least 90%, such as at least 95%, e.g. at least 98%.

In the present context the term "stepwise elution" relates to a gradual but discontinuous change of the properties of an elution buffer added to the adsorbent in terms of, but not limited to, changes of ionic strength or conductivity, pH, polarity, temperature, concentration of competing substances and so on.

In another embodiment of the present invention fibrinogen and IgG may be bound to the adsorbent and simultaneously albumin may be obtained as non-bound material from the adsorbent. Subsequently, fibrinogen and IgG may be obtained from the adsorbent by stepwise elution. Preferably, at least 50% of the IgG may bind to the adsorbent, such as at least 60%, e.g. at least 70%, such as at least 80%, e.g. at least 90%, such as at least 95%, e.g. at least 98%. Preferably, at least 50% of the fibrinogen may bind to the adsorbent, such as at least 60%, e.g. at least 70%, such as at least 80%, e.g. at least 90%, such as at least 95%, e.g. at least 98%.

In another embodiment of the present invention fibrinogen, albumin and IgG may be bound to the adsorbent and simultaneously α-1-proteinase inhibitor may be obtained as non-bound material from the adsorbent. Subsequently, fibrinogen, albumin and IgG may be obtained from the adsorbent by stepwise elution. Preferably, at least 50% of the IgG may bind to the adsorbent, such as at least 60%, e.g. at least 70%, such as at least 80%, e.g. at least 90%, such as at least 95%, e.g. at least 98%. Preferably, at least 50% of the fibrinogen may bind to the adsorbent, such as at least 60%, e.g. at least 70%, such as at least 80%, e.g. at least 90%, such as at least 95%, e.g. at least 98%. Preferably, at least 50% of the albumin may bind to the adsorbent, such as at least 60%, e.g. at least 70%, such as at least 80%, e.g. at least 90%, such as at least 95%, e.g. at least 98%.

In another embodiment of the present invention at least 1, such as at least 2 e.g. 3 of fibrinogen, albumin and IgG may be bound to the adsorbent and simultaneously α-1-acid glycoprotein may be obtained as non-bound material from the adsorbent. Subsequently, fibrinogen, albumin and/or IgG may be obtained from the adsorbent by stepwise elution. Preferably, at least 50% of the IgG may bind to the adsorbent, such as at least 60%, e.g. at least 70%, such as at least 80%, e.g. at least 90%, such as at least 95%, e.g. at least 98%. Preferably, at least 50% of the fibrinogen may bind to the adsorbent, such as at least 60%, e.g. at least 70%, such as at least 80%, e.g. at least 90%, such as at least 95%, e.g. at least 98%. Preferably, at least 50% of the albumin may bind to the adsorbent, such as at least 60%, e.g. at least 70%, such as at least 80%, e.g. at least 90%, such as at least 95%, e.g. at least 98%.

In another embodiment of the present invention at least 1, such as at least 2 e.g. 3 of fibrinogen, albumin and IgG may be bound to the adsorbent and simultaneously α-1-acid glycoprotein and/or α-1-proteinase inhibitor may be obtained as non-bound material from the adsorbent. Subsequently, fibrinogen, albumin and/or IgG may be obtained from the adsorbent by stepwise elution. Preferably, at least 50% of the IgG may bind to the adsorbent, such as at least 60%, e.g. at least 70%, such as at least 80%, e.g. at least 90%, such as at least 95%, e.g. at least 98%. Preferably, at least 50% of the fibrinogen may bind to the adsorbent, such as at least 60%, e.g. at least 70%, such as at least 80%, e.g. at least 90%, such as at least 95%, e.g. at least 98%. Preferably, at least 50% of the albumin may bind to the adsorbent, such as at least 60%, e.g. at least 70%, such as at least 80%, e.g. at least 90%, such as at least 95%, e.g. at least 98%.

In an embodiment of the present invention at least 50% α-1-proteinase inhibitor, albumin, IgG, fibrinogen or one or more coagulation or anti-coagulation factor(s) such as Factor II, Factor V, Factor VII, Factor VIII, von Willebrand factor, Factor VIII—von Willebrand factor complex, Factor IX, Factor X, Factor XI, C1 inhibitor, protein C and/or Protein S may be obtained from the adsorbent, such as at least 60%, e.g. at least 70%, such as at least 80%, e.g. at least 90%, such as at least 95%, e.g. at least 98%.

In an embodiment of the present invention albumin may be bound to the adsorbent and simultaneously α-1-proteinase inhibitor may be obtained as non-bound material from the adsorbent. Preferably, at least 50% of the albumin may bind to the adsorbent, such as at least 60%, e.g. at least 70%, such as at least 80%, e.g. at least 90%, such as at least 95%, e.g. at least 98%.

In an embodiment of the present invention α-1-proteinase inhibitor may be isolated from a protein solution, such as plasma or serum, by a process comprising the steps of (i) contacting an aqueous solution of plasma proteins containing IgG, albumin and α-1-proteinase inhibitor with an anion exchange adsorbent under conditions such that the albumin and alpha-1-proteinase inhibitor bind to the adsorbent and the IgG remains unbound, wherein the protein solution is selected from the group consisting of pretreated cryopoor plasma, pretreated cryopoor serum, pretreated supernatant I or pretreated supernatant II+III, pretreated supernatant I+II+III; (ii) optionally recovering the unbound IgG to obtain an IgG rich protein fraction; (iii) eluting albumin from the anion exchange medium to obtain an albumin rich protein fraction; and (iv) eluting from the anion exchange medium to obtain an α-1-proteinase inhibitor rich protein fraction.

In a further embodiment of the present invention the non-bound protein fraction may comprise the protein(s) washed through the adsorbent, such as α-1-protease inhibitor, α-1-acid-glycoprotein, albumin, IgG or fibrinogen in high yield. Preferably the yield will be more than 70%, more preferably more than 80%, more preferably more than 90% of the alpha-1-protease inhibitor.

It is a further object of the invention to provide a process wherein said protein(s) washed through the adsorbent, such as α-1-protease inhibitor, α-1-acid-glycoprotein, albumin, IgG or fibrinogen present in high yield in the non-bound protein fraction may subsequently be isolated from the non-bound protein fraction by further downstream processing, e.g. by employing a second chromatographic adsorption step.

It is an embodiment of the present invention to provide a process wherein multiple protein fractions are provided by each adsorption cycle such as at least 2 protein fractions, e.g. at least 3 protein fractions, such as at least 4 protein fractions, e.g. at least 5 protein fractions, such as at least 6 protein fractions. Preferably each of these protein fractions comprises a high yield of individual proteins without significant cross-contamination of the protein fraction(s) between the at least 2 proteins, such as at least 3 proteins e.g. at least 4 proteins, such as at least 5 proteins e.g. at least 6 proteins within the same protein fraction. In an embodiment of the present invention the amount of cross contamination in a protein fraction is less than 20%, such as less than 15%, e.g. less than 10%, such as less than 5%, e.g. less than 3%, such as less than 1%, e.g. less than 0.5%, such as less than 0.1%, e.g. less than 0.010%.

In the present context the term "cross-contamination" relates to the amount or content of protein not of interest which is present in the protein fraction. In some cases it is of interest to elute two or more proteins simultaneously in one elution circle and in this case the proteins intentionally eluted together are not considered contaminating. In an embodiment of the present invention the degree of cross-contamination of the individual protein in the protein fraction is at the most 20%, such as at the most 15%, e.g. at the most 10%, such as at the most 5%, e.g. at the most 3%, such as at the most 1%, e.g. at the most 0.5%, such as at the most 0.1%, e.g. at the most 0.01%.

The invention will be further illustrated in the following non-limiting figures, items and examples.

Figure 4:
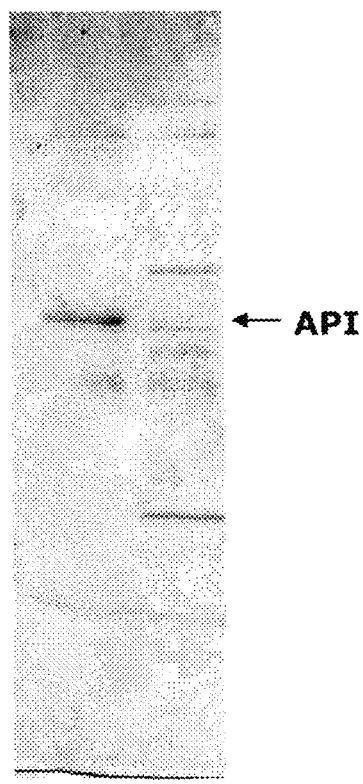

FIG. 4 illustrates elastase binding activity where lane 1 comprises protein solution without elastase incubation and lane 2 comprises protein solution+elastase incubation. The experiment showed that substantially all the alpha-1-proteinase inhibitor in the protein solution (non-bound fraction from example 5) is active and binds to elastase.

Figure 5:
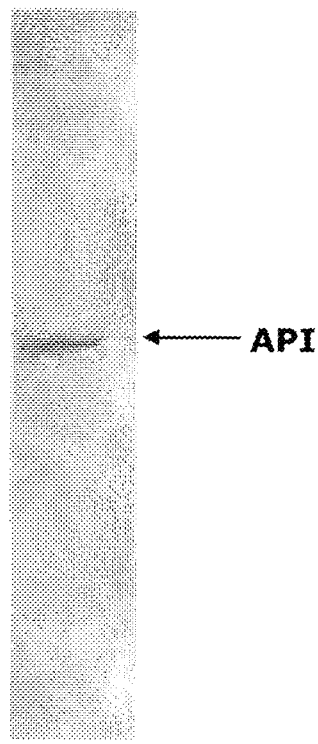

FIG. 5 illustrates the result in example 8 showing a very high degree of purity of the alpha-1-proteinase-inhibitor-eluate from example 5 using benzylamine as the ligand, and estimated by SDS-PAGE (estimated purity at >95%).

ITEMS

1. A process for the large-scale isolation of one or more protein(s) from a protein solution wherein the protein solution is obtained from a source selected from the group consisting of blood, such as serum and/or plasma, and other blood derived sources, said process comprising the steps of:
   f) optionally adjusting the pH of the protein solution to a preset pH;
   g) optionally adjusting the ionic strength or conductivity of the protein solution to a preset ionic strength or a preset conductivity;
   h) applying said protein solution to an adsorption column comprising an adsorbent, said adsorbent comprises a particle with at least one high density non-porous core, surrounded by a porous material, the adsorbent comprises a particle density of at least 1.5 g/ml and a mean volume particle diameter of at most 150 µm;
   i) optionally washing the column;
   j) obtaining the one or more protein(s) from the adsorbent.

2. A process according to item 1, wherein the protein solution is subjected to at least one virus elimination treatment.

3. A process according to item 2, wherein at least one virus elimination treatment is performed prior to contacting the protein solution with the adsorbent.

4. A process according to any one of items 1-3, wherein the virus elimination treatment involves addition of detergent and/or an organic solvent, such as TWEEN® polysorbates, TRITON® octylphenol ethoxylates, tri-n-butylphosphate, to the protein solution.

5. A process according to any one of items 1-4, wherein the adsorbent comprises a functionalized matrix polymer carrying a plurality of covalently attached functional groups comprising an aromatic or heteroaromatic ring-system and/or one or more acidic groups.

6. A process according to any one of items 1-5, wherein the blood, serum, plasma or other blood derived sources is obtained from humans or animals such as cows, fish, camel, pig, sheep, goat, rabbit, mouse, rat, horse, chicken, zebra or ostrich.

7. A process according to any one of items 1-6, wherein the one or more protein(s) is one or more human blood protein, such as one or more human plasma protein or one or more human serum protein.

8. A process according to any one of items 1-7, wherein said one or more human blood protein(s) is/are selected from the group consisting of albumin, IgG, IgA, IgM, IgD, IgE, alpha-1-proteinase inhibitor, blood pro-coagulation protein, blood anti-coagulation protein, thrombolytic agent, anti-angiogenic protein, α-2-antiplasmin, C-1 esterase inhibitor, apolipoprotein, HDL, LDL, Fibronectin, beta-2-glycoprotein I, fibrinogen, plasminogen, plasmin, plasminogen activator, plasminogen inhibitor, plasma protease inhibitor, antithrombin III, streptokinase, inter-alpha-trypsin inhibitor, α-2-macroglobulin, amyloid protein, ferritin, pre-albumin, GC-globulin, haemopexin, C3-complement, transferrin, urokinase, α-1-acid-glycoprotein, and the coagulation or anti-coagulation factor(s) such as Factor II, Factor V, Factor VII, Factor VIII, von Willebrand factor, Factor VIII—von Willebrand factor complex, Factor IX, Factor X, Factor XI, C1 inhibitor, protein C and/or Protein S.

9. A process according to any one of items 1-8, wherein one or more protein(s) are washed out as a non-bound protein with one or more washing buffer(s).

10. A process according to item 9, wherein one non-bound protein is alpha-1-proteinase inhibitor.

11. A process according to any one of items 1-10, wherein the protein solution has been supplemented with an alcohol.

12. A process for the large-scale isolation of one or more blood protein(s), such as one or more serum protein(s) or one or more plasma protein(s), from a protein solution, said process comprising the steps of:
   f) optionally adjusting the pH of the protein solution to a preset pH;
   g) optionally adjusting the ionic strength or conductivity of the protein solution to a preset ionic strength or a preset conductivity;
   h) applying said protein solution to an adsorption column comprising an adsorbent, said adsorbent comprises a particle with at least one high density non-porous core, surrounded by a porous material, the adsorbent comprises a particle density of at least 1.5 g/ml and a mean volume particle diameter of at most 150 µm;
   i) optionally washing the column;
   j) obtaining the one or more protein(s) from the adsorbent.

13. A process according to item 12, wherein the protein solution is obtained from a source selected from the group consisting of blood, serum, plasma, and other blood derived sources 14. A process according to item 13, wherein the blood, serum, plasma or other blood derived sources is obtained from humans or animals such as cows, fish, camel, pig, sheep, goat, rabbit, mouse, rat, horse, chicken, zebra or ostrich.

15. A process according to any one of items 12-14, wherein the protein solution is subjected to at least one virus elimination treatment.

16. A process according to item 15, wherein at least one virus elimination treatment is performed prior to contacting the protein solution with the adsorbent.

17. A process according any one of items 15-16, wherein the virus elimination treatment involves addition of detergent and/or an organic solvent, such as TWEEN® polysorbates, TRITON® octylphenol ethoxylates, tri-n- butylphosphate, to the protein solution.

18. A process according to any one of items 12-17, wherein the adsorbent comprises a functionalized matrix polymer carrying a plurality of covalently attached functional groups comprising an aromatic or heteroaromatic ring-system and/or one or more acidic groups.

19. A process according to any one of items 12-18, wherein the one or more protein(s) is one or more human blood protein, such as a human plasma protein or a human serum protein.

20. A process according to any one of items 12-19, wherein said one or more human blood protein(s) is/are selected from the group consisting of albumin, IgG, IgA, IgM, IgD, IgE, alpha-1-proteinase inhibitor, blood procoagulation protein, blood anti-coagulation protein, thrombolytic agent, anti-angiogenic protein, α-2-antiplasmin, C-1 esterase inhibitor, apolipoprotein, HDL, LDL, Fibronectin, beta-2-glycoprotein I, fibrinogen, plasminogen, plasmin, plasminogen activator, plasminogen inhibitor, plasma protease inhibitor, anti-thrombin III, streptokinase, inter-alpha-trypsin inhibitor, α-2-macroglobulin, amyloid protein, ferritin, pre-albumin, GC-globulin, haemopexin, C3-complement, transferrin, urokinase, α-1-acid-glycoprotein, and the coagulation or anti-coagulation factor(s) such as Factor II, Factor V, Factor VII, Factor VIII, von Willebrand factor, Factor VIII—von Willebrand factor complex, Factor IX, Factor X, Factor XI, C1 inhibitor, protein C and/or Protein S.

21. A process according to any one of items 12-20, wherein one or more protein(s) are washed out as a non-bound protein with one or more washing buffer(s).

22. A process according to item 21, wherein one non-bound protein is alpha-1-proteinase inhibitor.

23. A process according to any one of items 12-22, wherein the protein solution has been supplemented with an alcohol.

24. A process for the large-scale isolation of one or more protein(s) from a protein solution, said process comprising the steps of:
f) optionally adjusting the pH of the protein solution to a preset pH;
g) optionally adjusting the ionic strength or conductivity of the protein solution to a preset ionic strength or a preset conductivity;
h) applying said protein solution to an adsorption, said adsorbent comprises a particle with at least one high density non-porous core, surrounded by a porous material, the adsorbent comprises a particle density of at least 1.5 g/ml and a mean volume particle diameter of at most 150 µm;
i) optionally washing the adsorbent;
j) obtaining the one or more protein(s) from the adsorbent.
wherein the protein solution has been supplemented with an alcohol.

25. A process according to item 24, wherein the protein solution is obtained from a source selected from the group consisting of blood, serum, plasma, and other blood derived sources.

26. A process according to item 25, wherein the blood, serum, plasma or other blood derived sources is obtained from humans or animals such as cows, fish, camel, pig, sheep, goat, rabbit, mouse, rat, horse, chicken, zebra or ostrich.

27. A process according to any one of items 24-26, wherein the protein solution is subjected to at least one virus elimination treatment.

28. A process according to item 27, wherein at least one virus elimination treatment is performed prior to contacting the protein solution with the adsorbent.

29. A process according to item 28, wherein the virus elimination treatment involves addition of detergent and/or an organic solvent, such as TWEEN® polysorbates, TRITON® octylphenol ethoxylates, tri-n- butylphosphate, to the protein solution.

30. A process according to any one of items 24-29, wherein the adsorbent comprises a functionalized matrix polymer carrying a plurality of covalently attached functional groups comprising an aromatic or heteroaromatic ring-system and/or one or more acidic groups.

31. A process according to any one of items 24-30, wherein the one or more protein(s) is one or more human blood protein, such as a human plasma protein or a human serum protein.

32. A process according to any one of items 24-31, wherein said one or more human blood protein(s) is/are selected from the group consisting of albumin, IgG, IgA, IgM, IgD, IgE, alpha-1-proteinase inhibitor, blood procoagulation protein, blood anti-coagulation protein, thrombolytic agent, anti-angiogenic protein, α-2-antiplasmin, C-1 esterase inhibitor, apolipoprotein, HDL, LDL, Fibronectin, beta-2-glycoprotein I, fibrinogen, plasminogen, plasmin, plasminogen activator, plasminogen inhibitor, plasma protease inhibitor, anti-thrombin III, streptokinase, inter-alpha-trypsin inhibitor, α-2-macroglobulin, amyloid protein, ferritin, pre-albumin, GC-globulin, haemopexin, C3-complement, transferrin, urokinase, α-1-acid-glycoprotein, and the coagulation or anti-coagulation factor(s) such as Factor II, Factor V, Factor VII, Factor VIII, von Willebrand factor, Factor VIII—von Willebrand factor complex, Factor IX, Factor X, Factor XI, C1 inhibitor, protein C and/or Protein S.

33. A process according to any one of items 24-32, wherein one or more protein(s) are washed out as a non-bound protein with one or more washing buffer(s).

34. A process according to item 33, wherein the non-bound protein is alpha-1-proteinase inhibitor.

35. A process for the large-scale isolation of one or more protein(s) from a protein solution, said process comprising the steps of:
f) optionally adjusting the pH of the protein solution to a preset pH;
g) optionally adjusting the ionic strength or conductivity of the protein solution to a preset ionic strength or a preset conductivity;
h) applying said protein solution to an adsorption, wherein the adsorbent comprises a functionalised matrix polymer carrying a plurality of covalently attached functional groups comprising an aromatic or heteroaromatic ring-system and one or more acidic groups,
i) optionally washing the adsorbent;
j) obtaining the one or more protein(s) from the adsorbent.
wherein the protein solution has been supplemented with an alcohol.

36. A process according to item 35, wherein the protein solution is obtained from a source selected from the group consisting of blood, serum, plasma, and other blood derived sources.

37. A process according to item 36, wherein the blood, serum, plasma or other blood derived sources is obtained from humans or animals such as cows, fish, camel, pig, sheep, goat, rabbit, mouse, rat, horse, chicken, zebra or ostrich.

38. A process according to any one of items 35-37, wherein the protein solution is subjected to at least one virus elimination treatment.

39. A process according to item 38, wherein at least one virus elimination treatment is performed prior to contacting the protein solution with the adsorbent.

40. A process according to any one of items 38-39, wherein the virus elimination treatment involves addition of detergent and/or an organic solvent, such as TWEEN® polysorbates, TRITON® octylphenol ethoxylates, tri-n-butylphosphate, to the protein solution.

41. A process according to any one of items 35-40, wherein the adsorbent comprises a functionalized matrix polymer carrying a plurality of covalently attached functional groups comprising an aromatic or heteroaromatic ring-system and/or one or more acidic groups.

42. A process according to any one of items 35-41, wherein the one or more protein(s) is one or more human blood protein, such as a human plasma protein or a human serum protein.

43. A process according to any one of items 35-42, wherein said one or more human blood protein(s) is/are selected from the group consisting of albumin, IgG, IgA, IgM, IgD, IgE, alpha-1-proteinase inhibitor, blood procoagulation protein, blood anti-coagulation protein, thrombolytic agent, anti-angiogenic protein, α-2-antiplasmin, C-1 esterase inhibitor, apolipoprotein, HDL, LDL, Fibronectin, beta-2-glycoprotein I, fibrinogen, plasminogen, plasmin, plasminogen activator, plasminogen inhibitor, plasma protease inhibitor, anti-thrombin III, streptokinase, inter-alpha-trypsin inhibitor, α-2-macroglobulin, amyloid protein, ferritin, pre-albumin, GC-globulin, haemopexin, C3-complement, transferrin, urokinase, α-1-acid-glycoprotein, and the coagulation or anti-coagulation factor(s) such as Factor II, Factor V, Factor VII, Factor VIII, von Willebrand factor, Factor VIII—von Willebrand factor complex, Factor IX, Factor X, Factor XI, C1 inhibitor, protein C and/or Protein S.

44. A process according to any one of items 35-43, wherein one or more protein(s) are washed out as a non-bound protein with one or more washing buffer(s).

45. A process according to item 44, wherein the non-bound protein is alpha-1-proteinase inhibitor.

46. A process according to any one of items 35-45, wherein said adsorbent comprises a particle with at least one high density non-porous core, surrounded by a porous material.

47. A process according to any one of items 35-45, wherein the adsorbent comprises a particle density of at least 1.5 g/ml and a mean volume particle diameter of at most 150 µm.

48. A process for the large-scale isolation of one or more protein(s) from a protein solution, said process comprising the steps of:
 a) providing a protein solution comprising one or more protein(s) and said protein solution having a preset pH and a preset ionic strength or conductivity,
 b) subjecting the protein solution to at least one virus elimination treatment prior to contacting the protein solution with an adsorbent,
 c) contacting said protein solution with an adsorbent, wherein the adsorbent comprises a functionalised matrix polymer carrying a plurality of covalently attached functional groups comprising an aromatic or heteroaromatic ring-system and one or more acidic groups,
 d) optional washing the adsorbent, and
 e) obtaining said one or more protein(s) from said adsorbent.

49. A process according to item 48, wherein the virus elimination treatment involves addition of detergent and/or an organic solvent, such as TWEEN® polysorbates, TRITON® octylphenol ethoxylates, tri-n-butylphosphate, to the protein solution.

50. A process according to any one of items 48-49, wherein the protein solution is obtained from a source selected from the group consisting of blood, serum, plasma, and other blood derived sources.

51. A process according to item 50, wherein the blood, serum, plasma or other blood derived sources is obtained from humans or animals such as cows, fish, camel, pig, sheep, goat, rabbit, mouse, rat, horse, chicken, zebra or ostrich.

52. A process according to any one of items 48-51, wherein the one or more protein(s) is one or more human blood protein, such as a human plasma protein or a human serum protein.

53. A process according to any one of items 48-52, wherein said one or more human blood protein(s) is/are selected from the group consisting of albumin, IgG, IgA, IgM, IgD, IgE, alpha-1-proteinase inhibitor, blood procoagulation protein, blood anti-coagulation protein, thrombolytic agent, anti-angiogenic protein, α-2-antiplasmin, C-1 esterase inhibitor, apolipoprotein, HDL, LDL, Fibronectin, beta-2-glycoprotein I, fibrinogen, plasminogen, plasmin, plasminogen activator, plasminogen inhibitor, plasma protease inhibitor, anti-thrombin III, streptokinase, inter-alpha-trypsin inhibitor, α-2-macroglobulin, amyloid protein, ferritin, pre-albumin, GC-globulin, haemopexin, C3-complement, transferrin, urokinase, α-1-acid-glycoprotein, and the coagulation or anti-coagulation factor(s) such as Factor II, Factor V, Factor VII, Factor VIII, von Willebrand factor, Factor VIII—von Willebrand factor complex, Factor IX, Factor X, Factor XI, C1 inhibitor, protein C and/or Protein S.

54. A process according to any one of items 48-53, wherein one or more protein(s) are washed out as a non-bound protein with one or more washing buffer(s).

55. A process according to item 54, wherein one non-bound protein is alpha-1-proteinase inhibitor.

56. A process according to any one of items 48-55, wherein the protein solution has been supplemented with an alcohol.

57. A process according to any one of items 48-56, wherein said adsorbent comprises a particle with at least one high density non-porous core, surrounded by a porous material 58. A process according to any one of items 48-57, wherein the adsorbent comprises a particle density of at least 1.5 g/ml and a mean volume particle diameter of at most 150 µm.

59. A process for the large-scale isolation of one or more protein(s) from a protein solution, said process comprising the steps of:
 a) providing a protein solution comprising one or more protein(s) and said protein solution having a preset pH and a preset ionic strength or conductivity,
 b) subjecting the protein solution to at least one virus elimination treatment prior to contacting the protein solution with an adsorbent,
 c) contacting said protein solution with an adsorbent, wherein said adsorbent comprises a particle with at least one high density non-porous core, surrounded by a porous material,
 d) optional washing the adsorbent, and e) obtaining said one or more protein(s) from said adsorbent.

60. A process according to item 59, wherein the virus elimination treatment involves addition of detergent and/or an organic solvent, such as TWEEN® polysorbates, TRITON® octylphenol ethoxylates, tri-n- butylphosphate, to the protein solution.

61. A process according to any one of items 59 or 60, wherein the protein solution is obtained from a source selected from the group consisting of blood, serum, plasma, and other blood derived sources.

62. A process according to item 61, wherein the blood, serum, plasma or other blood derived sources is obtained from humans or animals such as cows, fish, camel, pig, sheep, goat, rabbit, mouse, rat, horse, chicken, zebra or ostrich.

63. A process according to any one of items 59-62, wherein the one or more protein(s) is one or more human blood protein, such as a human plasma protein or a human serum protein.

64. A process according to any one of items 59-63, wherein said one or more human blood protein(s) is/are selected from the group consisting of albumin, IgG, IgA, IgM, IgD, IgE, alpha-1-proteinase inhibitor, blood procoagulation protein, blood anti-coagulation protein, thrombolytic agent, anti-angiogenic protein, α-2-antiplasmin, C-1 esterase inhibitor, apolipoprotein, HDL, LDL, Fibronectin, beta-2-glycoprotein I, fibrinogen, plasminogen, plasmin, plasminogen activator, plasminogen inhibitor, plasma protease inhibitor, anti-thrombin III, streptokinase, inter-alpha-trypsin inhibitor, α-2-macroglobulin, amyloid protein, ferritin, pre-albumin, GC-globulin, haemopexin, C3-complement, transferrin, urokinase, α-1-acid-glycoprotein, and the coagulation or anti-coagulation factor(s) such as Factor II, Factor V, Factor VII, Factor VIII, von Willebrand factor, Factor VIII—von Willebrand factor complex, Factor IX, Factor X, Factor XI, C1 inhibitor, protein C and/or Protein S.

65. A process according to any one of items 59-64, wherein one or more protein(s) are washed out as a non-bound protein with one or more washing buffer(s).

66. A process according to item 65, wherein one non-bound protein is alpha-1-proteinase inhibitor.

67. A process according to any one of items 59-66, wherein the protein solution has been supplemented with an alcohol.

68. A process according to any one of items 59-67, wherein the adsorbent comprises a functionalised matrix polymer carrying a plurality of covalently attached functional groups comprising an aromatic or heteroaromatic ring-system and one or more acidic groups 69. A process according to any one of items 59-68, the adsorbent comprises a particle density of at least 1.5 g/ml and a mean volume particle diameter of at most 150 μm.

70. A process for the large-scale isolation or separation of α-1 proteinase inhibitor comprising the steps of:
　a) providing a protein solution comprising said α-1 proteinase inhibitor and having a preset pH and optionally a preset ionic strength or conductivity;
　b) contacting said protein solution with an adsorbent, wherein the adsorbent comprises a functionalized matrix polymer carrying a plurality of covalently attached functional groups comprising an aromatic or heteroaromatic ring-system and one or more acidic groups; and
　c) obtaining said α-1 proteinase inhibitor from said adsorbent.

71. A process according to item 70, wherein the protein solution is subjected to at least one virus elimination treatment.

72. A process according to item 71, wherein at least one virus elimination treatment is performed prior to contacting the protein solution with the adsorbent.

73. A process according to any one of items 70-72, wherein the virus elimination treatment involves addition of detergent and/or an organic solvent, such as TWEEN® polysorbates, TRITON® octylphenol ethoxylates, tri-n-butylphosphate, to the protein solution.

74. A process according to any one of items 70-73, wherein the protein solution is obtained from a source selected from the group consisting of blood, serum, plasma, and other blood derived sources.

75. A process according to item 74, wherein the blood, serum, plasma or other blood derived sources is obtained from humans or animals such as cows, fish, camel, pig, sheep, goat, rabbit, mouse, rat, horse, chicken, zebra or ostrich.

76. A process according to any one of items 70-75, wherein the protein solution has been supplemented with an alcohol.

77. A process according to any one of items 70-76, wherein said adsorbent comprises a particle with at least one high density non-porous core, surrounded by a porous material.

78. A process according to any one of items 70-77, wherein the adsorbent comprises a particle density of at least 1.5 g/ml and a mean volume particle diameter of at most 150 μm.

79. A process for the large-scale isolation or separation of α-1 proteinase inhibitor comprising the steps of:
　a) providing a protein solution comprising said α-1 proteinase inhibitor and having a preset pH and optionally a preset ionic strength or conductivity;
　b) contacting said protein solution with an adsorbent, said adsorbent comprises a particle with at least one high density non-porous core, surrounded by a porous material; and
　c) obtaining said α-1 proteinase inhibitor from said adsorbent.

80. A process according to item 79, wherein the adsorbent comprises a particle density of at least 1.5 g/ml and a mean volume particle diameter of at most 150 μm.

81. A process according to any one of items 79-80, wherein the protein solution is subjected to at least one virus elimination treatment.

82. A process according to item 81, wherein at least one virus elimination treatment is performed prior to contacting the protein solution with the adsorbent.

83. A process according to any one of items 81 or 82, wherein the virus elimination treatment involves addition of detergent and/or an organic solvent, such as TWEEN® polysorbates, TRITON® octylphenol ethoxylates, tri-n-butylphosphate, to the protein solution.

84. A process according to any one of items 80-83, wherein the adsorbent comprises a functionalized matrix polymer carrying a plurality of covalently attached functional groups comprising an aromatic or heteroaromatic ring-system and/or one or more acidic groups.

85. A process according to any one of items 79-84, wherein the protein solution is obtained from a source selected from the group consisting of blood, serum, plasma, and other blood derived sources.

86. A process according to item 85, wherein the blood, serum, plasma or other blood derived sources is obtained from humans or animals such as cows, fish, camel, pig, sheep, goat, rabbit, mouse, rat, horse, chicken, zebra or ostrich.

87. A process according to any one of items 79-86, wherein the protein solution has been supplemented with an alcohol.

88. A process according to any one of items 70-87, wherein alpha-1-proteinase inhibitor is washed out as a non-bound protein with one or more washing buffer(s).

89. A process for the large-scale isolation or separation of human albumin comprising the steps of:
  a) providing a protein solution comprising said human albumin and having a preset pH and optionally a preset ionic strength or conductivity;
  b) contacting said protein solution with an adsorbent, wherein the adsorbent comprises a functionalized matrix polymer carrying a plurality of covalently attached functional groups comprising an aromatic or heteroaromatic ring-system and one or more acidic groups; and
  c) obtaining said human albumin from said adsorbent.

90. A process according to item 89 wherein the protein solution is subjected to at least one virus elimination treatment.

91. A process according to item 90, wherein at least one virus elimination treatment is performed prior to contacting the protein solution with the adsorbent.

92. A process according to any one of items 90 or 91, wherein the virus elimination treatment involves addition of detergent and/or an organic solvent, such as tween, triton, tri-n-butylphosphate, to the protein solution.

93. A process according to any one of items 89-92, wherein the protein solution is obtained from a source selected from the group consisting of blood, serum, plasma, and other blood derived sources.

94. A process according to item 93, wherein the blood, serum, plasma or other blood derived sources is obtained from humans or animals such as cows, fish, camel, pig, sheep, goat, rabbit, mouse, rat, horse, chicken, zebra or ostrich.

95. A process according to any one of items 89-94, wherein the protein solution has been supplemented with an alcohol.

96. A process according to any one of items 89-95, wherein said adsorbent comprises a particle with at least one high density non-porous core, surrounded by a porous material.

97. A process according to any one of items 89-96, wherein the adsorbent comprises a particle density of at least 1.5 g/ml and a mean volume particle diameter of at most 150 µm.

98. A process according to any one of items 89-97, wherein human albumin is washed out as a non-bound protein with one or more washing buffer(s).

99. A process for the large-scale isolation or separation of fibrinogen comprising the steps of:
  a) providing a protein solution comprising said fibrinogen and having a preset pH and optionally a preset ionic strength or conductivity;
  b) contacting said protein solution with an adsorbent, wherein the adsorbent comprises a functionalized matrix polymer carrying a plurality of covalently attached functional groups comprising an aromatic or heteroaromatic ring-system and one or more acidic groups; and
  c) obtaining said fibrinogen from said adsorbent.

100. A process according to item 99, wherein the protein solution is subjected to at least one virus elimination treatment.

101. A process according to item 100, wherein at least one virus elimination treatment is performed prior to contacting the protein solution with the adsorbent.

102. A process according to any one of items 100 or 101, wherein the virus elimination treatment involves addition of detergent and/or an organic solvent, such as tween, triton, tri-n-butylphosphate, to the protein solution.

103. A process according to any one of items 99-102, wherein the protein solution is obtained from a source selected from the group consisting of blood, serum, plasma, and other blood derived sources.

104. A process according to item 103, wherein the blood, serum, plasma or other blood derived sources is obtained from humans or animals such as cows, fish, camel, pig, sheep, goat, rabbit, mouse, rat, horse, chicken, zebra or ostrich.

105. A process according to any one of items 99-104, wherein the protein solution has been supplemented with an alcohol.

106. A process according to any one of items 99-105, wherein said adsorbent comprises a particle with at least one high density non-porous core, surrounded by a porous material.

107. A process according to any one of items 99-106, wherein the adsorbent comprises a particle density of at least 1.5 g/ml and a mean volume particle diameter of at most 150 µm.

108. A process for the large-scale isolation or separation of fibrinogen comprising the steps of:
  a) providing a protein solution comprising said fibrinogen and having a preset pH and optionally a preset ionic strength or conductivity;
  b) contacting said protein solution with an adsorbent, said adsorbent comprises a particle with at least one high density non-porous core, surrounded by a porous material; and
  c) obtaining said fibrinogen from said adsorbent.

109. A process according to item 108, wherein the adsorbent comprises a particle density of at least 1.5 g/ml and a mean volume particle diameter of at most 150 µm.

110. A process according to any one of items 108-109, wherein the protein solution is subjected to at least one virus elimination treatment.

111. A process according to item 110, wherein at least one virus elimination treatment is performed prior to contacting the protein solution with the adsorbent.

112. A process according to any one of items 110 or 111, wherein the virus elimination treatment involves addition of detergent and/or an organic solvent, such as tween, triton, tri-n-butylphosphate, to the protein solution.

113. A process according to any one of items 108-112, wherein the adsorbent comprises a functionalized matrix polymer carrying a plurality of covalently attached functional groups comprising an aromatic or heteroaromatic ring-system and/or one or more acidic groups.

114. A process according to any one of items 108-113, wherein the protein solution has been supplemented with an alcohol.

115. A process according to any one of items 108-114, wherein fibrinogen is washed out as a non-bound protein with one or more washing buffer(s).

116. A process for the large-scale isolation or separation of transferrin comprising the steps of:

a) providing a protein solution comprising said transferrin and having a preset pH and optionally a preset ionic strength or conductivity;
b) contacting said protein solution with an adsorbent, wherein the adsorbent comprises a functionalized matrix polymer carrying a plurality of covalently attached functional groups comprising an aromatic or heteroaromatic ring-system and one or more acidic groups; and
c) obtaining said transferrin from said adsorbent.

117. A process according to item 116 wherein the protein solution is subjected to at least one virus elimination treatment.

118. A process according to item 117, wherein at least one virus elimination treatment is performed prior to contacting the protein solution with the adsorbent.

119. A process according to any one of items 117 or118, wherein the virus elimination treatment involves addition of detergent and/or an organic solvent, such as tween, triton, tri-n-butylphosphate, to the protein solution.

120. A process according to any one of items 116-119, wherein the protein solution is obtained from a source selected from the group consisting of blood, serum, plasma, and other blood derived sources.

121. A process according to item 120, wherein the blood, serum, plasma or other blood derived sources is obtained from humans or animals such as cows, fish, camel, pig, sheep, goat, rabbit, mouse, rat, horse, chicken, zebra or ostrich.

122. A process according to any one of items 116-121, wherein the protein solution has been supplemented with an alcohol.

123. A process according to any one of items 116-122, wherein said adsorbent comprises a particle with at least one high density non-porous core, surrounded by a porous material.

124 . A process according to any one of items 116-123, wherein the adsorbent comprises a particle density of at least 1.5 g/ml and a mean volume particle diameter of at most 150 μm.

125. A process for the large-scale isolation or separation of transferrin comprising the steps of:
a) providing a protein solution comprising said transferrin and having a preset pH and optionally a preset ionic strength or conductivity;
b) contacting said protein solution with an adsorbent, said adsorbent comprises a particle with at least one high density non-porous core, surrounded by a porous material; and
c) obtaining said transferrin from said adsorbent.

126 A process according to item 125, wherein the adsorbent comprises a particle density of at least 1.5 g/ml and a mean volume particle diameter of at most 150 μm.

127. A process according to any one of items 125-126, wherein the protein solution is subjected to at least one virus elimination treatment.

128. A process according to item 127, wherein at least one virus elimination treatment is performed prior to contacting the protein solution with the adsorbent.

129. A process according to any one of items 127 or 128, wherein the virus elimination treatment involves addition of detergent and/or an organic solvent, such as tween, triton, tri-n-butylphosphate, to the protein solution.

130. A process according to any one of items 125-129, wherein the adsorbent comprises a functionalized matrix polymer carrying a plurality of covalently attached functional groups comprising an aromatic or heteroaromatic ring-system and/or one or more acidic groups.

131. A process according to any one of items 125-130, wherein the protein solution is obtained from a source selected from the group consisting of blood, serum, plasma, and other blood derived sources.

132. A process according to item 131, wherein the blood, serum, plasma or other blood derived sources is obtained from humans or animals such as cows, fish, camel, pig, sheep, goat, rabbit, mouse, rat, horse, chicken, zebra or ostrich.

133. A process according to any one of items 125-132, wherein the protein solution has been supplemented with an alcohol.

134. A process according to any one of items 125-133, wherein transferrin is washed out as a non-bound protein with one or more washing buffer(s).

135. A process for the large-scale isolation or separation of α-1-acid-glycoprotein comprising the steps of:
a) providing a protein solution comprising said α-1-acid-glycoprotein and having a preset pH and optionally a preset ionic strength or conductivity;
b) contacting said protein solution with an adsorbent, wherein the adsorbent comprises a functionalized matrix polymer carrying a plurality of covalently attached functional groups comprising an aromatic or heteroaromatic ring-system and one or more acidic groups; and
c) obtaining said α-1-acid-glycoprotein from said adsorbent.

136. A process according to item 135, wherein the protein solution is subjected to at least one virus elimination treatment.

137. A process according to item 136, wherein at least one virus elimination treatment is performed prior to contacting the protein solution with the adsorbent.

138. A process according to any one of items 136 or 137, wherein the virus elimination treatment involves addition of detergent and/or an organic solvent, such as tween, triton, tri-n-butylphosphate, to the protein solution.

139. A process according to any one of items 135-138, wherein the protein solution is obtained from a source selected from the group consisting of blood, serum, plasma, and other blood derived sources.

140. A process according to item 139, wherein the blood, serum, plasma or other blood derived sources is obtained from humans or animals such as cows, fish, camel, pig, sheep, goat, rabbit, mouse, rat, horse, chicken, zebra or ostrich.

141. A process according to any one of items 135-140, wherein the protein solution has been supplemented with an alcohol.

142. A process according to any one of items 135-141, wherein said adsorbent comprises a particle with at least one high density non-porous core, surrounded by a porous material, the adsorbent comprises a particle density of at least 1.5 g/ml and a mean volume particle diameter of at most 150 μm.

143. A process according to any one of items 135-142, wherein the adsorbent comprises a particle density of at least 1.5 g/ml and a mean volume particle diameter of at most 150 μm.

144. A process for the large-scale isolation or separation of α-1-acid-glycoprotein comprising the steps of:
a) providing a protein solution comprising said α-1-acid-glycoprotein and having a preset pH and optionally a preset ionic strength or conductivity;

b) contacting said protein solution with an adsorbent, said adsorbent comprises a particle with at least one high density non-porous core, surrounded by a porous material; and c) obtaining said α-1-acid-glycoprotein from said adsorbent.

145. A process according to item 144, wherein the adsorbent comprises a particle density of at least 1.5 g/ml and a mean volume particle diameter of at most 150 μm.

146. A process according to any one of items 144-145, wherein the protein solution is subjected to at least one virus elimination treatment.

147. A process according to item 146, wherein at least one virus elimination treatment is performed prior to contacting the protein solution with the adsorbent.

148. A process according to any one of items 146 or 147, wherein the virus elimination treatment involves addition of detergent and/or an organic solvent, such as TWEEN® polysorbates, TRITON® octylphenol ethoxylates, tri-n-butylphosphate, to the protein solution.

149. A process according to any one of items 144-148, wherein the adsorbent comprises a functionalized matrix polymer carrying a plurality of covalently attached functional groups comprising an aromatic or heteroaromatic ring-system and/or one or more acidic groups.

150. A process according to any one of items 144-149, wherein the protein solution is obtained from a source selected from the group consisting of blood, serum, plasma, and other blood derived sources.

151. A process according to item 150, wherein the blood, serum, plasma or other blood derived sources is obtained from humans or animals such as cows, fish, camel, pig, sheep, goat, rabbit, mouse, rat, horse, chicken, zebra or ostrich.

152. A process according to any one of items 144-51, wherein the protein solution has been supplemented with an alcohol.

153. A process according to any one of items 144-152, wherein α-1-acid-glycoprotein is washed out as a non-bound protein with one or more washing buffer(s).

154. A process for the large-scale isolation or separation of one or more coagulation or anti-coagulation factor(s) such as Factor II, Factor V, Factor VII, Factor VIII, von Willebrand factor, Factor VIII—von Willebrand factor complex, Factor IX, Factor X, Factor XI, C1 inhibitor, protein C and/or Protein S, said process comprises the steps of:
a) providing a protein solution comprising said one or more coagulation factor(s) and having a preset pH and optionally a preset ionic strength or conductivity;
b) contacting said protein solution with an adsorbent, wherein the adsorbent comprises a functionalized matrix polymer carrying a plurality of covalently attached functional groups comprising an aromatic or heteroaromatic ring-system and one or more acidic groups; and
c) obtaining said one or more coagulation factor(s) from said adsorbent.

155. A process according to item 154, wherein the protein solution is subjected to at least one virus elimination treatment.

156. A process according to item 155, wherein at least one virus elimination treatment is performed prior to contacting the protein solution with the adsorbent.

157. A process according to any of items 155-156, wherein the virus elimination treatment involves addition of detergent and/or an organic solvent, such as TWEEN® polysorbates, TRITON® octylphenol ethoxylates, tri-n-butylphosphate, to the protein solution.

158. A process according to any one of items 154-157, wherein the protein solution is obtained from a source selected from the group consisting of blood, serum, plasma, and other blood derived sources.

159. A process according to item 158, wherein the blood, serum, plasma or other blood derived sources is obtained from humans or animals such as cows, fish, camel, pig, sheep, goat, rabbit, mouse, rat, horse, chicken, zebra or ostrich.

160. A process according to any one of items 154-159, wherein the protein solution has been supplemented with an alcohol.

161. A process according to any one of items 154-160, wherein said adsorbent comprises a particle with at least one high density non-porous core, surrounded by a porous material.

162. A process according to any one of items 154-1161, wherein the adsorbent comprises a particle density of at least 1.5 g/ml and a mean volume particle diameter of at most 150 μm.

163. A process for the large-scale isolation or separation of one or more coagulation or anti-coagulation factor(s) such as Factor II, Factor V, Factor VII, Factor VIII, von Willebrand factor, Factor VIII—von Willebrand factor complex, Factor IX, Factor X, Factor XI, C1 inhibitor, protein C and/or Protein S, said process comprises the steps of:
a) providing a protein solution comprising said one or more coagulation factor(s) and having a preset pH and optionally a preset ionic strength or conductivity;
b) contacting said protein solution with an adsorbent, said adsorbent comprises a particle with at least one high density non-porous core, surrounded by a porous material; and
c) obtaining said one or more coagulation factor(s) from said adsorbent.

164. A process according to item 163, wherein the adsorbent comprises a particle density of at least 1.5 g/ml and a mean volume particle diameter of at most 150 μm.

165. A process according to any one of items 163-164, wherein the protein solution is subjected to at least one virus elimination treatment.

166. A process according to item 165, wherein at least one virus elimination treatment is performed prior to contacting the protein solution with the adsorbent.

167. A process according to any one of items 165 or 166, wherein the virus elimination treatment involves addition of detergent and/or an organic solvent, such as TWEEN® polysorbates, TRITON® octylphenol ethoxylates, tri-n-butylphosphate, to the protein solution.

168. A process according to any one of items 164-167, wherein the adsorbent comprises a functionalized matrix polymer carrying a plurality of covalently attached functional groups comprising an aromatic or heteroaromatic ring-system and/or one or more acidic groups.

169. A process according to any one of items 164-168, wherein the protein solution is obtained from a source selected from the group consisting of blood, serum, plasma, and other blood derived sources.

170. A process according to item 169, wherein the blood, serum, plasma or other blood derived sources is obtained from humans or animals such as cows, fish, camel, pig, sheep, goat, rabbit, mouse, rat, horse, chicken, zebra or ostrich.

171. A process according to any one of items 164-1170, wherein the protein solution has been supplemented with an alcohol.

172. A process according to any one of items 154-171, wherein one or more coagulation factor(s) is washed out as a non-bound protein with one or more washing buffer(s).

173. A process for the simultaneous large-scale isolation of at least 3, e.g. 4, such as 5, e.g. 6 of the protein(s) selected from α-1 proteinase inhibitor, IgG, human albumin, transferrin, α-1-acid-glycoprotein and fibrinogen, said process comprises the steps of:
  a) providing a protein solution comprising at least three of said α-1 proteinase inhibitor, IgG, human albumin, transferrin, α-1-acid-glycoprotein and fibrinogen and said protein solution having a preset pH and optionally a preset ionic strength or conductivity;
  b) contacting said protein solution with an adsorbent; and
  c) obtaining from said adsorbent at least 3, e.g. 4, such as 5, e.g. 6 of the proteins selected from the group consisting of α-1 proteinase inhibitor, IgG, human albumin, transferrin, α-1-acid-glycoprotein and fibrinogen separated from each other in individual protein fractions.

174. A process according to item 173, wherein the protein solution is subjected to at least one virus elimination treatment.

175. A process according to item 174, wherein at least one virus elimination treatment is performed prior to contacting the protein solution with the adsorbent.

176. A process according to any one of items 174-175, wherein the virus elimination treatment involves addition of detergent and/or an organic solvent, such as TWEEN® polysorbates, TRITON® octylphenol ethoxylates, tri-n-butylphosphate, to the protein solution.

177. A process according to any one of items 173-176, wherein the protein solution is obtained from a source selected from the group consisting of blood, serum, plasma, and other blood derived sources.

178. A process according to item 177, wherein the blood, serum, plasma or other blood derived sources is obtained from humans or animals such as cows, fish, camel, pig, sheep, goat, rabbit, mouse, rat, horse, chicken, zebra or ostrich.

179. A process according to any one of items 173-178, wherein the protein solution has been supplemented with an alcohol.

180. A process according to any one of items 173-179, wherein the adsorbent comprises a functionalized matrix polymer carrying a plurality of covalently attached functional groups comprising an aromatic or heteroaromatic ring-system and/or one or more acidic groups.

181. A process according to any one of items 173-180, wherein said adsorbent comprises a particle with at least one high density non-porous core, surrounded by a porous material.

182. A process according to any one of items 173-181, wherein the adsorbent comprises a particle density of at least 1.5 g/ml and a mean volume particle diameter of at most 150 μm.

183. A process according to any one of the preceding items, wherein the high-density adsorbent is equilibrated with one or more equilibration buffers.

184. A process according to any one of the preceding items, wherein in the adsorbent after being contacted with the protein solution is washed with a washing buffer to wash out non-bound material.

185. A process according to any one of the preceding items, wherein the process further comprises the step of:
  subjecting the adsorbent to an elution buffer to elute one or more protein(s).

186. A process according to item 185, wherein the process further comprises the step of:
  repeating the step of subjecting the adsorbent to one or more additional elution buffer(s) to elute one or more remaining protein(s).

187. A process according to any one of the preceding items, wherein the protein obtained is subjected to further down stream processing for further isolation.

188. A process according to any one of the preceding items, wherein the preset pH is in the range of pH 3.0 to pH 10.0.

189. A process according to any one of the preceding items, wherein the pH-value during the entire process (for capturing and for elution) is maintained in the range of pH 3.0 to pH 10.0.

190. A process according to any one of the preceding items, wherein the preset ionic strength is in the range of 0.0001 to 12.0.

191. A process according to any one of the preceding items, wherein the preset conductivity is in the range of 0.01 to 1000 mS/cm.

192. A process according to any one of the preceding items, wherein the density of the adsorbent is in the range of 1.5 to 20 g/ml.

193. A process according to any one of the preceding items, wherein 85% by volume of the individual particles of the adsorbent have a diameter within the range of 5 to 200 micron.

194. A process according to any one of the preceding items, wherein the mean volume particle diameter of the adsorbent is 150 micron or less.

195. A process according to any one of the preceding items, wherein the density of the adsorbent is in the range of 1.5 to 10.0, 85% by volume of the individual particles of the adsorbent have a diameter within the range of 10 to 150 micron, and the mean volume particle diameter is in the range of 15 to 100 micron.

196. A process according to any one of the preceding items, wherein the adsorbent has a particle accessible protein binding volume of at least 20%.

197. A process according to any one of the preceding items, wherein the linear liquid flow rate through the column is at least 2 cm/min.

198. A process according to any one of the preceding items, wherein the temperature of the protein solution is in the range of −5 to 50° C.

199. A process according to any one of the preceding items, wherein the adsorbent has a dynamic binding capacity at 10% break-through for said at least one specific protein of at least 5 g per liter sedimented adsorbent.

200. A process according to any one of the preceding items, wherein the adsorbent comprises a functionalized matrix polymer carrying a plurality of covalently attached functional groups, said groups having the general formula:

M-SP1-X-Alk, wherein M designates the adsorbent polymer; SP1 designates an optional spacer optionally substituted with -A-SP2-ACID, -A, or -ACID; X designates —O—, —S—, —NH—, or —NAlk-; Alk may be absent, -A-SP2-ACID, -A, -ACID or $C_{1-4}$ alkyl, where $C_{1-4}$ alkyl may be optionally substituted with -A-SP2-ACID, -A, or -ACID; A designates an optionally substituted aromatic or heteroaromatic moiety; SP2 designates an optional spacer; and ACID designates one or more acidic groups; wherein at least one of SP1 or Alk is substituted with -A-SP2-ACID or -A, and at least one of SP1 or Alk comprise -ACID and wherein at least one of SP1 or Alk is present. If Alk is absent, X will also be absent.

201. A process according to any one of the preceding items, wherein the adsorbent is coupled with a ligand comprising an aromatic or heteroaromatic acid.

202. A process according to item 201, wherein the ligand is an aromatic or heteroaromatic acid selected from the group consisting of carboxylic acids, sulfonic acids, phosphonic acids, and boronic acids.

203. A process according to any of the items 200-202, wherein the ligand is coupled to the adsorbent through a thio-ether linkage, an amine linkage, or an oxygen-ether linkage.

204. A process according to any of the items 200-203, wherein the ligand is chosen from the group consisting of 2-mercaptobenzoic acid, 2-mercaptonicotinic acid, 2-aminobenzoic acid, 3-aminobenzoic acid, 4-aminobenzoic acid, 4-hydroxyphenyl-mercapto-acetic acid, 4-hydroxyphenyl-mercapto-propionic acid, 4-hydroxyphenyl-mercapto-butanoic acid, 2,3-dihydroxy-benzoic acid, 2,4 dihydroxy-benzoic acid, 2,5 di-hydroxy-benzoic acid, 2,6 dihydroxy-benzoic acid, 3,4-dihydroxy-benzoic acid, 3,5-dihydroxy-benzoic acid and mercaptobenzimidazole sulfonic acid.

205. A process according to any one of the preceding items, wherein the adsorbent is coupled to a ligand comprising a bicyclic substituted heteroaromatic group.

206. A process according to item 205, wherein the ligand is derived from compounds selected from the group consisting of benzimidazoles, benzothiazoles, and benzoxazoles.

207. A process according to any one of the preceding items, wherein the adsorbent is coupled with a ligand carrying a positive charge at pH values lower than pH 10.

208. A process according to any one of the preceding items, wherein the ligand is derived from a diethylaminoethyl group, a polyalkylene imine, an alkyl-amine, an alkyl-diamine or a polyallylamine.

209. A process according to item 208, wherein the alkyl-amine or alkyl-diamine has a chain-length of 3-14 atoms and 1-5 functional amine groups.

210. A process according to any one of the preceding items, wherein the adsorbent comprises a ligand which is an aromatic amine or an aromatic diamine.

211. A process according to item 212, wherein the aromatic diamine is 1,4-xylene-diamine or isomers of 1,4-xylene-diamine.

212. A process according to any one of the preceding items, wherein at least 2, such as 3, e.g. 4, such as 5, e.g. 6 of the protein(s) selected from the group consisting of albumin, IgG, IgA, IgM, IgD, IgE, alpha-1-proteinase inhibitor, blood pro-coagulation protein, blood anti-coagulation protein, thrombolytic agent, anti-angiogenic protein, α-2-antiplasmin, C-1 esterase inhibitor, apolipoprotein, HDL, LDL, Fibronectin, beta-2-glycoprotein I, fibrinogen, plasminogen, plasmin, plasminogen activator, plasminogen inhibitor, plasma protease inhibitor, anti-thrombin III, streptokinase, inter-alpha-trypsin inhibitor, α-2-macroglobulin, amyloid protein, ferritin, pre-albumin, GC-globulin, haemopexin, C3-complement, transferrin, urokinase, α-1-acid-glycoprotein, and the coagulation or anti-coagulation factor(s) such as Factor II, Factor V, Factor VII, Factor VIII, von Willebrand factor, Factor VIII—von Willebrand factor complex, Factor IX, Factor X, Factor XI, C1 inhibitor, protein C and/or Protein S are separated simultaneously from each other in at least 2, such as 3, e.g. 4, such as 5, e.g. 6 individual protein fractions.

213. A process according to any one of the preceding items, wherein at least 2, such as 3, e.g. 4, such as 5, e.g. 6 of the protein(s) selected from α-1 proteinase inhibitor, IgG, human albumin, transferrin, thrombin, Factor II, Factor V, Factor VII, Factor VIII, Factor IX, protein C, Protein S, α-1-acid-glycoprotein and fibrinogen are separated simultaneously from each other in at least 2, such as 3, e.g. 4, such as 5, e.g. 6 individual protein fractions.

214. A process according to any one of the preceding items, wherein fibrinogen is bound to the adsorbent and simultaneously one or more of the coagulation or anti-coagulation factor(s) such as Factor II, Factor V, Factor VII, Factor VIII, von Willebrand factor, Factor VIII—von Willebrand factor complex, Factor IX, Factor X, Factor XI, C1 inhibitor, protein C and/or Protein S is obtained as non-bound material from the adsorbent.

215. A process according to item 214, wherein at least 40% of the fibrinogen bind to the adsorbent.

216. A process according to any one of the preceding items, wherein albumin and IgG are bound to the adsorbent and simultaneously α-1-proteinase inhibitor is obtained as non-bound material from the adsorbent.

217. A process according to item 216, wherein albumin and IgG is obtained from the adsorbent by stepwise elution.

218. A process according to any one of items 216 or 217, wherein at least 50% of the albumin bind to the adsorbent and/or at least 50% of the IgG bind to the adsorbent.

219. A process according to any one of the preceding items, wherein fibrinogen and IgG are bound to the adsorbent and simultaneously albumin may be obtained as non-bound material from the adsorbent.

220. A process according to item 219, wherein fibrinogen and IgG may be obtained from the adsorbent by stepwise elution.

221. A process according to any one of items 219 or 220, wherein at least 50% of the IgG bind to the adsorbent and/or at least 50% of the fibrinogen bind to the adsorbent.

222. A process according to any one of the preceding items, wherein fibrinogen, albumin and IgG are bound to the adsorbent and simultaneously α-1-proteinase inhibitor is obtained as non-bound material from the adsorbent.

223. A process according to item 222, wherein fibrinogen, albumin and IgG are obtained from the adsorbent by stepwise elution.

224. A process according to any one of items 222 or 223, wherein at least 50% of the IgG bind to the adsorbent and/or at least 50% of the fibrinogen bind to the adsorbent and/or at least 50% of the albumin bind to the adsorbent.

225. A process according to any one of the preceding items, wherein at least 1, such as at least 2 e.g. 3 of fibrinogen, albumin and IgG is/are bound to the adsorbent and simultaneously α-1-acid glycoprotein is obtained as non-bound material from the adsorbent.

226. A process according to item 225, wherein fibrinogen, albumin and/or IgG is/are obtained from the adsorbent by stepwise elution.

227. A process according to any one of items 225 or 226, wherein at least 50% of the IgG bind to the adsorbent and/or at least 50% of the fibrinogen bind to the adsorbent and/or at least 50% of the albumin bind to the adsorbent.

228. A process according to any one of the preceding items, wherein at least 1, such as at least 2 e.g. 3 of fibrinogen, albumin and IgG is/are bound to the adsorbent and simultaneously α-1-acid glycoprotein and/or α-1-proteinase inhibitor is/are obtained as non-bound material from the adsorbent.

229. A process according to item 230, wherein fibrinogen, albumin and/or IgG may be obtained from the adsorbent by stepwise elution.

230. A process according to any one of items 228 or 229, wherein at least 50% of the IgG bind to the adsorbent and/or at least 50% of the fibrinogen bind to the adsorbent and/or at least 50% of the albumin bind to the adsorbent.

231. A process according to any one of the preceding items, wherein least 50% α-1-proteinase inhibitor, albumin, IgG, fibrinogen or one or more coagulation or anti-coagulation factor(s), such as Factor II, Factor V, Factor VII, Factor VIII, von Willebrand factor, Factor VIII—von Willebrand factor complex, Factor IX, Factor X, Factor XI, C1 inhibitor, protein C and/or Protein S is/are obtained from the adsorbent.

232. A process according to any one of the preceding items, wherein the yield if the protein of interest is at least 60%

233. A process according to any one of the preceding items, wherein the content of protein(s) other than the protein of interest is at most 20%.

234. A process according to any of the preceding items, wherein the proteins from the group consisting of IgG, albumin, fibrinogen, α-1-proteinase inhibitor, α-1-acid-glycoprotein, and one or more coagulation or anti-coagulation factor(s) such as Factor II, Factor V, Factor VII, Factor VIII, von Willebrand factor, Factor VIII—von Willebrand factor complex, Factor IX, Factor X, Factor XI, C1 inhibitor, protein C and/or Protein S, is/are isolated in at least 2 individual protein fractions, such as 3 individual protein fractions, e.g. 4 individual protein fractions, such as 5 individual protein fractions, e.g. 6 individual protein fractions.

235. A process according to item 234, wherein the degree of cross-contamination of the individual protein in the protein fraction is at the most 20%.

236. A process according to any one of the preceding items, wherein the adsorbent is an adsorbent particle.

237. A process according to item 236, wherein the adsorbent particle is held in an expanded bed column, a suspended bed column, a continuously stirred tank contactor, a turbulent fluidised bed column, a stirred tank or in a packed bed column.

238. A process according to item 237, wherein the adsorbent particle is held in an expanded bed column and the adsorbent particles has a degree of expansion, determined by H/H0, in the range of 1.0-20.

239. A process according to any one of the preceding items, wherein the protein solution may comprise a supernatant and a precipitated fraction after being supplemented with an alcohol.

240. A process according to item 239, wherein the supernatant and the precipitated fraction are separated by filtration, microfiltration, centrifugation, decantation, and/or sedimentation.

241. A process according to item 240, wherein the one or more protein(s) is found in the supernatant.

242. A process according to item 240, wherein the one or more protein(s) is found in the precipitated fraction.

243. A process according to any of items 239-242, wherein the supernatant or the precipitated fraction has a concentration of alcohol of at least 0.1% by volume.

244. A process according to any one of items 239-243, wherein said alcohol is selected from the group consisting of methanol, ethanol, n-propanol, i-propanol, n-butanol, i-butanol, s-butanol, t-butanol, methylene glycol, ethylene glycol, propylene glycol, diethylene glycol, methylene-ethylene glycol, and dimethylene glycol.

245. A process according to any one of items 239-244, wherein the precipitated fraction is a resolubilised precipitate obtained by the addition of alcohol to blood, plasma, serum or other blood derived sources.

246. A process according to item 245, wherein the blood, serum, plasma or other blood derived sources is obtained from humans or animals such as cows, fish, camel, pig, sheep, goat, rabbit, mouse, rat, horse, chicken, zebra or ostrich.

247. A process according to any one of items 239-246, wherein a protein solution is obtained by re-combination of one or more supernatants and/or one or more resolubilised precipitates obtained by the stepwise addition of alcohol to human plasma or serum.

248. A process according to any one of the preceding items, wherein said protein solution is obtained by the Cohn fractionation method or a variation hereof.

249. A process according to any one of items 245-254, wherein the protein solution is selected from the group consisting of supernatant I, supernatant II, supernatant III, resolubilized fraction IV-1, re-solubilized fraction I, resolubilized fraction II, resolubilized fraction III and any combination thereof.

250. A process according to any one of items 239-248, wherein the protein solution is selected from the group consisting of, supernatant II+III, supernatant I+II+III, resolubilized fraction II+III and resolubilized Fraction I+II+III.

251. A process according to any of the preceding items, wherein 2 or more proteins from the protein solution are isolated by the means of a cascade of 2 or more adsorbents.

252. A process according to item 251, wherein:
d) the first adsorbent is capable of capturing one or more blood protein(s), serum protein(s) or plasma protein(s);
e) the second adsorbent is capable of capturing one or more blood protein(s), serum protein(s) or plasma protein(s) different for the one or more blood protein(s), serum protein(s) or plasma protein(s) capable of being captured to the first adsorbent; and
f) the third adsorbent is capable of capturing one or more blood protein(s), serum protein(s) or plasma protein(s) different for the one or more blood protein(s), serum protein(s) or plasma protein(s) capable of being captured to the first adsorbent or second adsorbent;

253. A process according to any one of items 251 or 252, wherein the protein solution is blood, serum, plasma or cryopoor plasma.

254. A process according to item 253, wherein the blood is obtained from humans or animals such as cows, fish, camel, pig, sheep, goat, rabbit, mouse, rat, horse, chicken, zebra or ostrich.

255. A process according to any one of items 251-254, wherein one or more coagulation or anti-coagulation factor(s), such as Factor II, Factor V, Factor VII, Factor VIII, von Willebrand factor, Factor VIII—von Willebrand factor complex, Factor IX, Factor X, Factor XI, C1 inhibitor, protein C and/or Protein S, is/are bound to a first adsorbent.

256. A process according to item 255, wherein at least 2 of the coagulations factors binds to the adsorbent.

257. A process according to any one of items 251-256, wherein at least one of the proteins selected from albumin, IgG, tranferrin, fibrinogen is/are bound to a second adsorbent.

258. A process according to item 257, wherein at least 2 of the proteins binds to the adsorbent.

259. A process according to any of the items 251-258, wherein at least one of the proteins α-1-proteinase inhibitor or α-1-acid-glycoprotein binds to a third adsorbent.

260. A process according to item 259, wherein 2 of the proteins binds to the adsorbent.

EXAMPLES

Example 1

Separation of human albumin and alpha-1-protease inhibitor from Cohn fraction (SUP I, II, III) by expanded bed adsorption.

Adsorbent

FastLine® UFC NNSDW Cat. No. CS48, UpFront Chromatography A/S. The adsorbent was based on agarose with tungsten carbide particles incorporated, the density of the conglomerate particles was 2.9 g/ml and the particle diameter was in the range of 40-120 μm with a volume mean particle diameter (D (4,3) of 70 μm (as determined on the Mastersizer 2000E, Malvern Instruments, Worcestershire, UK). The adsorbent comprised 2-mercaptonicotinic acid as the ligand and had a ligand concentration of 40 micromoles per ml sedimented adsorbent.

Pre-Treatment of the Protein Solution

The protein solution comprised of Cohn fraction, Supernatant I, II, III, Conductivity 5,74 mS, pH 7.2, comprising approx. 10% ethanol.

The protein solution was diluted with demineralised water in a ratio of one volume of Cohn supernatant I, II, III to 2 volumes of water and pH was adjusted to pH 5.0 with 1 M hydrochloric acid. The conductivity after dilution was 3.8 mS.

Process Parameters

The experiment was performed in a FastLine® 20 expanded bed column (φ=2 cm) product number 7020-0000, UpFront Chromatography A/S.

The column was packed with 50 cm of adsorbent (157 ml) and equilibrated at room temperature (20-25° C.) with 160 ml 1 M NaOH (first equilibration buffer), 400 ml 40 mM sodium citrate buffer pH 4.5 (second equilibration buffer), and 400 ml 40 mM sodium citrate buffer pH 5.0 (third equilibration buffer).

Two experiments were performed with a linear flow rate of 450 cm/hr.:
  (i) Experiment A) 236 ml diluted protein solution was loaded onto the column
  (ii) Experiment B) 353 ml three times diluted protein solution was loaded onto the column Fraction 1: Non-bound material was washed out of the column with 10 mM citric acid buffer pH 5.0. Alpha-1-protease inhibitor was collected in the washing fraction. The bound proteins were subsequently eluted in two steps.

Fraction 2, first elution step: Human Albumin was eluted with sodium octanoate (sodium caprylate) 5 mg/ml, pH 6.0.
  Fraction 3, second elution step: Other proteins including IgG and transferrin were eluted with 0.3 M sodium citrate pH 7.4.

Results

The table below shows the volumes of protein solution and buffers loaded onto each column:

| Fraction | Run A | Run B |
| --- | --- | --- |
| First equilibration buffer | 160 ml | 160 ml |
| Second equilibration buffer | 400 ml | 400 ml |
| Third equilibration buffer | 400 ml | 400 ml |
| Protein fraction 1 Volume of wash (alpha-1-protease inhibitor) | 750 ml | 815 ml |
| Protein fraction 2 Elution of human albumin | 500 ml | 520 ml |
| Protein fraction 3 Elution of IgG and transferring | 350 ml | 390 ml |

Quantification of alpha-1-protease inhibitor and human albumin in fraction 1, 2 and 3 Single Radial Immunodiffusion (SRI) was performed in order to quantify the relative yield in percent of alpha-1-protease inhibitor and human albumin in the fractions from the column as described in Scand. J. Immunol. Vol. 17, Suppl. 10, 41-56, 1983.

The SRI was performed with: Rabbit anti-Human alpha-1-protease inhibitor from Dako Cytomation, Denmark, Cat. No.: A0012 (0.6 μl per cm$^2$) and Rabbit anti Human albumin from Dako Cytomation, Denmark, Cat. No.: A001 (0.3 μl per cm$^2$).

A standard curve was performed with the protein solution loaded onto the column in the concentration of 100%, 80%, 60%, 40% and 20%. Each of the three fractions was read relative to the standard curve.

Results:

The table below shows the relative yield in percent of the raw material loaded onto the column:

| Determination of human alpha-1-protease inhibitor | | | |
| --- | --- | --- | --- |
| Run | Protein fraction 1 Non bound material | Protein fraction 2 First eluate | Protein fraction 3 Second eluate |
| Run A | 80% | 0% | 0% |
| Run B | 80% | 0% | 0% |

| Determination of human albumin | | | |
| --- | --- | --- | --- |
| Run | Fraction 1 Non bound material | Fraction 2 First eluate | Fraction 3 Second eluate |
| Run A | 0% | 95% | 0% |
| Run B | 0% | 95% | 0% |

Each fraction from the experiment was tested with SDS-PAGE to evaluate the content and nature of the proteins.

SDS-PAGE

For SDS-PAGE, Invitrogen SDS-Page 4-20% Tris-Glycine gel (cat no. EC6025) was used.

Sample preparation: 25 μl sample and 25 μl sample buffer tris-glycine Invitrogen (cat no. LC2676) was mixed and boiled for 5 minutes in a water bath. The running buffer 0.024 M tris (Sigma T1378), 0.19 M glycine (Merck 5001901000), 0.1% SDS (sodium dodecyl sulphate, JT Baker 2811) pH 8.6 was added.

20 μl sample was applied in each analysis slot and the power was adjusted to give a current of 40 mA. When the blue line from the sample buffer reached one cm from the bottom of the gel the power was turned off and the gel was stained overnight in Invitrogen Colloidal Blue Staining Kit (cat. no. LC 6025) on a shaking table. The next day the gel was transferred into water and de-stained in water for 2 hours.

Results:

No breakdown or denaturation of the human alpha-1-protease inhibitor (alpha-1-PI) or human albumin molecules could be detected by sodiumdodecyl-gelelctrophoresis (SDS-PAGE). The purity of the eluted human albumin was found to be higher than 95% as determined by SDS-PAGE.

In fraction 1 the alpha-1-PI was recovered

In fraction 2 the bound human albumin was recovered.

In Fraction 3 the bound immunoglobulin G and transferrin was recovered.

Example 2

Separation of human albumin and alpha-1-protease inhibitor from Cohn fraction (SUP I, II and III) by expanded bed adsorption at different pH values.

Adsorbent

FastLine® UFC NNSDW Cat. No. CS48, UpFront Chromatography A/S. See example 1.

Pre-Treatment of the Protein Solution

The protein solution comprised a Cohn fraction Supernatant I, II, III, conductivity 5,74 mS, pH 7.2, comprising approx 10% ethanol.

The protein solution was diluted with demineralised water or sodium acetate 20 mM pH 5 in a ratio of one volume of Cohn supernatant I, II, III to 5 volumes of water or sodium acetate 20 mM pH 5 and pH was adjusted to different pH values with 1 M hydrochloric acid.

Process Parameters:

The experiment was performed in a FastLine® 20 expanded bed column (ϕ=2 cm) product number 7020-0000, UpFront Chromatography A/S.

Three experiments were performed with a linear flow rate of 450 cm/hr. The column was packed with 50 cm of adsorbent (157 ml) and equilibrated at room temperature (20-25° C.) with 160 ml 1 M NaOH (first equilibration buffer), 400 ml 40 mM sodium citrate buffer pH 4.5 (second equilibration buffer) followed by equilibration with a third buffer (third equilibration buffer) comprising:

Experiment A: 400 ml 40 mM sodium citrate buffer pH 5.0

Experiment B: 400 ml 40 mM sodium citrate buffer pH 5.3

Experiment C: 400 ml 40 mM sodium citrate buffer pH 5.5

240 ml diluted protein solution was adjusted with 1 M HCl to:

Experiment A: pH 5.0, conductivity=2.16 mS

Experiment B: pH 5.3, conductivity=2.27 mS

Experiment C: pH 5.5, conductivity=2.29 mS

After pH was adjusted the protein solution was loaded onto the column.

Fraction 1: Non-bound material was washed out with 10 mM sodium citrate buffer pH 5.0. alpha-1-protease inhibitor was collected in the washing fraction from the column.

The bound proteins were eluted in two steps.

Fraction 2, first elution step: Human albumin was eluted with sodium caprylate 5 mg/ml, pH 6

Fraction 3, second elution step: Other proteins including IgG and transferrin were eluted with 0.3 M sodium citrate pH 7.4.

Results

The table below shows the volumes of protein solution and buffers loaded onto each column:

| Fraction | Run A | Run B | Run C |
|---|---|---|---|
| First equilibration buffer | 160 ml | 160 ml | 160 ml |
| Second equilibration buffer (2 | 400 ml | 400 ml | 400 ml |
| Third equilibration buffer | 400 ml | 400 ml | 400 ml |
| Volume of protein solution | 240 ml | 240 ml | 240 ml |
| Protein fraction 1 | 640 ml | 640 ml | 685 ml |
| Volume of washing fraction (alpha-1-protease inhibitor) | | | |
| Protein fraction 2 | 490 ml | 430 ml | 360 ml |
| Elution of human albumin | | | |
| Protein fraction 3 | 250 ml | 210 ml | 200 ml |
| Elution of human traces of IgG and transferrin | | | |

Quantification of alpha-1-protease inhibitor and human albumin in fraction 1, 2 and 3 Single Radial Immunodiffusion (SRI) was performed in order to quantify the relative yield in percent of alpha-1-protease inhibitor and human albumin in the fractions from the column (see example 1)

Results:

The table below shows the relative yield in percent of the protein solution loaded onto the column:

| Run | Protein fraction 1 Non-bound material | Protein fraction 2 First eluate | Protein fraction 3 Second eluate |
|---|---|---|---|
| Determination of alpha-1-protease inhibitor | | | |
| Run A | 60% | 0% | 0% |
| Run B | 80% | 0% | 0% |
| Run C | No data | No data | No data |
| Determination of human albumin | | | |
| Run A | 0% | 95% | 0% |
| Run B | 20% | 80% | 0% |
| Run C | No Data | No Data | No Data |

Each fraction from the experiment was tested with SDS-PAGE to evaluate the content and nature of proteins.

SDS-PAGE (See Experiment 1)

Results:

No breakdown or denaturation of the alpha-1-protease inhibitor or albumin molecules could be detected by SDS-PAGE. The purity of the eluted Human albumin was found to be higher than 95% as determined by SDS-PAGE.

Example 3

Isolation of alpha-1-protease inhibitor from the unbound fraction obtained in example 1.

Adsorbent

FastLine® DEAE Ion Exchanger Cat. No. CS62, UpFront Chromatography A/S. The adsorbent was based on agarose with tungsten carbide particles incorporated, the density of the conglomerate particles was 2.9 g/ml and the particle diameter was in the range of 40-120 μm with a mean particle diameter of 70 μm. The adsorbent comprised diethylaminoethyl (DEAE) groups as the ligand and a ligand concentration of 150 micromoles per ml sedimented adsorbent.

Protein Solution

Protein fraction 1 (the non-bound material) from the separation of albumin and alpha-1-proteinase inhibitor as described in example 1, experiment A. The pH in the protein fraction was adjusted to pH 8.2 with 1 M NaOH. The conductivity was hereafter 6.16 mS.

Process Parameters

The experiment was performed in Poly-Prep columns product number 731-1550, BioRad.

The column was packed with 1 ml of ion exchanger and equilibrated at room temperature (20-25° C.) for 30 minutes with 5 ml 1 M potassium phosphate pH 8.2. After incubation the ion exchanger was washed with 10 ml 10 mM potassium phosphate pH 8.2. 30 ml protein fraction was adjusted to pH 8.2 and loaded onto the column and the run through fractions were collected in fractions of 5 ml. After loading of the protein fraction the column was washed with 10 ml 10 mM potassium phosphate pH 8.2

The bound alpha-L-protease inhibitor was eluted with 10 mM potassium phosphate+1 M NaCl to pH 8.2.

Results

The table below shows the volumes of raw material and buffers loaded onto the column:

| | |
|---|---|
| Fraction | 10 |
| Protein fraction | 30 ml |
| Volume of run through fractions | 6 × 5 ml |
| Wash fraction | 10 ml |
| Alpha-1-protease inhibitor, eluate | 10 ml |

Quantification of human alpha-1-protease inhibitor

Single Radial Immunodiffusion (SRI) was performed in order to quantify the relative yield in percent of alpha-1-protease inhibitor in the fractions from the column as described in Scand. J. Immunol. Vol. 17, Suppl. 10, 41-56, 1983.

The RDI was performed with: Rabbit anti-human alpha-1-protease inhibitor from Dako Cytomation, Denmark, Cat. No.: A0012 (0.6 µl per cm$^2$).

A standard row was performed with the protein fraction loaded onto the column in the concentration of 100%, 80%, 60%, 40% and 20%. Each of the fractions was read relative to the standard curve.

Results:

The table below shows the relative yield of alpha-1-protease inhibitor in percent of the protein fraction loaded onto the column:

Determination of Human Alpha-1-Protease Inhibitor

| Fraction | Relative yield |
|---|---|
| Run through protein fraction 1 | 0% |
| Run through protein fraction 2 | 0% |
| Run through protein fraction 3 | 0% |
| Run through protein fraction 4 | 0% |
| Run through protein fraction 5 | 0% |
| Run through protein fraction 6 | 0% |
| Wash | 0% |
| Eluate | 80% |

Thus, no alpha-1-protease inhibitor was found in the unbound protein fractions, while 80% of the alpha-1-protease-inhibitor loaded onto the column was found in the eluate.

Example 4

Expanded bed adsorption of alpha-1-proteinase inhibitor.

Example 3 was repeated, however, this time using an expanded bed adsorption column using the same ion exchange adsorbent at a settled bed height of 5 cm and a linear flow rate of 5 cm/min.

Again it was found that no alpha-1-protease inhibitor was found in the unbound fraction, while 80% of the alpha-1-protease-inhibitor loaded onto the column was found in the eluate.

Example 5

Isolation of human plasma proteins from human plasma by using expanded bed adsorption with a flow rate at 450 cm/hr.

Adsorbent

FastLine® UFC NNSDW Cat. No. CS48, UpFront Chromatography A/S. The adsorbent was based on agarose with tungsten carbide particles incorporated, the density of the conglomerate particles was 2.9 g/ml and the particle diameter was in the range of 40-120 µm with a mean particle diameter of 70 µm. The adsorbent comprised 2-mercaptonicotinic acid as the ligand and a ligand concentration of 40 micromoles per ml sedimented adsorbent.

Pre-Treatment of the Protein Solution

The protein solution was diluted with demineralised water in a ratio of one volume of human plasma to 2 volumes of water and pH was adjusted to pH 5.0 with 1 M hydrochloric acid. The conductivity was hereafter 5,25 mS/cm$^2$ Process Parameters:

The experiment was performed in a FastLine® 20 expanded bed column (φ=2 cm) product number 7020-0000, UpFront Chromatography A/S.

The column was loaded with adsorbent to reach a settled bed height (H0) of 50 cm (corresponding to 157 ml adsorbent) and washed and equilibrated at 20-25° C. with the following buffers in successive order [1] 160 ml 1 M NaOH, [2] 400 ml 40 mM citric acid buffer pH 4.5 [3] 400 ml 40 mM citric acid buffer pH 5.0.

The experiment was performed with a linear flow rate of 450 cm/hr in all steps and the outlet from the column was connected to an UV monitor and recorder.

Sample:

120 ml protein solution (corresponding to 40 ml undiluted plasma) was loaded onto the column.

Collection of Fractions:

Following loading of the protein solution, non-bound and weakly bound material was washed out of the column with 10 mM sodium citrate pH 5.0.

Fraction 1 (unbound fraction) was collected as one fraction according to the UV monitoring of the column effluent.

Subsequently the bound proteins were eluted in three sequential steps.

Fraction 2—first elution step was performed with sodium caprylate 5 mg/ml, pH 6.0

Fraction 3—second elution step was performed with 0.3 M sodium citrate pH 7.4.

Fraction 4—third elution step was performed with 20 mM sodium citrate+0.1 M NaCl pH 7.4

In between first and second elution step the column was briefly washed with 1 column volume of 1 M sodium citrate pH 7.4

Results

The table below shows the volumes of each fraction

| Fraction | Run |
|---|---|
| Equilibration buffer [1] | 160 ml |
| Equilibration buffer [2] | 400 ml |
| Equilibration buffer [3] | 400 ml |
| Protein fraction 1 | 900 ml |
| Non bound proteins and wash | |
| Protein fraction 2 | 550 ml |
| Protein fraction 3 | 560 ml |
| Protein fraction 4 | 370 ml |

Quantification of human plasma proteins fraction 1, 2, 3 and 4 from the column

Single Radial Immunodiffusion (SRI) was performed in order to demonstrate the components in each fraction from the column as described in Scand. J. Immunol. Vol. 17, Suppl. 10, 41-56, 1983.

The SRI was performed with the following antibodies, all from Dako Cytomation, Denmark:

| Antibody | Code no. | µl sample/well | µl per cm² |
|---|---|---|---|
| Rabbit anti human Albumin | A 0001 | 5 µl | 0.30 µl per cm² |
| Rabbit anti human IgG | A 0424 | 5 µl | 0.30 µl per cm² |
| Rabbit anti human Alpha-1-PI | A 0012 | 5 µl | 0.60 µl per cm² |
| Rabbit anti human Fibrinogen | A 0080 | 5 µl | 0.40 µl per cm² |
| Rabbit anti human Haptoglobin | A 0030 | 15 µl | 0.45 µl per cm² |
| Rabbit anti human GC-Globulin | A 0021 | 15 µl | 0.60 µl per cm² |
| Rabbit anti human IgM | A 0426 | 15 µl | 0.40 µl per cm² |
| Rabbit anti human IgA | A 0092 | 15 µl | 0.50 µl per cm² |
| Rabbit anti human Alpha-2 Macroglobulin | A 0033 | 15 µl | 0.40 µl per cm² |
| Rabbit anti human Orosomucoid | A 0011 | 5 µl | 0.80 µl per cm² |
| Rabbit anti human Transferrin | A 0061 | 5 µl | 0.30 µl per cm² |
| Rabbit anti human Prealbumin | A 0002 | 15 µl | 0.75 µl per cm² |
| Rabbit anti human Antitrombin III | A 0296 | 25 µl | 0.50 µl per cm² |

A standard curve was established with the protein solution (100% reference) loaded onto the column in the concentration of 100%, 80%, 60%, 40% and 20%. Each of the four fractions was determined relative to this standard curve.

Results

The table below shows the relative yield of each human protein in the 4 fractions from the column:

|  | Protein fraction 1 Non-bound material | Protein fraction 2 | Protein fraction 3 | Protein fraction 4 |
|---|---|---|---|---|
| human Albumin | — | 100% | — | — |
| human IgG | — | — | 95% | 5% |
| human alpha-1-PI | 90% | — | — | — |
| human Fibrinogen | — | — | 20% | 60-80% |
| human Haptoglobin | 40% | 40% | 20% | — |
| human GC-Globulin | — | 100% | — | — |
| human IgM | — | — | 80% | — |
| human IgA | 10% | 20% | 70% | — |
| human Alpha-2 Macroglobulin | — | 40% | 40% | — |
| human Orosomucoid | 100% | — | — | — |
| human Transferrin | — | — | 100% | — |
| human Prealbumin | 40% | — | — | — |
| human Antitrombin III | — | 80% | — | — |

"—" = relative yield below 5%

Example 6

Isolation human plasma proteins from ethanol-treated human plasma using expanded bed adsorption with a flow rate at 450 cm/hr.

Adsorbent

FastLine® UFC NNSDW Cat. No. CS48, UpFront Chromatography A/S. The adsorbent was based on agarose with tungsten carbide particles incorporated, the density of the conglomerate particles was 2.9 g/ml and the particle diameter was in the range of 40-120 µm with a mean particle diameter of 70 µm. The adsorbent comprised 2-mercaptonicotinic acid as the ligand and a ligand concentration of 40 micromoles per ml sedimented adsorbent.

Pre-Treatment of the Protein Solution

Human plasma was adjusted to 8% ethanol by volume with 99% ethanol at −3° C. and incubated at −3° C. for 1.5 hour. After incubation the plasma was centrifuged 10 minutes. The supernatant was diluted demineralised water in a ratio of 1 part of plasma to two parts of water and the pH was adjusted to pH 5.0 with 1 M hydrochloric acid. The conductivity was hereafter 4.16 mS/cm²

Process Parameters, Sample Volume and Fractions

All process parameters and conditions were identical to those applied in example 5

Results

The table below shows the volumes of each fraction:

| Fraction | Run |
|---|---|
| Equilibration buffer (1 | 160 ml |
| Equilibration buffer (2 | 400 ml |
| Equilibration buffer (3 | 400 ml |
| Protein fraction 1 | 900 ml |
| Non bound proteins and wash | |
| Protein fraction 2 | 530 ml |
| Protein fraction 3 | 570 ml |
| Protein fraction 4 | 250 ml |

Quantification of human plasma proteins fraction 1, 2, 3 and 4 from the column Analysis by SRI was performed as in example 5.

Results

The table below shows the yield of each human protein in the 4 fractions from the column relative to the total amount of the protein applied to the column:

|  | Protein fraction 1 Non-bound material | Protein fraction 2 | Protein fraction 3 | Protein fraction 4 |
|---|---|---|---|---|
| human Albumin | — | 100% | — | — |
| human IgG | — | — | 95% | 5% |
| human alpha-1-PI | 90% | — | — | — |
| human Fibrinogen | — | — | 20% | 60% |
| human Haptoglobin | 40% | 40% | 20% | — |
| human GC-Globulin | — | 100% | — | — |
| human IgM | — | — | 60% | — |
| human IgA | 10% | 20% | 60% | — |
| human Alpha-2 Macroglobulin | — | 50% | 20% | — |
| human Orosomucoid | 100% | — | — | — |
| human Transferrin | — | — | 100% | — |
| human Prealbumin | 40% | 20% | — | — |
| human Antitrombin III | — | 80% | — | — |

"—" = relative yield below 5%

Example 7

Isolation of human alpha-1-protease inhibitor (API) from non-bound fraction of example 5.

Adsorbent

FastLine® DEAE Ion Exchanger Cat. No. CS62, UpFront Chromatography A/S.

The ion exchanger was based on 4% agarose with tungsten carbide particles incorporated. The conglomerate beads had a density of approximately 2.9 g/ml and a particle size in the range of 40-120 µm with a mean particle size (diameter) of 70 µm. The adsorbent comprised DEAE (diethylaminoethyl-) groups and a concentration of approx. 150 millimole per litre sedimented adsorbent Protein Solution The starting material for this experiment was protein fraction 1 (the non-bound material) obtained from isolation of human plasma proteins using expanded bed adsorption as described in example 5. The pH in the protein fraction was carefully adjusted to pH 8.2 with 1 M NaOH. The conductivity was hereafter 5,15 mS/cm$^2$ Process Parameters:

The experiment was performed as packed bed experiments in Poly-Prep columns product number 731-1550, BioRad, USA.

All steps were performed at a flow rate of 1 ml/minute.

The column was packed with 1 ml of DEAE ion exchanger and equilibrated, at 20-25° C., with 5 ml 1 M $K_2$ $HPO_4$ adjusted to pH 8.2 with 1 M NaOH. After equilibration the ion exchanger was washed with 10 ml 10 mM potassium phosphate pH 8.2.

50 ml of the raw material adjusted to pH 8.2 was loaded onto the column and the run through fractions (non-bound material) were collected in fractions of 10 ml. After loading of the raw material the column was washed with 10 ml 10 mM M $K_2$ $HPO_4$ adjusted to pH 8.2

Following loading and washing the bound alpha-1-proteinase inhibitor (alpha-1-PI) was released and eluted with 10 mM potassium phosphate+1 M NaCl, pH 8.2.

Results

The table below shows the volumes of raw material and buffers loaded onto the column:

| Fraction | Volume |
| --- | --- |
| Protein fraction | 50 ml |
| Run through fractions | 5 × 10 ml |
| Wash fraction | 10 ml |
| Human alpha-1-PI eluate | 10 ml |

Quantification of human alpha-1-PI from the column

Single Radial Immunodiffusion (SRI) was performed in order to quantify the relative concentration of alpha-1-PI in the fractions from the column as described in Scand. J. Immunol. Vol. 17, Suppl. 10, 41-56, 1983.

The SRI was performed with Rabbit anti-human API from Dako Cytomation, Denmark, Cat. No.: A0012 (0.6 µl per cm$^2$).

A standard curve was performed with the protein fraction (100% reference) loaded onto the column in the concentration of 100%, 80%, 60%, 40% and 20%. The alpha-1-PI concentration in each of the fractions was determined against the standard curve and the relative yield in that fraction was calculated from the volume of the fraction relative to the volume and concentration of alpha-1-PI in the applied protein fraction.

Results

The table below shows the relative yield in percent of the total alpha-1-PI loaded onto the column:

| Determination of Human alpha-1-PI (alpha-1-proteinase inhibitor) | |
| --- | --- |
| Fraction | |
| Run through protein fraction 1 | 0% |
| Run through protein fraction 2 | 0% |
| Run through protein fraction 3 | 0% |
| Run through protein fraction 4 | 5% |
| Run through protein fraction 5 | 7% |
| Wash | <5%% |
| Eluate | 85% |

Purity of eluate and demonstration of elastase binding activity.

SDS-PAGE

For SDS-PAGE, Invitrogen SDS-Page 4-20% Tris-Glycine gel (cat no. EC6025) was used.

Demonstration of the elastase binding activity of the alpha-1-PI in the protein fraction (fraction 1, example 5) was performed by analysing the protein fraction with SDS-PAGE before and after incubation with elastase (Sigma code no E0127): The protein fraction was adjusted to pH 7 with 0.2 M NaOH and 500 µl of the protein fraction was added 6.5 µl elastase 2.5 mg/ml and incubated for 30 min. at 30° C.

Sample preparation: 25 µl sample and 25 µl sample buffer tris-glycine Invitrogen (cat no. LC2676) was mixed and boiled for 5 minutes in a water bath. The running buffer 0.024 M tris (Sigma T1378), 0.19 M glycine (Merck 5001901000), 0.1% SDS (sodium dodecyl sulphate, JT Baker 2811) pH 8.6 was added.

20 µl sample was applied in each analysis slot and the power was adjusted to give a current of 40 mA. When the blue line from the sample buffer reached one cm from the bottom of the gel the power was turned off and the gel was stained overnight in Invitrogen Colloidal Blue Staining Kit (cat. no. LC 6025) on a shaking table. The next day the gel was transferred into water and de-stained in water for 2 hours.

Results

Figure 1:
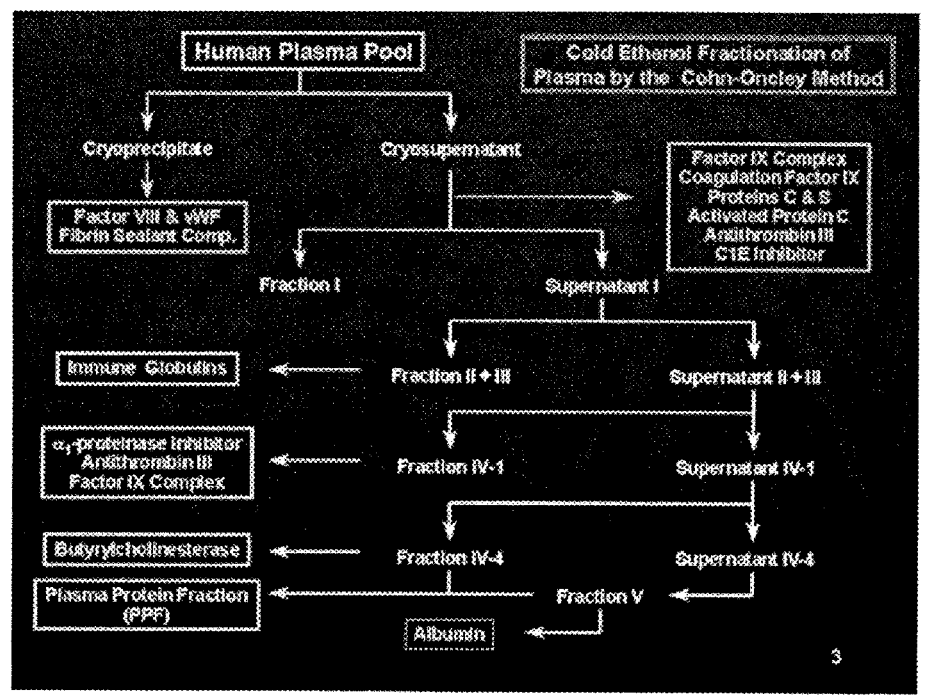
FIG. 1 illustrates the overall stepwise fractionation of human plasma proteins by gradual addition of ethanol to obtain a series of supernatants and precipitates comprising various human plasma proteins.
Figure 2:
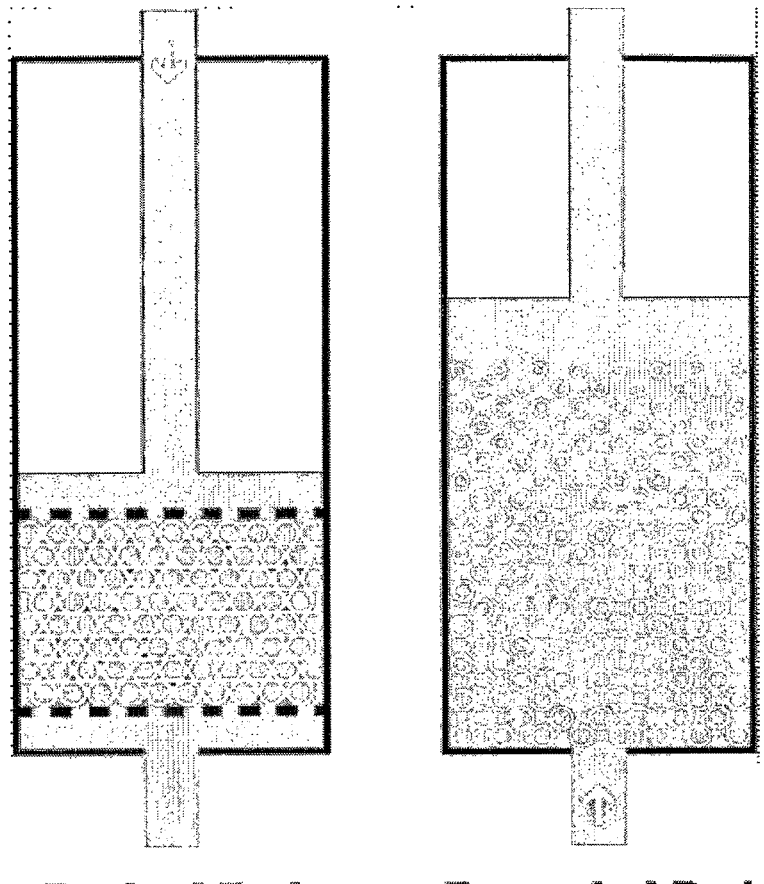
FIG. 2 illustrates the difference between a packed bed adsorption column comprising tightly packed adsorbent particles and an expanded bed adsorption column comprising adsorbent particles, which are fluidised by an upward flow of liquid. The expanded bed adsorption column still having plug flow with minimal back-mixing.
Figure 3:
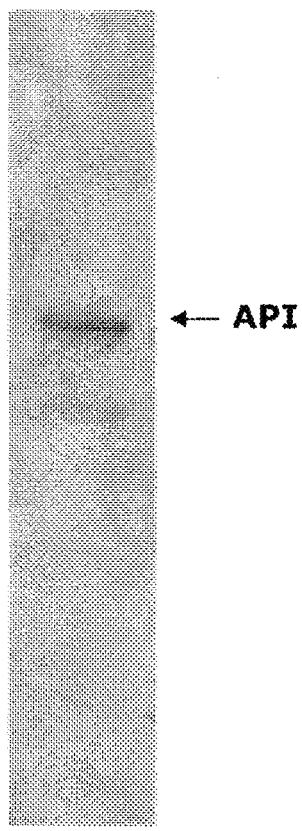
FIG. 3 illustrates a SDS-PAGE of eluate from DEAE ion exchanger performed in Example 7 and it shows that alpha-1-proteinase inhibitor-eluate from the DEAE ion exchanger has a high degree of purity as estimated by SDS-PAGE (estimated at >80%).

The result showed that the alpha-1-PI-eluate from the DEAE ion exchanger has a high degree of purity as estimated by SDS-PAGE (estimated at >80%). See also FIG. 3.

Furthermore, the result also showed that substantially all the alpha-1-proteinase inhibitor in the protein fraction (non-bound fraction from example 5) was active and capable of binding to elastase. See also FIG. 4

Example 8

Isolation of human API and human orosomucoid (alpha-1-acid glycoprotein) from non-bound fraction in example 5.

Adsorbent

Particle size (diameter) in the range of 80-150 µm. Adsorbents based on 6% agarose beads cross-linked and activated with epichlorohydrin prior to coupling of the following ligands:

| Experiment No | Ligand |
| --- | --- |
| 1 | 2-Hydroxy-pyridine (45 micromoles/ml adsorbent) |
| 2 | 4-Benzyl-oxyphenol (40 micromoles/ml adsorbent |
| 3 | 2-Amino-pyridine (40 micromoles/ml adsorbent) |
| 4 | 1,8-Diamino-octane (50 micromoles/ml adsorbent) |
| 5 | Benzylamine (35 micromoles/ml adsorbent) |
| 6 | 2,5-dimercapto-1,3,4-thiadiazole (65 micromoles/ml adsorbent) |
| 7 | N-Octylamine (70 micromoles/ml adsorbent) |

Protein Solution

Protein fraction 1 (the non-bound material) from isolation of human plasma proteins using expanded bed adsorption from example 5. The protein fraction was added ammonium sulphate to a final concentration of 2 M ammonium sulphate followed by careful adjustment to pH 8.2 with 1 M NaOH.

Process Parameters

The experiments were performed as packed bed adsorption in Poly-Prep columns product number 731-1550, Bio-Rad, USA. Flow rate was 1 ml/min in all steps.

Each of the columns was packed with 1 ml of adsorbent and the adsorbent was washed in the column with subsequently [1]) 5 ml demineralised water and [2]) 4 ml 2 M ammonium sulphate pH 8.2.

15 ml protein fraction was loaded onto each column and the run through fractions (non-bound material) were collected in two fractions. After loading of the protein fraction the columns were washed with subsequently [1]) 5 ml 2 M ammonium sulphate pH 8.2 [2]) 5 ml 1 M ammonium sulphate pH 8.2. After wash the adsorbent was eluted with 10 ml 10 mM potassium phosphate buffer pH 8.2+0.1 M NaCl (except for experiment 5, where pH of the buffer was pH 5.0). The washing and elution fractions were collected as individual fractions for analysis.

Results

The table below shows the volume of protein fraction loaded onto the columns as well as the volume of the fractions collected during experiment 1-7:

| Protein fraction Applied | Run trough Protein fraction 1 | Run trough Protein fraction 1 | Wash 1 | Wash 2 | Eluate |
|---|---|---|---|---|---|
| 15 ml | 5 ml | 10 ml | 5 ml | 5 ml | 10 ml |

Quantification of human alpha-1-PI and human Orosomucoid (alpha-1-acid glycoprotein) from experiment 1 to 7

Single Radial Immunodiffusion (SRI) was performed in order to quantify the relative concentration in percent of specific proteins in the fractions obtained as described in Scand. J. Immunol. Vol. 17, Suppl. 10, 41-56, 1983.

The SRI was performed with the following antibodies:
Rabbit anti-human alpha-1-PI, Dako Cytomation, Denmark, Cat. No. A0012 (0.6 μl per cm$^2$)
Rabbit anti-human Orosomucoid, Dako Cytomation, Denmark, Cat. No. A0011 (0.8 μl per cm$^2$)

A standard curve was performed with the protein fraction loaded onto the column (undiluted=100% reference) in the concentration of 100%, 80%, 60%, 40% and 20%. The relative concentration of the specific proteins in the fractions collected was determined against the standard curve. The relative yield of the specific proteins in each fraction was calculated from the volume of the fraction relative to the total amount of the protein applied to the column.

Determination of the purity of eluted alpha-1-PI (alpha-1-proteinase inhibitor)

SDS-PAGE

For SDS-PAGE, Invitrogen SDS-Page 4-20% Tris-Glycine gel (cat no. EC6025) was used.

Sample preparation: 25 μl sample and 25 μl sample buffer tris-glycine Invitrogen (cat no. LC2676) was mixed and boiled for 5 minutes in a water bath. The running buffer 0.024 M tris (Sigma T1378), 0.19 M glycine (Merck 5001901000), 0.1% SDS (sodium dodecyl sulphate, JT Baker 2811) pH 8.6 was added.

20 μl sample was applied in each analysis slot and the power was adjusted to give a current of 40 mA. When the blue line from the sample buffer reached one cm from the bottom of the gel the power was turned off and the gel was stained overnight in Invitrogen Colloidal Blue Staining Kit (cat. no. LC 6025) on a shaking table. The next day the gel was transferred into water and de-stained in water for 2 hours.

Results

The table below shows the relative yield of protein in each fraction in percent of the total amount applied to the column.

Determination of human alpha-1-PI and human Orosomucoid (alpha-1-acid glycoprotein). Yield relative to the total amount of applied protein

| Experiment no | Run through fraction 1 | Run through fraction 2 | Wash 1 | Wash 2 | Eluate |
|---|---|---|---|---|---|
| Ligand: 2-Hydroxy-pyridine | | | | | |
| 1  alpha-1-PI | — | — | — | 60% | 40% |
|    Orosomucoid | 20% | 80% | — | — | — |
| Ligand: 4-Benzyl-oxyphenol | | | | | |
| 2  alpha-1-PI | — | — | — | — | 30% |
|    Orosomucoid | — | — | — | — | 60% |
| Ligand: 2-Amino-pyridine | | | | | |
| 3  alpha-1-PI | 40% | 60% | — | — | — |
|    Orosomucoid | 40% | 60% | — | — | — |
| Ligand: 1,8 Diamino-octane | | | | | |
| 4  alpha-1-PI | — | 20% | — | 20% | — |
|    Orosomucoid | 40% | 60% | — | — | — |
| Ligand: Benzylamine | | | | | |
| 5  alpha-1-PI | — | — | — | — | 60% |
|    Orosomucoid | 20% | 25% | — | 60% | — |
| Ligand: 2,5-Dimercapto-1,3,4-thiadiazole | | | | | |
| 6  alpha-1-PI | — | — | — | — | 90% |
|    Orosomucoid | 15 | 40 | — | 40 | — |
| Ligand: N-Octylamine | | | | | |
| 7  alpha-1-PI | — | — | — | — | — |
|    Orosomucoid | — | — | — | — | — |

"—" = relative yield below 5%.

Further Down Stream Processing

Concentration of the eluate from experiment 5 (benzylamine as the ligand) by ultrafiltration followed by two viral inactivation steps: 1) solvent-detergent treatment and 2) viral filtration (nano-filtration) provide a product suitable for therapeutic use.

Example 9

Isolation of human API and human orosomucoid (alpha-1-acid glycoprotein).

Adsorbent

The particle size (diameter) was in the range of 80-150 μm. Adsorbents were based on 6% agarose beads cross-linked and activated with epichlorohydrin prior to coupling of the following ligands:

| Experiment No | Ligand |
|---|---|
| 1 | 2-Hydroxy-pyridine, (45 micromoles/ml adsorbent) |
| 2 | 4-Benzyl-oxyphenol, (40 micromoles/ml adsorbent) |
| 3 | 2,5-dimercapto-1,3,4-thiadiazole, (65 micromoles/ml adsorbent) |

Protein Solution

Protein fraction 1 (the non-bound material) from isolation of human plasma proteins using expanded bed adsorption from example 5. The protein fraction was added ammonium sulphate to a final concentration of 2 M ammonium sulphate followed by careful adjustment to pH 8.2 with 1 M NaOH.

Process Parameters

The experiments were performed as packed bed adsorption in Poly-Prep columns product number 731-1550, Bio-Rad, USA. Flow rate was 1 ml/min in all steps.

Each of the columns was packed with 1 ml of adsorbent and the adsorbent was washed in the column with subsequently [1)] 5 ml ion exchanged water and [2)] 4 ml 2 M ammonium sulphate pH 8.2.

75 ml protein fraction was loaded onto each column and the run through fractions were collected in five fractions of 15 ml each.

Experiment 1 and 2: After loading of the protein fraction the columns were washed with 5 ml 2 M ammonium sulphate pH 8.2 and eluted with 10 ml 10 mM potassium phosphate buffer pH 8.2, 0.1 M NaCl.

Experiment 3: After loading of the protein fraction the column was washed with subsequently with [1)] 5 ml 2 M ammonium sulphate pH 8.2 [2)] 5 ml 1 M ammonium sulphate pH 8.2. After wash the adsorbent was eluted with 10 ml 10 mM potassium phosphate buffer pH 8.2, 0.1 M NaCl.

Results

The table below shows the volumes of protein fraction and buffers loaded onto the columns in experiment 1-3

| Experiment | Protein fraction | Run trough Protein fraction 1-5 | Wash 1 | Wash 2 | Eluate |
|---|---|---|---|---|---|
| 1 | 75 ml | 15 ml | 5 ml | Not performed | 10 ml |
| 2 | 75 ml | 15 ml | 5 ml | Not performed | 10 ml |
| 3 | 75 nl | 15 ml | 5 ml | 5 ml | 10 ml |

Quantification of human alpha-1-PI and human Orosomucoid (alpha-1-acid glycoprotein) from experiment 1 to 7

Single Radial Immunodiffusion (SRI) was performed in order to quantify the concentration in percent of specific proteins in the fractions obtained from the columns relative to the protein fraction as described in Scand. J. Immunol. Vol. 17, Suppl. 10, 41-56, 1983.

The SRI was performed with the following monospecific antibodies:

Rabbit anti-human Alpha-1-PI, DakoCytomation, Denmark, Cat. No. A0012 (0.6 µl per cm$^2$)

Rabbit anti-human Orosomucoid, DakoCytomation, Denmark, Cat. No. A0011 (0.8 µl per cm$^2$)

A standard curve was performed with the protein fraction loaded onto the column (undiluted=100% reference) in the concentration of 100%, 80%, 60%, 40% and 20%. The relative concentration of the specific proteins in the fractions collected was determined against the standard curve. The relative yield of the specific proteins in each fraction was calculated from the volume of the fraction relative to the total amount of the protein applied to the column.

Results

The table below shows the relative yield of alpha-1-PI and orosomucoid (alpha-1-acid glycoprotein) in each fraction in percent of the total amount applied to the column.

| | Ligand: 2 Hydroxy pyridine | |
|---|---|---|
| Experiment - 1 | alpha-1-PI | Orosomucoid |
| Run through protein fraction 1 | 2% | 12% |
| Run through protein fraction 2 | 4% | 16% |
| Run through protein fraction 3 | 6% | 16% |
| Run through protein fraction 4 | 8% | 16% |
| Run through protein fraction 5 | 10% | 16% |
| Wash 1 | 0% | 16% |
| Wash 2 | N.P. | N.P. |
| Eluate | 80% | 0% |

| | Ligand: 4 benzyl oxy-phenol | |
|---|---|---|
| Experiment - 2 | alpha-1-PI | Orosomucoid |
| Run through protein fraction 1 | 0% | 0% |
| Run through protein fraction 2 | 0% | 0% |
| Run through protein fraction 3 | 1% | 4% |
| Run through protein fraction 4 | 2% | 6% |
| Run through protein fraction 5 | 4% | 8% |
| Wash 1 | 0% | 0% |
| Wash 2 | N.P. | N.P. |
| Eluate | 80% | 60% |

| | (Mimo CS) Ligand: 2,5-Dimercapto-1,3,4-thiadiazole | |
|---|---|---|
| Experiment - 3 | alpha-1-PI | Orosomucoid |
| Run through protein fraction 1 | 1% | 8% |
| Run through protein fraction 2 | 2% | 12% |
| Run through protein fraction 3 | 2% | 12% |
| Run through protein fraction 4 | 8% | 16% |
| Run through protein fraction 5 | 10% | 16% |
| Wash 1 | 0% | 0% |
| Wash 2 | 20% | 0% |
| Eluate | 50% | 0% |

"N.P." = Not performed

Example 10

Isolation of coagulation and anti-coagulation factors from raw human plasma by expanded bed adsorption.

Adsorbent

The adsorbent was based on agarose beads with tungsten carbide particles incorporated, the density of the conglomerate particles was 2.9 g/ml and the particle diameter was in the range of 40-120 µm with a mean volume particle diameter of 70 µm. The adsorbent was activated and cross-linked with epichlorohydrin and coupled with the ligand p-Xylylenediamine (final concentration of ligand was 25 micromoles per ml sedimented adsorbent).

Pre-Treatment of the Protein Solution

The raw human plasma (standard citrate plasma) was adjusted to pH 6.7 with 1 M acetic acid. The conductivity was hereafter 11.5 mS/cm$^2$ Process Parameters The experiment was performed in a FastLine® 10 expanded bed column (ϕ=1 cm) product number 7010-0000, UpFront Chromatography A/S.

The column was loaded with adsorbent to reach a settled bed height (H0) of 25 cm (corresponding to approx. 20 ml settled adsorbent) and washed and equilibrated at 20-25° C. with 20 mM sodium citrate buffer pH 6.7.

The experiment was performed with a linear flow rate of 300 cm/hr in all steps and the outlet from the column was connected to an UV monitor and recorder.

100 ml protein solution (corresponding to 5 times the settled bed volumes) was loaded onto the column.

Following loading of the protein solution non-bound material was washed out of the column with 5 mM sodium citrate pH 6.7 (labelled Wash 1). Following Wash 1 weakly bound proteins were washed out of the column with 5 mM sodium citrate+0.2 M sodium chloride pH 6.7 (labelled Wash 2). Subsequently the strongly bound proteins were eluted with 5 mM sodium citrate+0.8 M sodium chloride pH 6.7

The run-through and Wash 1 fraction was collected from the column as one fraction while, Wash 2 and the Eluate was collected in a separate fraction.

The raw plasma, the combined run-through and washing fraction and the eluate were then measured for the activity of a range of specific coagulation and anti-coagulation factors using the DiaMed CD-X analyzer (Cresser, Switzerland). Von Willebrand factor (vWF) biological activity was assessed by the ristocetin cofactor assay (vWFRco). Von Willebrand Factor antigen (vWFAg) was quantified using a turbidimetric assay. Protein S, Protein C and C1-inhibitor were measured with a functional assay.

Other proteins such as albumin, IgG, alpha-1-antitrypsin, fibrinogen, transferrin and alpha-1-acid-glycoprotein were determined by single radial immunodiffusion.

Setting the activity or amount of any specific protein applied to the column in the protein solution to 100%, the relative yield in each fraction can be determined. The total recovery is defined as the sum of the yields found in the run-through, washing and elution fractions.

The eluate was further analysed by size exclusion chromatography on a Superdex G200 (Amersham Biosciences). Fractions from the analysis were analysed for Factor VIII activity.

Results

Yield and total recovery of selected proteins relative to the starting material

|  | Raw plasma (%) | Run-through/ Wash 1 (%) | Wash 2 (%) | Eluate (%) | Recovery (%) |
| --- | --- | --- | --- | --- | --- |
| Factor II | 100 | <5 | <5 | 40 | 40-45 |
| Factor V | 100 | <5 | 70 | <5 | 70-75 |
| Factor VII | 100 | <5 | <5 | 100 | ~100 |
| Factor VIII | 100 | 10 | 10 | 45 | 65 |
| Factor IX | 100 | <5 | 10 | 50 | 60-65 |
| Factor X | 100 | <5 | <5 | 100 | ~100 |
| Factor XI | 100 | 40 | 10 | 20 | 70 |
| VWFAg | 100 | <5 | <5 | 60 | 60-65 |
| VWFRco | 100 | <5 | <5 | 55 | 55-60 |
| Protein S | 100 | <5 | <5 | 65 | 65-70 |
| Protein C | 100 | <5 | <5 | 65 | 65-70 |
| C1-inhibitor | 100 | 10 | 60 | 40 | ~100 |
| Fibrinogen | 100 | 95 | <5 | <5 | 95-100 |
| Albumin | 100 | 97 | 1 | <1 | 98 |
| IgG | 100 | 98 | 1 | <1 | 99 |
| Alpha-1-antitrypsin | 100 | 99 | <1 | <1 | 99 |
| Alpha-1-acid glycoprotein | 100 | 99 | <1 | <1 | 99 |

Size exclusion chromatography on a Superdex G200 indicated that Factor VIII in the eluate was complexed with Von Willebrand Factor (Factor VIII activity was appearing near the void volume of the size exclusion column, while no activity were found at the position corresponding to non-complexed Factor VIII).

Repeating the experiment at an increased flow rate of 500 cm/hour gave essentially the same results.

Example 11

Isolation of Factor VIII-vWF complex from plasma by expanded bed adsorption. Adsorbent binding capacity as a function of adsorbent particle size.

Adsorbents

The four adsorbents employed in this experiment were all based on agarose beads with tungsten carbide particles incorporated, the density of the conglomerate particles was 2.9 g/ml while the volume mean particle diameter was varied between 40 to 200 μm. The adsorbents were activated and cross-linked with epichlorohydrin and coupled with the ligand p-Xylylenediamine (final concentration of ligand was 25 micromoles per ml sedimented adsorbent). Four different adsorbent preparations were tested having the following volume mean particles diameters:

Volume mean particle diameter: 40 μm
Volume mean particle diameter: 70 μm
Volume mean particle diameter: 150 μm
Volume mean particle diameter: 200 μm Pre-Treatment of the Protein Solution The raw human plasma (standard citrate plasma) was adjusted to pH 6.7 with 1 M acetic acid. The conductivity was hereafter 11.5 mS/cm$^2$ Process Parameters The experiment was performed in a FastLine® 10 expanded bed column ($\phi$=1 cm) product number 7010-0000, UpFront Chromatography A/S.

The column was loaded with adsorbent to reach a settled bed height (H0) of 25 cm (corresponding to approx. 20 ml settled adsorbent) and washed and equilibrated at 20-25° C. with 20 mM sodium citrate buffer pH 6.7.

The experiment was performed with a linear flow rate of 350 cm/hr in all steps and the outlet from the column was connected to an UV monitor and recorder. 200 ml sample (corresponding to 10 times the settled bed volumes) was loaded onto the column.

Following loading of the protein solution, non-bound material was washed out of the column with 5 mM sodium citrate pH 6.7 (labelled Wash 1). Following Wash 1 weakly bound proteins were washed out of the column with 5 mM sodium citrate+0.2 M sodium chloride pH 6.7 (labelled Wash 2). Subsequently the strongly bound proteins were eluted with 5 mM sodium citrate+0.8 M sodium chloride pH 6.7

The run-through and Wash 1 fraction was collected from the column as one fraction while, Wash 2 and the Eluate was collected in a separate fraction.

The raw plasma, the combined run-through and washing fraction and the eluate were then measured for the activity of Factor VIII using the DiaMed CD-X analyzer (Cresser, Switzerland).

Setting the activity of Factor VIII applied to the column in the protein solution to 100%, the relative yield in each fraction was determined. The total recovery is defined as the sum of the yields found in the run-through, washing and elution fractions.

Results

Yield and total recovery of Factor VIII relative to the starting material.

|  | Raw plasma (%) | Run-through/ Wash 1 (%) | Wash 2 (%) | Eluate (%) | Recovery (%) |
| --- | --- | --- | --- | --- | --- |
| Ex. A, 40 μm | 100 | 10 | 10 | 50 | 70 |
| Ex. B, 70 μm | 100 | 20 | 15 | 35 | 70 |

-continued

| | Raw plasma (%) | Run-through/ Wash 1 (%) | Wash 2 (%) | Eluate (%) | Recovery (%) |
|---|---|---|---|---|---|
| Ex. C, 150 μm | 100 | 45 | 20 | 10 | 85 |
| Ex. D, 200 μm | 100 | 70 | 20 | 5 | 95 |

The adsorbent binding capacity for Factor VIII increases significantly with a decrease in volume mean particle diameter. The experiment illustrates the superior performance of adsorbents having a volume mean particle diameter below 150 μm.

Example 12

Isolation of human plasma proteins from human plasma using adsorbents coupled with different aromatic or heteroaromatic ligands comprising acidic groups
Adsorbents The adsorbents were all based on agarose with tungsten carbide particles incorporated, the density of the conglomerate particles was 2.9 g/ml and the particle diameter was in the range of 40-120 μm with a volume mean particle diameter of 70 μm. The adsorbents were cross-linked and activated with epichlorohydrin and coupled with the following different ligands: 2-mercaptonicotinic acid, 2-mercaptobenzoic acid, 3,4-diamino-benzoic acid, 2,4-dihydroxy-benzoic acid, 3,5-dihydroxy-benzoic acid, 2-(4-aminophenylthio)acetic acid, 2-mercapto-benzimidazole sulphonic acid, N-benzoyl-cysteine.

The ligand concentration on all the individual adsorbents was determined by acid-base titration to be in the range of 25-40 micromoles per ml sedimented adsorbent.

The following experiment was performed for each adsorbent:
Pre-Treatment of the Protein Solution The protein solution, human plasma, was diluted with demineralised water in a ratio of one volume of plasma to 2 volumes of water and pH was adjusted to pH 5.0 with 1 M hydrochloric acid. The conductivity was hereafter 5,25 mS/cm$^2$
Process Parameters:

The experiment was performed in a FastLine® 10 expanded bed column (φ=1 cm) product number 7010-0000, UpFront Chromatography A/S.

The column was loaded with adsorbent to reach a settled bed height (H0) of 50 cm (corresponding to approx 40 ml settled adsorbent) and washed and equilibrated at 20-25° C. with the following buffers in successive order $^{1)}$ 1 M NaOH, $^{2)}$ 40 mM citric acid buffer pH 4.5 $^{3)}$ 40 mM citric acid buffer pH 5.0.

The experiment was performed with a linear flow rate of 600 cm/hr in all steps and the outlet from the column was connected to an UV monitor and recorder.
Sample:

30 ml sample (corresponding to 10 ml undiluted plasma) was loaded onto the column.
Collection of Fractions:

Following loading of the protein solution, non-bound and weakly bound material was washed out of the column with 10 mM sodium citrate pH 5.0. The run-through and washing fraction, RT, (unbound fraction) was collected as one fraction according to the UV monitoring of the column effluent.

Subsequently the bound proteins were eluted in three sequential steps.
- Eluate 1—first elution step was performed with sodium caprylate 5 mg/ml, pH 6.0
- Eluate 2—second elution step was performed with 0.3 M sodium citrate pH 7.4.
- Eluate 3—third elution step was performed with 20 mM sodium citrate+0.1 M sodium chloride pH 7.4

In between first and second elution step the column was washed with 1 column volume of 1 M sodium citrate pH 7.4

Quantification of human plasma proteins in Run-through/washing fraction and elution 1, 2, and 3: Single Radial Immunodiffusion (SRI) was performed in order to demonstrate the components in each fraction from the column as described in Scand. J. Immunol. Vol. 17, Suppl. 10, 41-56, 1983.

The SRI was performed with the following antibodies, all from Dako Cytomation, Denmark:

| Antibody | Code no. | μl sample/well | μl per cm$^2$ |
|---|---|---|---|
| Rabbit anti human Albumin | A 0001 | 5 μl | 0.30 μl per cm$^2$ |
| Rabbit anti human IgG | A 0424 | 5 μl | 0.30 μl per cm$^2$ |
| Rabbit anti human Alpha-1-PI | A 0012 | 5 μl | 0.60 μl per cm$^2$ |
| Rabbit anti human Fibrinogen | A 0080 | 5 μl | 0.40 μl per cm$^2$ |
| Rabbit anti human Orosomucoid | A 0011 | 5 μl | 0.80 μl per cm$^2$ |
| Rabbit anti human Transferrin | A 0061 | 5 μl | 0.30 μl per cm$^2$ |

A standard curve was established with the protein solution (100% reference) loaded onto the column in the concentration of 100%, 80%, 60%, 40% and 20%. Each of the four fractions was determined relative to this standard curve and the relative yield of the specific protein in each fraction was determined. If the yield of a specific protein in a specific fraction relative to the amount of protein added to the column is above 5% the protein is defined to distribute into said fraction.
Results Distribution of selected proteins as a function of ligand structure

| Ligand | Alpha-1-proteinase inhibitor | Alpha-1-acid-glycoprotein | Albumin | IgG | Transferrin | Fibrinogen |
|---|---|---|---|---|---|---|
| 2-mercapto-nicotinic acid | RT | RT | E1 | E2 | E2 | E3 |
| 2-mercapto-benzoic acid | RT | RT | E1 | E2 | E2 | E3 |
| 3,4-Diamino-benzoic acid | RT | RT | RT | E1/E2 | E1/E2 | E2/E3 |
| 2,4-dihydroxy-benzoic acid | RT | RT | RT | E2 | RT | E2/E3 |

-continued

| Ligand | Alpha-1-proteinase inhibitor | Alpha-1-acid-glycoprotein | Albumin | IgG | Transferrin | Fibrinogen |
|---|---|---|---|---|---|---|
| 3,5-dihydroxy-benzoic acid | RT | RT | RT | E2 | RT | E2/E3 |
| 2-(4-amino-phenylthio)-acetic acid | RT | RT | RT/E1 | E2 | E2 | E2/E3 |
| 2-mercapto-benzimidazole sulphonic acid | RT | RT | RT/E1 | E2 | E2 | E2/E3 |
| N-benzoyl-cysteine | RT | RT | E1/E2 | E2 | E2 | E2/E3 |

RT = Run through and first wash,
E1 = Eluate 1,
E2 = Eluate 2,
E3 = Eluate 3
Threshold: At least 5% of the specific protein applied to the column must be present in the fraction The table illustrates that for the ligand 2-mercapto-nicotinic acid, alpha-1-proteinase inhibitor and alpha-1-acid glycoprotein are only present, to a degree of more than 5% of the total, in the combined run-through and washing fraction, while Albumin is only present in the first eluate, E1, i.e. there is no significant amount of albumin present in any of the other fractions, IgG and transferrin are only present in the second eluate and fibrinogen is only present in the third eluate. Thus generally it can be noted that there is very little cross-contamination of the individual proteins between the individual protein fractions obtained in the experiment. The experiment further illustrates that a broad range of aromatic or hetero-aromatic ligands comprising an acidic group may be used for the fractionation of human plasma or serum proteins according to the invention.

Example 13

Isolation of human alpha-1-proteinase inhibitor (alpha-1-PI) from non-bound fraction of example 5 at low ionic strength using adsorbent with a diamino-nonane ligand.

Adsorbent

The adsorbent was based on 4% agarose with tungsten carbide particles incorporated. The conglomerate beads had a density of approximately 3.8 g/ml and a particle size in the range of 40-100 μm with a volume mean particle size of 60 μm. The adsorbent was cross-linked and activated with epichlorohydrin and coupled with diamino-nonane. The ligand concentration was approx. 25 μmoles per ml sedimented adsorbent.

Protein Solution

The starting material for this experiment was Protein fraction 1 (the non-bound material) obtained from isolation of human plasma proteins using expanded bed adsorption as described in example 5. The pH in the protein fraction was carefully adjusted to pH 8.2 with 1 M sodium hydroxide and the conductivity was adjusted to 3.0 mS/cm$^2$ by the addition of demineralised water.

Process parameters

The experiment was performed as an expanded bed adsorption.

The experiment was performed in a FastLine® 10 expanded bed column (φ=1 cm) product number 7010-0000, UpFront Chromatography A/S.

The column was loaded with adsorbent to reach a settled bed height (H0) of 20 cm (corresponding to 16 ml adsorbent) and washed and equilibrated at 20-25° C. with the following buffers in successive order [1] 1 M NaOH, [2] 0.2 M HCl [3] 50% ethanol in water [4] 10 mM Tris/HCl pH 8.2

The experiment was performed with a linear flow rate of 900 cm/hr in all steps and the outlet from the column was connected to an UV monitor and recorder.

Sample 700 ml of the protein fraction adjusted to pH 8.2 and a conductivity of 3.0 mS/cm was loaded onto the column and the run-through fractions (non-bound material). After loading of the protein fraction, the column was washed with 10 mM Tris/HCl pH 8.2. The run-through and the washing fraction were collected as one combined fraction (using the UV-monitor to follow the wash out of un-bound material). Following loading and washing the bound alpha-1-PI was released and eluted with 15 mM potassium sodium citrate pH 6.0 and collected as Eluate 1. When all alpha-1-PI was eluted, as monitored on the UV-monitor, a second elution buffer, 15 mM sodium citrate+500 mM sodium chloride pH 5.2 was then applied to release alpha-1-acid-glycoprotein as Eluate 2. Eluate 2 was collected according to the peak obtained on the UV-recorder.

Quantification of human alpha-1-PI from the column

Single Radial Immunodiffusion (SRI) was performed in order to quantify the relative concentration of alpha-1-PI and alpha-1-acid glycoprotein (orosomucoid) in the fractions from the column as described in Scand. J. Immunol. Vol. 17, Suppl. 10, 41-56, 1983.

The SRI was performed with Rabbit anti-human API Cat. No.: A0012 (0.6 μl per cm$^2$) and Rabbit anti human Orosomucoid Cat. No. A 00110 (0.8 μl per cm$^2$) from DakoCytomation, Denmark, A standard curve was performed for each of the two proteins applied with the protein fraction as the 100% reference loaded onto the column in the concentration of 100%, 80%, 60%, 40% and 20%. The alpha-1-PI and alpha-1-acid glycoprotein concentration in each of the fractions was determined against the standard curve and the relative yield in that fraction was calculated from the volume of the fraction relative to the volume and concentration of alpha-1-PI in the applied protein fraction.

Purity of eluate and demonstration of elastase binding activity.

SDS-PAGE

For SDS-PAGE, Invitrogen SDS-Page 4-20% Tris-Glycine gel (cat no. EC6025) was used.

Elastase Binding

Demonstration of the elastase binding activity of the alpha-1-PI in the protein fraction was performed by analysing the raw material with SDS-PAGE before and after incubation with elastase (Sigma code no E0127): The protein fraction was adjusted to pH 7 with 0.2 M NaOH and 500 µl of the protein fraction was added 6.5 µl elastase 2.5 mg/ml and incubated for 30 min. at 30° C. Sample preparation: 25 µl sample and 25 µl sample buffer tris-glycine Invitrogen (cat no. LC2676) was mixed and boiled for 5 minutes in a water bath. The running buffer 0.024 M tris (Sigma T1378), 0.19 M glycine (Merck 5001901000), 0.1% SDS (sodium dodecyl sulphate, JT Baker 2811) pH 8.6 was added. 20 µl sample was applied in each analysis slot and the power was adjusted to give a current of 40 mA. When the blue line from the sample buffer reached one cm from the bottom of the gel the power was turned off and the gel was stained overnight in Invitrogen Colloidal Blue Staining Kit (cat. no. LC 6025) on a shaking table. The next day the gel was transferred into water and de-stained in water for 2 hours.

Results

The table below shows the relative yield of alpha-1-PI and alpha-1-acid glycoprotein in percent of the total amount of the individual proteins loaded onto the column:

| Fraction | Alpha-1-PI (%) | Alpha-1-acid-glycoprotein (%) |
|---|---|---|
| Run-through/Wash | 0 | 0 |
| Eluate 1 | 85 | <5 |
| Eluate 2 | 15 | 85 |

The results indicate that the adsorption procedure had separated apha-1-PI (alpha-1-proteinase inhibitor) and alpha-1-acid glycoprotein very efficiently.

SDS-PAGE analysis of alpha-1-PI in Eluate 1 revealed a purity of 80% and the elastase binding activity was found to be approximately 100%. Alpha-1-acid-glycoprotein was found to be approximately 45% pure as determined by SDS-PAGE.

These results further illustrate an effective isolation of alpha-1-proteinase inhibitor and alpha-1-acid glycoprotein using an adsorbent comprising an amino-alkyl ligand under low ionic strength binding conditions.

Example 14

Isolation of human plasma proteins from human plasma at different pH using an adsorbent coupled with 2-mercaptonicotinic acid.

Adsorbent

The adsorbent was based on agarose with tungsten carbide particles incorporated, the density of the conglomerate particles was 3.6 g/ml and the particle diameter was in the range of 40-100 µm with a volume mean particle diameter of 50 µm. The adsorbent was cross-linked and activated with epichlorohydrin and coupled with 2-mercaptonicotinic acid to obtain a ligand concentration of 32 micromoles per ml sedimented adsorbent.

Pre-Treatment of the Protein Solution

The protion solution, human plasma, was diluted with demineralised water in a ratio of one volume of plasma to 2 volumes of water. A series of experiments were performed wherein the starting material was adjusted to a range of different pH values (using 1 M hydrochloric acid for titration). The following experiments were performed:

A. pH of protein solution=3.0
B. pH of protein solution=4.0
C. pH of protein solution=4.5
D. pH of protein solution=5.0
E. pH of protein solution=5.5
F. pH of protein solution=6.0
G. pH of protein solution=6.5

Process parameters

The experiments were performed in a FastLine® 10 expanded bed column ($\phi$=1 cm) product number 7010-0000, UpFront Chromatography A/S.

For each experiment the column was loaded with adsorbent to reach a settled bed height (H0) of 50 cm (corresponding to approx 40 ml settled adsorbent) and washed and equilibrated at 20-25° C. with the following buffers in successive order [1] 1 M NaOH, [2] 40 mM citric acid buffer pH 4.5 [3] 40 mM citric acid buffer having the same pH as the protein solution for the specific experiment.

The experiment was performed with a linear flow rate of 400 cm/hr in all steps and the outlet from the column was connected to an UV monitor and recorder.

Sample 30 ml protein solution (corresponding to 10 ml undiluted plasma) was loaded onto the column.

Collection of Fractions:

Following loading of the protein solution, non-bound and weakly bound material was washed out of the column with 10 mM sodium citrate having the same pH as the sample for that particular experiment. The run-through and washing fraction, RT, (unbound fraction) was collected as one fraction according to the UV monitoring of the column effluent.

Subsequently the bound proteins were eluted in three sequential steps.

Eluate 1—first elution step was performed with sodium caprylate 5 mg/ml, pH 6.0

Eluate 2—second elution step was performed with 0.3 M sodium citrate pH 7.4.

Eluate 3—third elution step was performed with 20 mM sodium citrate+0.1 M sodium chloride pH 7.4

In between first and second elution step the column was washed with 1 column volume of 1 M sodium citrate pH 7.4

Quantification of human plasma proteins in Run-through/washing fraction and elution 1, 2, and 3: Single Radial Immunodiffusion (SRI) was performed in order to demonstrate the components in each fraction from the column as described in Scand. J. Immunol. Vol. 17, Suppl. 10, 41-56, 1983.

The SRI was performed with the following antibodies, all from Dako Cytomation, Denmark:

| Antibody | Code no. | µl sample/well | µl per cm² |
|---|---|---|---|
| Rabbit anti human Albumin | A 0001 | 5 µl | 0.30 µl per cm² |
| Rabbit anti human IgG | A 0424 | 5 µl | 0.30 µl per cm² |
| Rabbit anti human Alpha-1-PI | A 0012 | 5 µl | 0.60 µl per cm² |
| Rabbit anti human Fibrinogen | A 0080 | 5 µl | 0.40 µl per cm² |
| Rabbit anti human Orosomucoid | A 0011 | 5 µl | 0.80 µl per cm² |
| Rabbit anti human Transferrin | A 0061 | 5 µl | 0.30 µl per cm² |

A standard curve was established with the protein solution (100% reference) loaded onto the column in the concentration of 100%, 80%, 60%, 40% and 20%. Each of the four fractions was determined relative to this standard curve and the relative yield of the specific protein in each protein fraction was determined. If the yield of a specific protein in a specific protein fraction relative to the amount of protein added to the column is above 5% the protein is defined to distribute into said fraction.
Results
Distribution of selected proteins as a function of sample and washing pH

| pH of sample and washing buffer | Alpha-1-proteinase inhibitor | Alpha-1-acid-glycoprotein | Albumin | IgG | Transferrin | Fibrinogen |
|---|---|---|---|---|---|---|
| A. pH = 3.0 | RT/E2 | ND | RT/E1/E2 | RT/E2 | RT/E2 | RT |
| B. pH = 4.0 | RT/E2 | ND | E1/E2 | RT/E1/E2/E3 | E2 | RT/E2/E3 |
| C. pH = 4.5 | RT/E2 | RT | E1/E2 | E2 | E2 | E2/E3 |
| D. pH = 5.0 | RT | RT | E1 | E2 | E2 | E3 |
| E. pH = 5.5 | RT | RT | RT/E1 | E2 | E2 | E3 |
| F. pH = 6.0 | RT | RT | RT | RT/E2 | RT/E2 | E3 |
| G pH = 6.5 | RT | RT | RT | RT/E2 | RT/E2 | RT/E3 |

RT = Run through and first wash,
E1 = Eluate 1,
E2 = Eluate 2,
E3 = Eluate 3,
ND = not determined.
Threshold: At least 5% of the specific protein applied to the column must be present in the fraction The table illustrates that for the ligand 2-mercaptonicotinic acid, a pH-value of the protein solution and washing buffer in the range of pH 5.0 to pH 5.5 results in the most effective separation of the proteins analysed. More proteins appear in the non-bound fraction, RT, whenever the pH is below pH 4.5 or above pH 5.5. Below pH 5.0, alpha-1-antitrypsin (alpha-1-proteinase inhibitor) is found to denature (polymerise), which is supported by the finding that it appears in both RT and E2 at and below pH 4.5.

Example 15

Isolation of human plasma proteins from human plasma with different buffers and different ionic strength/conductivity using an adsorbent coupled with 2-mercaptonicotinic acid.
Adsorbent
The adsorbent was based on agarose with tungsten carbide particles incorporated, the density of the conglomerate particles was 3.6 g/ml and the particle diameter was in the range of 40-100 µm with a volume mean particle diameter of 50 µm. The adsorbent was cross-linked and activated with epichlorohydrin and coupled with 2-mercaptonicotinic acid to obtain a ligand concentration of 32 micromoles per ml sedimented adsorbent.
Pre-Treatment of the Protein Solution
The protein solution, human plasma, was diluted with demineralised water in a ratio of one volume of plasma to 2 volumes of water. A series of experiments were performed wherein the protein solution was added a range of different buffer substances resulting in a range of different ionic strengths/conductivities. All experiments were performed at a sample pH of 5.0
The following experiments were performed:
A. 10 mM sodium citrate, conductivity=6,0 mS/cm
B. 20 mM sodium citrate, conductivity=8,5 mS/cm
C. 20 mM sodium acetate, conductivity=6,2 mS/cm
D. 20 mM histidine, conductivity=6,6 mS/cm
E. 20 mM glycine, conductivity=5,5 mS/cm
F. 20 mM octylamine, conductivity=8,0 mS/cm Process parameters:
The experiments were performed in a FastLine® 10 expanded bed column ($\phi$=1 cm) product number 7010-0000, UpFront Chromatography A/S.
For each experiment the column was loaded with adsorbent to reach a settled bed height (H0) of 50 cm (corresponding to approx 40 ml settled adsorbent) and washed and equilibrated at 20-25° C. with the following buffers in successive order [1] 1 M NaOH, [2] 40 mM citric acid buffer pH 4.5 [3] 40 mM citric acid buffer pH 5.0.
The experiment was performed with a linear flow rate of 400 cm/hr in all steps and the outlet from the column was connected to an UV monitor and recorder.
Sample
30 ml protein solution (corresponding to 10 ml undiluted plasma) was loaded onto the column.
Collection of Protein Fractions:
Following loading of the protein solution, non-bound and weakly bound material was washed out of the column with the same buffer type and same buffer concentration as added to the sample for the particular experiment. All washing buffers were at pH 5.0. The run-through and washing fraction, RT, (unbound fraction) was collected as one fraction according to the UV monitoring of the column effluent.
Subsequently the bound proteins were eluted in three sequential steps.
Eluate 1—first elution step was performed with sodium caprylate 5 mg/ml, pH 6.0
Eluate 2—second elution step was performed with 0.3 M sodium citrate pH 7.4.
Eluate 3—third elution step was performed with 20 mM sodium citrate+0.1 M sodium chloride pH 7.4
In between first and second elution step the column was washed with 1 column volume of 1 M sodium citrate pH 7.4
Quantification of human plasma proteins in Run-through/washing fraction and elution 1, 2, and 3: Single Radial Immunodiffusion (SRI) was performed in order to demonstrate the components in each fraction from the column as described in Scand. J. Immunol. Vol. 17, Suppl. 10, 41-56, 1983.
The SRI was performed with the following antibodies, all from Dako Cytomation, Denmark:

| Antibody | Code no. | µl sample/well | µl per cm² |
|---|---|---|---|
| Rabbit anti human Albumin | A 0001 | 5 µl | 0.30 µl per cm² |
| Rabbit anti human IgG | A 0424 | 5 µl | 0.30 µl per cm² |

-continued

| Antibody | Code no. | μl sample/well | μl per cm² |
|---|---|---|---|
| Rabbit anti human Alpha-1-PI | A 0012 | 5 μl | 0.60 μl per cm² |
| Rabbit anti human Fibrinogen | A 0080 | 5 μl | 0.40 μl per cm² |
| Rabbit anti human Orosomucoid | A 0011 | 5 μl | 0.80 μl per cm² |
| Rabbit anti human Transferrin | A 0061 | 5 μl | 0.30 μl per cm² |

A standard curve was established with the protein solution (100% reference) loaded onto the column in the concentration of 100%, 80%, 60%, 40% and 20%. Each of the four protein fractions was determined relative to this standard curve and the relative yield of the specific protein in each protein fraction was determined. If the yield of a specific protein in a specific protein fraction relative to the amount of protein added to the column is above 5% the protein is defined to distribute into said protein fraction.

Results

Distribution of selected proteins as a function of sample and washing buffer composition/conductivity.

| Buffer added to sample and washing buffer | Alpha-1-proteinase inhibitor | Alpha-1-acid-glycoprotein | Albumin | IgG | Transferrin | Fibrinogen |
|---|---|---|---|---|---|---|
| A. 10 mM sodium citrate; | RT | RT | E1 | E2 | E2 | E3 |
| B. 20 mM sodium citrate | RT | RT | RT/E1 | E2 | E2 | E3 |
| C. 20 mM sodium acetate | RT | RT | E1 | E2 | E2 | E3 |
| D. 20 mM histidine | RT | RT | E1 | E2 | E2 | E3 |
| E. 20 mM glycine | RT | RT | E1 | E2 | E2 | E3 |
| F. 20 mM octylamine | RT | RT | RT | RT | RT | RT/E3 |

RT = Run through and first wash,
E1 = Eluate 1,
E2 = Eluate 2,
E3 = Eluate 3.
Threshold: At least 5% of the specific protein applied to the column must be present in the fraction.

Example 16

Isolation of human and animal plasma proteins from different un-diluted human and animal plasma using an adsorbent coupled with 2-mercaptonicotinic acid.

Adsorbent

The adsorbent was based on agarose with tungsten carbide particles incorporated, the density of the conglomerate particles was 2.0 g/ml and the particle diameter was in the range of 50-150 μm with a volume mean particle diameter of 120 μm. The adsorbent was cross-linked and activated with epichlorohydrin and coupled with 2-mercaptonicotinic acid to obtain a ligand concentration of 36 micromoles per ml sedimented adsorbent.

Pre-Treatment of the Protein Solution

The protein solution, plasma from human and a range of different animal plasma, was adjusted to pH 5.0 with 1 M hydrochloric acid. A series of experiments were performed using different plasma:

The following experiments were performed:
A. Un-diluted human plasma
B. Un-diluted horse plasma
C. Un-diluted bovine plasma
D. Un-diluted rabbit plasma
E. Un-diluted goat plasma
F. Un-diluted Chicken plasma
G. Un-diluted pig plasma
H. Un-diluted mouse plasma Process Parameters The experiments were performed in a FastLine® 10 expanded bed column (φ=1 cm) product number 7010-0000, UpFront Chromatography A/S.

For each experiment the column was loaded with adsorbent to reach a settled bed height (H0) of 50 cm (corresponding to approx 40 ml settled adsorbent) and washed and equilibrated at 20-25° C. with the following buffers in successive order [1] 1 M NaOH, [2] 40 mM citric acid buffer pH 4.5 [3] 40 mM citric acid buffer pH 5.0.

The experiment was performed with a linear flow rate of 900 cm/hr in all steps and the outlet from the column was connected to an UV monitor and recorder.

Sample 20 ml protein solution was loaded onto the column (corresponding to 0.5 ml plasma per ml settled adsorbent).

Collection of Protein Fractions:

Following loading of the protein solution, non-bound and weakly bound material was washed out of the column 10 mM sodim citrate pH 5.0. The run-through and washing fraction, RT, (unbound protein fraction) was collected as one protein fraction according to the UV monitoring of the column effluent.

Subsequently the bound proteins were eluted in three sequential steps.
  Eluate 1—first elution step was performed with sodium caprylate 5 mg/ml, pH 6.0
  Eluate 2—second elution step was performed with 20 mM sodium citrate+0.1 M sodium chloride pH 7.4

All protein fractions were analysed by NON-REDUCED SDS-PAGE using Invitrogen SDS-Page 4-20% Tris-Glycine gel (cat no. EC6025). The coomassie stained bands on the SDS PAGE was qualitatively and semi-quantitatively examined by visual inspection to register the distribution of selected plasma proteins in the individual column fractions. If a protein band, present in a specific protein fraction, is estimated to represent more than 10% of the total protein added to the column the protein is defined as distributing to that particular protein fraction (the threshold value).

Results

Distribution of selected proteins as a function of sample origin.

| Sample | Albumin | IgG |
|---|---|---|
| A. Human Plasma | RT/E1 | E2 |
| B. Horse Plasma | RT/E1 | E2 |
| C. Cow Plasma | RT/E1 | E2 |
| D. Rabbit Plasma | RT/E1 | E2 |
| E. Goat Plasma | RT/E1 | E2 |
| F. Chicken Plasma | RT/E1 | E2 |
| G. Pig Plasma | RT/E1 | E2 |
| H. Mouse Plasma | RT/E1 | E2 |

RT = Run through and first wash,
E1 = Eluate 1,
E2 = Eluate 2.
Threshold: At least 10% of the specific protein applied to the column must be present in the fraction.

The results illustrate that different un-diluted animal and human plasma behave very similarly when fractionated with a 2-mercapto-nicotinic acid coupled adsorbent under the specified process conditions. The adsorbent bind and elute practically all IgG from all the species tested. The adsorbent bind most of the albumin present in all plasma samples tested and in all experiments the bound albumin is efficiently eluted by the 5 mg/ml sodium caprylate pH 6.0 buffer.

Example 17

Isolation of human plasma proteins from human plasma using adsorbents of different size coupled with 2-mercaptonicotinic acid.

Adsorbent

The adsorbents employed were all based on agarose with tungsten carbide particles incorporated, the density of the conglomerate particles was 2.5 g/ml and the particle diameter and the volume mean particle diameter varied as follows:

| | |
|---|---|
| Adsorbent A. | Particle diameter range: 60-140 µm |
| | Volume mean particle diameter: 90 µm |
| Adsorbent B. | Particle diameter range: 60-150 µm |
| | Volume mean particle diameter: 120 µm |
| Adsorbent C. | Particle diameter range: 80-240 µm |
| | Volume mean particle diameter: 150 µm |
| Adsorbent D. | Particle diameter range: 80-300 µm |
| | Volume mean particle diameter: 200 µm |
| Adsorbent E. | Particle diameter range: 100-400 µm |
| | Volume mean particle diameter: 250 µm |

The adsorbent A-E were produced by sieving on defined pore-size nylon nets from one batch of particles having a broad size distribution, which was first cross-linked and activated with epichlorohydrin and coupled with 2-mercaptonicotinic acid to obtain a ligand concentration of 28 micromoles per ml sedimented adsorbent. Thus, all adsorbent A-E were designed to deviate from each other only with respect to the size of the particles.

For each adsorbent A-E the following experiment was performed:

Pre-Treatment of the Protein Solution

The protein solution, human plasma, was diluted with demineralised water in a ratio of one volume of plasma to 2 volumes of water and pH was adjusted to pH 5.0 with 1 M hydrochloric acid. The conductivity was hereafter 5,2 mS/cm$^2$ Process parameters The experiment was performed in a FastLine® 10 expanded bed column ($\phi$=1 cm) product number 7010-0000, UpFront Chromatography A/S.

The column was loaded with adsorbent to reach a settled bed height (H0) of 50 cm (corresponding to approx 40 ml settled adsorbent) and washed and equilibrated at 20-25° C. with the following buffers in successive order [1] 1 M NaOH, [2] 40 mM citric acid buffer pH 4.5 [3] 40 mM citric acid buffer pH 5.0.

The experiment was performed with a linear flow rate of 900 cm/hr in all steps and the outlet from the column was connected to an UV monitor and recorder.

Sample 30 ml sample (corresponding to 10 ml undiluted plasma) was loaded onto the column.

Collection of Protein Fractions:

Following loading of the protein sample, non-bound and weakly bound material was washed out of the column with 10 mM sodium citrate pH 5.0. The run-through and washing fraction, RT, (unbound fraction) was collected as one protein fraction according to the UV monitoring of the column effluent.

Subsequently the bound proteins were eluted in three sequential steps.

Eluate 1—first elution step was performed with sodium caprylate 5 mg/ml, pH 6.0
Eluate 2—second elution step was performed with 20 mM sodium citrate+0.1 M sodium chloride pH 7.4

Quantification of human plasma proteins in Run-through/washing fraction and elution 1 and 2, Single Radial Immunodiffusion (SRI) was performed in order to demonstrate the components in each protein fraction from the column as described in Scand. J. Immunol. Vol. 17, Suppl. 10, 41-56, 1983.

The SRI was performed with the following antibodies, all from Dako Cytomation, Denmark:

| Antibody | Code no. | µl sample/well | µl per cm$^2$ |
|---|---|---|---|
| Rabbit anti human Albumin | A 0001 | 5 µl | 0.30 µl per cm$^2$ |
| Rabbit anti human IgG | A 0424 | 5 µl | 0.30 µl per cm$^2$ |

A standard curve was established with the protein solution (100% reference) loaded onto the column in the concentration of 100%, 80%, 60%, 40% and 20%. Each of the three protein fractions was determined relative to this standard curve and the relative yield of the specific protein in each protein fraction was determined.

Results:

Distribution of selected proteins as a function adsorbent particle size

| Adsorbent particle size range and volume mean particle size | Albumin (%) | IgG (%) |
|---|---|---|
| Adsorbent A. | RT: <5 | RT: <5 |
| Particle diameter range: 60-140 µm | E1: 90 | E1: <5 |
| Volume mean particle diameter: 90 µm | E2: <5 | E2: <5 |
| Adsorbent B. | RT: <5 | RT: <5 |
| Particle diameter range: 60-150 µm | E1: 90 | E1: <5 |
| Volume mean particle diameter: 120 µm | E2: <5 | E2: 90 |
| Adsorbent C. | RT: 10 | RT: 20 |
| Particle diameter range: 80-240 µm | E1: 88 | E1: <5 |
| Volume mean particle diameter: 150 µm | E2: <5 | E2: 70 |
| Adsorbent D. | RT: 25 | RT: 30 |
| Particle diameter range: 80-300 µm | E1: 70 | E1: <5 |
| Volume mean particle diameter: 200 µm | E2: <5 | E2: 50 |

-continued

| Adsorbent particle size range and volume mean particle size | Albumin (%) | IgG (%) |
|---|---|---|
| Adsorbent E. Particle diameter range: 100-400 μm Volume mean particle diameter: 250 μm | RT: 30 E1: 65 E2: <5 | RT: 30 E1: <5 E2: 50 |

RT = Run through and first wash,
E1 = Eluate 1,
E2 = Eluate 2

The results illustrate that at a high flow rate (900 cm/hour) it is only adsorbents having a volume mean particle size below 150 μm that achieve to bind practically all the albumin and IgG present in the applied sample. The higher the particle size the lower the protein yield in the respective eluate protein fractions.

Example 18

Large scale isolation of human plasma proteins from human plasma in a 30 cm diameter EBA column.

Adsorbent

The adsorbent was based on agarose with tungsten carbide particles incorporated, the density of the conglomerate particles was 2.8 g/ml and the particle diameter is in the range of 40-120 μm with a mean particle diameter of 72 μm. The adsorbent comprised 2-mercaptonicotinic acid as the ligand and had a ligand concentration of 38 micromoles per ml sedimented adsorbent.

Pre-Treatment of the Protein Solution

The protein solution, human citrate plasma, was diluted with demineralised water in a ratio of one volume of plasma to 2 volumes of water and pH was adjusted to pH 5.0 with 1 M hydrochloric acid. The conductivity was hereafter 5,3 mS/cm$^2$ Process parameters The experiment was performed in a FastLine® 300 expanded bed column (φ=30 cm), product number 7300-0000, UpFront Chromatography A/S.

The column was loaded with adsorbent to reach a settled bed height (H0) of 50 cm (corresponding to 35.3 L adsorbent) and washed and equilibrated at 20-25° C. with the following buffers in successive order $^{1)}$ 36 L 1 M NaOH, $^{2)}$ 90 L 40 mM citric acid buffer pH 4.5 $^{3)}$ 90 L 40 mM citric acid buffer pH 5.0.

The experiment was performed with a linear flow rate of 450 cm/hr (corresponding to a volumetric flow of 5,3 L/min) in all steps and the outlet from the column was connected to an UV monitor and recorder.

Sample

39 L protein solution (corresponding to 13 L undiluted plasma) was loaded onto the column.

Collection of Protein Fractions:

Following loading of the protein solution, non-bound and weakly bound material was washed out of the column with 10 mM sodium citrate pH 5.0. Fraction 1 (unbound fraction) was collected as one protein fraction according to the UV monitoring of the column effluent.

Subsequently the bound proteins were eluted in three sequential steps.

Protein fraction 2—first elution step was performed with sodium caprylate 5 mg/ml, pH 6.0

Protein fraction 3—second elution step was performed with 0.3 M sodium citrate pH 7.4.

Protein fraction 4—third elution step was performed with 20 mM sodium citrate+0.1 M NaCl pH 7.4

In between first and second elution step the column was briefly washed with 40 L of 1 M sodium citrate pH 7.4

Results

The table below shows the volumes of each fraction:

| Fraction | Run |
|---|---|
| Equilibration buffer $^{(1}$ | 36 L |
| Equilibration buffer $^{(2}$ | 90 L |
| Equilibration buffer $^{(3}$ | 90 L |
| Protein fraction 1 | |
| Non bound proteins and wash | 293 L |
| Protein fraction 2 | 136 L |
| Protein fraction 3 | 135 L |
| Protein fraction 4 | 83 L |

Quantification of human plasma proteins fraction 1, 2, 3 and 4 from the column Single Radial Immunodiffusion (SRI) was performed in order to demonstrate the components in each protein fraction from the column as described in Scand. J. Immunol. Vol. 17, Suppl. 10, 41-56, 1983.

The SRI was performed with the following antibodies, all from Dako Cytomation, Denmark:

| Antibody | Code no. | μl sample/well | μl per cm$^2$ |
|---|---|---|---|
| Rabbit anti human Albumin | A 0001 | 5 μl | 0.30 μl per cm$^2$ |
| Rabbit anti human IgG | A 0424 | 5 μl | 0.30 μl per cm$^2$ |
| Rabbit anti human Alpha-1-PI | A 0012 | 5 μl | 0.60 μl per cm$^2$ |
| Rabbit anti human Fibrinogen | A 0080 | 5 μl | 0.40 μl per cm$^2$ |
| Rabbit anti human Haptoglobin | A 0030 | 15 μl | 0.45 μl per cm$^2$ |
| Rabbit anti human GC-Globulin | A 0021 | 15 μl | 0.60 μl per cm$^2$ |
| Rabbit anti human IgM | A 0426 | 15 μl | 0.40 μl per cm$^2$ |
| Rabbit anti human IgA | A 0092 | 15 μl | 0.50 μl per cm$^2$ |
| Rabbit anti human Alpha-2 Macroglobulin | A 0033 | 15 μl | 0.40 μl per cm$^2$ |
| Rabbit anti human Orosomucoid | A 0011 | 5 μl | 0.80 μl per cm$^2$ |
| Rabbit anti human Transferrin | A 0061 | 5 μl | 0.30 μl per cm$^2$ |
| Rabbit anti human Prealbumin | A 0002 | 15 μl | 0.75 μl per cm$^2$ |
| Rabbit anti human Antitrombin III | A 0296 | 25 μl | 0.50 μl per cm$^2$ |

A standard curve was established with the protein solution (100% reference) loaded onto the column in the concentration of 100%, 80%, 60%, 40% and 20%. Each of the four protein fractions was determined relative to this standard curve for each protein tested and the relative yield of the specific protein in each protein fraction was determined.

Results

Yield of each human protein relative to the applied raw material in each of the 4 fractions from the EBA column:

|  | Fraction 1 Non bound material | Fraction 2 | Fraction 3 | Fraction 4 |
|---|---|---|---|---|
| human Albumin | — | 98% | — | — |
| human IgG | — | — | 95% | 5% |
| human Alpha-1-PI | 95% | — | — | — |
| human Fibrinogen | — | — | 10% | 60-80% |
| human Haptoglobin | 40% | 40% | 20% | — |
| human GC-Globulin | — | 100% | — | — |
| human IgM | — | — | 75% | — |
| human IgA | 15% | 20% | 70% | — |
| human Alpha-2 Macroglobulin | — | 45% | 35% | — |
| human Orosomucoid | 100% | — | — | — |
| human Transferrin | — | — | 95% | — |
| human Prealbumin | 55% | — | — | — |
| human Antitrombin III | — | 75% | — | — |

"—" relative yield below 5%

The process according to the invention was working efficiently in large scale and resulted in a separation of the plasma proteins very similar to experiments performed in 1 cm diameter columns.

Example 19

Isolation of human plasma proteins from Cryopoor plasma by using expanded bed adsorption with a flow rate at 450 cm/hr and conditions as under Example 5.

Cryopoor plasma, also called cryosupernatant, produced by slow thawing of frozen human citrate plasma and separating from the cryo-precipitate was used instead of full human citrate plasma in a repetition of example 5. All other parameters were kept constant.
Results The experiment gave a result similar to the results obtained with full human plasma as described in example 5 except for the substantially complete absence of fibrinogen in protein fraction 4 (eluate 3).

Example 20

Isolation of Fibrinogen from resolubilised Cryoprecipitate. Batch adsorption using high density adsorbent having low volume mean diameter.
Adsorbent The adsorbent was based on agarose with tungsten carbide particles incorporated, the density of the conglomerate particles was 3.8 g/ml and the particle diameter was in the range of 20-60 µm with a mean particle diameter of 38 µm. The adsorbent comprised 2-mercaptonicotinic acid as the ligand and a ligand concentration of 31 micromoles per ml sedimented adsorbent.
Pre-Treatment of Protein Solution Cryoprecipitate produced by slow thawing of 2000 ml frozen human citrate plasma and separated from the cryo-supernatant was re-solubilised by mixing with 10 mM sodium citrate pH 6.7 resulting in approx. 120 ml turbid solution.
Batch Adsorption Followed by Column Elution The re-solubilised cryo-precipitate was transferred to a 200 ml glass-beaker and 20 ml adsorbent beads thoroughly washed with 10 mM sodium citrate pH 6.7 were added. Mixing of adsorbent and protein solution was performed with a gentle mechanical stirrer for 30 minutes at ambient temperature. Following adsorption the adsorbent was allowed to settle and the supernatant was decanted. Washing buffer (20 mM sodium citrate pH 6.7) was then added as 3 times 100 ml aliquots with mixing, sedimentation and decantation in between each addition. Mixing was performed for 2 minutes for each addition. Following washing, the adsorbent was suspended in a small amount of washing buffer and poured into a 2 cm diameter packed bed column, wherein it settled very quickly. Elution of bound protein was then performed by adding 20 mM potassium phosphate+0.8 M sodium chloride pH 6.7 at a flow rate of 2 ml per minute. The column elution was monitored with an UV-monitor and the elution peak was collected in one fraction.

The eluate protein fraction was analysed for purity using SDS-PAGE (non-reduced Invitrogen SDS-APGE 4-20% Tris-glycine gel, cat. no.: EC6025). Fibrinogen functional activity was determined by the von Clauss method (clotting time with bovine thrombin).
Results Upon stopping the mixing of the adsorbent and the re-solubilised cryoprecipitate after the 30 minutes adsorption period the adsorbent particles sedimented on the bottom of the container within less than 30 seconds. Decantation of supernatants from the settled adsorbent was extremely facile since the adsorbent beads stayed on the bottom of the glass-beaker without any significant tendency to mix with the liquid phase. Addition and washing with 3× washing buffer was equally performed within few minutes due to the fast separation of the adsorbent. The adsorbent was equally packed in the elution column in less than one minute (these procedures normally take up to several hours with low density beads of such a small diameter). The fibrinogen eluted from the column as a highly concentrated clear solution of fibrinogen (elution volume=21 ml).

SDS-PAGE analysis of the eluted fibrinogen revealed that the protein was more than 85% pure with IgG being the major contaminant. No albumin could be detected in the eluate. The biological activity of the eluted fibrinogen was found to be fully intact.

The experiment illustrates the significant advantage of using a high density adsorbent having low volume mean diameter for separation of plasma proteins from re-solubilised cryo-precipitate.

Example 21

Cascade isolation of coagulation/anti-coagulation factors, Albumin, IgG, Fibrinogen, alpha-1-proteinase inhibitor and alpha-1-acid-glycoprotein using three consecutive columns and virus eliminated human plasma as the protein solution.
Adsorbents The adsorbents used in example 10 (Ligand=1,4-Di-amino-xylylene), example 5 (2-mercapto-nicotinic acid) and example 13 (1,9-diamino-nonane) was utilised in this experiment.

Virus elimination

A human plasma protein solution was treated with a solvent-detergent solution (known as S/D treatment) by the addition of Tri-n-butyl phosphate (0.3% final concentration) and TWEEN® 80 polysorbates (1% final concentration) at 25 degrees Celsius followed by incubation at the same temperature for 6 hours.

Successive Adsorption

The S/D treated plasma was then fractionated in three successive adsorption steps:

Column A: As described in example 10
Column B: As described in example 5
Column C: As described in example 13

Column A was performed as described in example 10. The combined run-through and washing fraction was adjusted to pH 5.0 with 1 M hydrochloric acid and was then diluted with water to obtain a final dilution relative to the volume of starting material corresponding to 1+2 (as described in example 5) and then 120 ml of the diluted protein solution was applied to column B as described in example 5. The combined run-through and washing fraction from column B was collected, pre-treated and processed as described in example 13. For all three columns all elution protein fractions were collected and analysed as described in the respective examples.

Results

The analysis of all column eluates gave essentially the same results as described in the individual examples. Thus, the viral elimination step by S/D treatment did not interfere with the fractionation of the proteins when using the selected adsorbents. At the same time no TWEEN® 80 polysorbates or Tri-n-butyl phosphate could be detected in any of the isolated protein fractions surprisingly illustrating that none of the adsorbents chosen bind these substances. The isolated protein fractions are therefore efficiently depleted for the viral elimination substances simultaneously with the actual separation of the proteins and no extra steps are therefore required to eliminate these from the isolated proteins.

The experiment further illustrates the successful consecutive separation of human plasma proteins into the following in total 6 different protein fractions having very little cross-contamination and very high yield: A. Coagulation and anti-coagulation factors, B. Albumin, C. IgG and transferrin, D. Fibrinogen, E. Alpha-1-proteinase inhibitor and F. Alpha-1-acid glycoprotein.

Further experimentation with exchanging the order of the adsorption steps have shown that:

Column A must be first in order to avoid inactivation of the coagulation factors at pH 5.0 (used for column B)
Column C must be after column B in order to avoid excessive binding of albumin to column C and consequential serious contamination of alpha-1-proteinase inhibitor.

REFERENCES

Cohn et al, "*Separation into Fractions of Protein and Lipoprotein Components*" J. Am. Chem. Soc., 68, 459-475, 1946
E. J. Cohn et al., Preparation and Properties of Serum and Plasma Proteins, IV, A System for the Separation into Fractions of the Protein and Lipoprotein Components of Biological Tissues and Fluids, The Journal of the American Chemical Society, vol. LXVIII (January-July 1946), pp. 459-475
Scand. J. Immunol. Vol. 17, Suppl. 10, 41-56, 1983
Finette G. M. S. et al, Biotechnol. Prog., 1998, 14, pp 286-293
Malvern Instruments Ltd (Worcestershire, UK) in their Operators guide (MAN 0320 Issue 1.0 March 2004) to the Mastersizer 2000E
U.S. Pat. No. 2,390,074
U.S. Pat. No. 2,469,193
U.S. Pat. No. 6,617,133
U.S. Pat. No. 6,036,861
U.S. Pat. No. 4,481,189
EP 0 722 771
WO 01/85329
WO 92/18237
WO 2000/25884
WO 02/05923
WO 99/65586
WO 00/57982
WO 99/51316
WO 92/00799
WO 92/16292

The invention claimed is:

1. A process for the large-scale isolation of one or more proteins from a protein solution, wherein the protein solution is obtained from a source selected from the group consisting of human blood and a solution derived from human blood, and wherein the protein solution has not been supplemented with an alcohol, the process comprising the steps of:
   a) adjusting the pH of the solution to a pH in the range of 3 to 10;
   b) adjusting the ionic strength or conductivity of the protein solution to an ionic strength in the range of 0.0001 to 12 or a conductivity in the range of 0.01 to 1000 mS/cm;
   c) applying said protein solution to an adsorption column comprising an adsorbent, said adsorbent comprises a particle with at least one high density non-porous core, surrounded by a porous material, the adsorbent comprises a particle density of at least 1.5 g/ml and a mean volume particle diameter of at most 150 μm, whereby one or more proteins are bound to the adsorbent;
   d) obtaining a non-bound material fraction from the column, which non-bound material fraction contains at least one non-bound protein;
   e) subjecting the adsorbent to at least one elution buffer to elute at least one of the proteins bound to the adsorbent, thereby obtaining a bound material fraction; and
   f) subjecting the non-bound material fraction to further processing to obtain at least one non-bound protein therefrom.

2. The process according to claim 1, wherein the proteins are human blood proteins from the human blood solution.

3. The process according to claim 1, further comprising at least one virus elimination treatment.

4. The process according to claim 3, wherein the at least one virus elimination treatment is performed prior to contacting the protein solution with the adsorbent.

5. The process according to claim 3, wherein the virus elimination treatment involves addition of detergent and/or an organic solvent to the protein solution.

6. The process according to claim 1, wherein the adsorbent comprises a functionalized matrix polymer carrying a plurality of covalently attached functional groups comprising an aromatic ring-system, a heteroaromatic ring-system or one or more acidic groups.

7. The process according to claim 2, wherein the human blood proteins are selected from the group consisting of albumin, IgG, IgA, IgM, IgD, IgE, alpha-1-proteinase inhibitor, blood pro-coagulation protein, blood anti-coagulation protein, anti-angiogenic protein, α-2-antiplasmin, C-1 esterase inhibitor, apolipoprotein, HDL, LDL, Fibronectin, beta-2-glycoprotein I, fibrinogen, plasminogen, plasmin, plasminogen activator, plasminogen inhibitor, plasma protease inhibitor, anti-thrombin III, streptokinase, inter-alpha-trypsin inhibitor, α-2-macroglobulin, amyloid protein, ferritin, pre-albumin, GC-globulin, haemopexin, C3-complement, transferrin, urokinase and α-1-acid-glycoprotein.

8. The process according to claim 1, wherein, after applying the protein solution to the adsorption column, one or more proteins are washed out as a non-bound protein with one or more washing buffers.

9. The process according to claim 1, wherein one non-bound protein is an alpha-1-proteinase inhibitor.

10. The process according to claim 1, wherein, prior to applying the protein solution to the adsorption column, the pH of the protein solution is adjusted to a pH in the range of pH 3.0 to pH 10.0.

11. The process according to claim 10, wherein the pH-value for capturing and for elution is maintained in the range of pH 3.0 to pH 10.0.

12. The process according to claim 1, wherein, prior to applying the protein solution to the adsorption column, the ionic strength is adjusted.

13. The process according to claim 1, wherein, prior to applying the protein solution to the adsorption column, the conductivity is adjusted.

14. The process according to claim 1, wherein the flow rate of the protein solution through the column is at least 2 cm/min.

15. The process according to claim 1, wherein the adsorbent has a dynamic binding capacity at 10% break-through for said at least one protein of at least 5 g per liter sedimented adsorbent.

16. The process according to claim 1, wherein at least 2 proteins are isolated from the protein solution, wherein the proteins are selected from the group consisting of albumin, IgG, IgA, IgM, IgD, IgE, alpha-1-proteinase inhibitor, blood pro-coagulation protein, blood anti-coagulation protein, anti-angiogenic protein, α-2-antiplasmin, C-1 esterase inhibitor, apolipoprotein, HDL, LDL, Fibronectin, beta-2-glycoprotein I, fibrinogen, plasminogen, plasmin, plasminogen activator, plasminogen inhibitor, plasma protease inhibitor, anti-thrombin III, streptokinase, inter-alpha-trypsin inhibitor, α-2-macroglobulin, amyloid protein, ferritin, pre-albumin, GC-globulin, haemopexin, C3-complement, transferrin, urokinase and α-1-acid-glycoprotein, and wherein the proteins are isolated in at least 2 fractions.

17. The process according to claim 16, wherein at least 2 proteins are isolated from the protein solution, wherein the proteins are selected from the group consisting of α-1 proteinase inhibitor, IgG, human albumin, transferrin, thrombin, Factor II, Factor V, Factor VII, Factor VII, Factor IX, protein C, Protein S, α-1-acid-glycoprotein and fibrinogen, and wherein the proteins are isolated in at least 2 fractions.

18. The process according to claim 1, wherein at least one of the proteins bound to the adsorbent comprises fibrinogen and wherein the at least one non-bound protein comprises Factor II, Factor V, Factor VII, Factor VIII, von Willebrand factor, Factor VIII - von Willebrand factor complex, Factor IX, Factor X, Factor XI, C1 inhibitor, protein C and/or Protein S.

19. The process according to claim 1, wherein the bound proteins are albumin and IgG and the non-bound protein is α-1-proteinase inhibitor.

20. The process according to claim 19, wherein albumin and IgG are isolated from the bound fraction by stepwise elution.

21. The process according to claim 1, wherein fibrinogen and IgG are bound to the adsorbent and simultaneously albumin may be obtained as non-bound material from the adsorbent.

22. The process according to claim 21, wherein fibrinogen and IgG may be obtained from the adsorbent by stepwise elution.

23. The process according to claim 1, wherein the bound proteins are fibrinogen, albumin and IgG and the non-bound protein is α-1-proteinase inhibitor.

24. The process according to claim 23, wherein fibrinogen, albumin and IgG are obtained from the adsorbent by stepwise elution.

25. The process according to claim 1, wherein at least 2 of fibrinogen, albumin, and/or IgG are bound to the adsorbent and simultaneously α-1-acid glycoprotein is obtained as non-bound material from the adsorbent.

26. The process according to claim 25, wherein the at least 2 of fibrinogen, albumin and/or IgG are obtained from the adsorbent by stepwise elution.

27. The process according to claim 1, wherein the bound proteins are at least 2 of fibrinogen, albumin and/or IgG and the non-bound proteins are α-1-acid glycoprotein and/or α-1-proteinase inhibitor.

28. The process according to claim 27, wherein the at least 2 of fibrinogen, albumin and/or IgG may be obtained from the adsorbent by stepwise elution.

29. A process for the large-scale isolation of one or more proteins from a protein solution, wherein the protein solution is obtained from a source selected from the group consisting of human blood and a solution derived from human blood, and wherein the protein solution has not been supplemented with an alcohol, said process comprising the steps of:
  a) adjusting the pH of the protein solution to a pH in the range of 3 to 10;
  b) adjusting the ionic strength or conductivity of the protein solution to an ionic strength in the range of 0.0001 to 12 or a conductivity in the range of 0.01 to 1000 mS/cm;
  c) applying the protein solution to an adsorption column comprising an adsorbent, wherein the adsorbent comprises a functionalised matrix polymer carrying a plurality of covalently attached functional groups comprising an aromatic or heteroaromatic ring-system and one or more acidic groups, whereby one or more proteins are bound to the adsorbent;
  d) obtaining a non-bound material fraction from the column, which non-bound material fraction contains at least one non-bound protein;
  e) subjecting the adsorbent to at least one elution buffer to elute at least one of the proteins bound to the adsorbent; and
  f) subjecting the non-bound material fraction to further processing to isolate at least one non-bound protein therefrom.

30. The process according to claim 29, further comprising at least one virus elimination treatment.

31. The process according to claim 29, wherein one of the non-bound proteins is α-1-proteinase inhibitor.

32. The process according to claim 29, wherein one of the bound proteins is human albumin.

33. The process according to claim 29, wherein one of the bound proteins is fibrinogen.

34. The process according to claim 29, wherein one of the bound proteins is transferrin.

35. The process according to claim 29, wherein one of the non-bound proteins is α-1-acid glycoprotein.

36. The process according to claim 29, wherein one of the non-bound proteins is a coagulation or anticoagulation factor.

37. The process according to claim 36, wherein the coagulation or anti-coagulation factor is selected from the group consisting of Factor II, Factor V, Factor VII, Factor VIII, von Willebrand factor, Factor VIII - von Willebrand factor complex, Factor IX, Factor X, Factor XI, C1 inhibitor, protein C and Protein S.

38. A process for the large-scale isolation of one or more proteins from a protein solution, wherein the protein solution is obtained from a source selected from the group consisting of human blood and a solution derived from human blood, and wherein the protein solution has not been supplemented with an alcohol, said process comprising the steps of:
   a) providing a protein solution comprising one or more proteins obtained from a source selected from the group consisting of human blood or a solution derived from human blood, the protein solution having a preset pH and a preset ionic strength or conductivity;
   b) contacting the protein solution with an adsorbent, wherein the adsorbent comprises a particle with at least one high density non-porous core, surrounded by a porous material, whereby one or more proteins is bound to the adsorbent;
   c) subjecting the adsorbent to an elution buffer to elute at least one of the proteins bound to the adsorbent; and
   d) subjecting the adsorbent to one or more additional elution buffers to elute one or more remaining proteins bound to the adsorbent.

39. The process according to claim 38, further comprising at least one virus elimination treatment.

40. The process according to claim 38, wherein one of the proteins isolated from the protein solution is an α-1-proteinase inhibitor.

41. The process according to claim 38, wherein one of the proteins isolated from the protein solution is human albumin.

42. The process according to claim 38, wherein one of the proteins isolated from the protein solution is fibrinogen.

43. The process according to claim 38, wherein one of the proteins isolated from the protein solution is transferrin.

44. The process according to claim 38, wherein one of the proteins isolated from the protein solution is α-1- acid-glycoprotein.

45. The process according to claim 38, wherein one of the proteins isolated from the protein solution is a coagulation or anticoagulation factor.

46. The process according to claim 45, wherein the coagulation or anti-coagulation factor is selected from the group consisting of Factor II, Factor V, Factor VII, Factor VIII, von Willebrand factor, Factor VIII - von Willebrand factor complex, Factor IX, Factor X, Factor XI, C1 inhibitor, protein C and Protein S.

47. The process according to claim 1, wherein the protein solution is serum and/or plasma.

48. The process according to claim 2, wherein the human blood proteins are human plasma proteins or human serum proteins.

49. The process according to claim 16, wherein 3 proteins are isolated from the protein solution, and wherein the 3 proteins are isolated in 3 fractions.

50. The process according to claim 16, wherein 4 proteins are isolated from the protein solution, and wherein the 4 proteins are isolated in 4 fractions.

51. The process according to claim 16, wherein 5 proteins are isolated from the protein solution, and wherein the 5 proteins are isolated in 5 fractions.

52. The process according to claim 16, wherein 6 proteins are isolated from the protein solution, and wherein the 6 proteins are isolated in 6 fractions.

53. The process according to claim 17, wherein 3 proteins are isolated from the protein solution, and wherein the 3 proteins are isolated in 3 fractions.

54. The process according to claim 17, wherein 4 proteins are isolated from the protein solution, and wherein the 4 proteins are isolated in 4 fractions.

55. The process according to claim 17, wherein 5 proteins are isolated from the protein solution, and wherein the 5 proteins are isolated in 5 fractions.

56. The process according to claim 17, wherein 6 proteins are isolated from the protein solution, and wherein the 6 proteins are isolated in 6 fractions.

57. The process according to claim 25, wherein fibrinogen, albumin and IgG are bound to the adsorbent.

58. The process according to claim 27, wherein fibrinogen, albumin and IgG are bound to the adsorbent.

59. The process according to claim 5, wherein the detergent and/or organic solvent is selected from the group consisting of polysorbate detergents, octylphenol ethoxylate detergents, and tri-n-butyl phosphate.

60. The process of claim 1, wherein the human blood comprises human plasma or serum.

61. The process of claim 7 wherein the blood pro-coagulation protein or anti-coagulation protein is selected from the group consisting of Factor II, Factor V, Factor VII, Factor VIII, von Willebrand factor, Factor VIII - von Willebrand factor complex, Factor IX, Factor X, Factor XI, C1 inhibitor, protein C and Protein S.

62. The process of claim 16 wherein the blood pro-coagulation protein or anti-coagulation protein is selected from the group consisting of Factor II, Factor V, Factor VII, Factor VIII, von Willebrand factor, Factor VIII - von Willebrand factor complex, Factor IX, Factor X, Factor XI, C1 inhibitor, protein C and Protein S.

* * * * *